United States Patent

(12) United States Patent
Georgantas, III et al.

(10) Patent No.: US 11,016,099 B2
(45) Date of Patent: May 25, 2021

(54) PREDICTION OF CLINICAL RESPONSE TO IL23-ANTAGONISTS USING IL23 PATHWAY BIOMARKERS

(71) Applicants: AMGEN INC., Thousand Oaks, CA (US); MEDIMMUNE, LLC, Gaithersburg, MD (US)

(72) Inventors: Robert W. Georgantas, III, Gaithersburg, MD (US); Chris Morehouse, Gaithersburg, MD (US); Brandon Higgs, Gaithersburg, MD (US); Koustubh Ranade, Gaithersburg, MD (US); Katie Streicher, Gaithersburg, MD (US); William Rees, Thousand Oaks, CA (US); Meina Liang, Gaithersburg, MD (US); Raffaella Faggioni, Gaithersburg, MD (US); Jing Li, Gaithersburg, MD (US); Inna Vainshtein, Gaithersburg, MD (US); Yen-Wah Lee, Gaithersburg, MD (US); Jingjing Chen, Gaithersburg, MD (US); Robert A. Gasser, Jr., Gaithersburg, MD (US)

(73) Assignees: AMGEN INC., Thousand Oaks, CA (US); MEDIMMUNE, LLC, Gaithersburg, MD (US)

( * ) Notice: Subject to any disclaimer, the term of this patent is extended or adjusted under 35 U.S.C. 154(b) by 36 days.

(21) Appl. No.: 15/759,330

(22) PCT Filed: Sep. 16, 2016

(86) PCT No.: PCT/US2016/052060
§ 371 (c)(1),
(2) Date: Mar. 12, 2018

(87) PCT Pub. No.: WO2017/049035
PCT Pub. Date: Mar. 23, 2017

(65) Prior Publication Data
US 2018/0252728 A1 Sep. 6, 2018

Related U.S. Application Data

(60) Provisional application No. 62/220,062, filed on Sep. 17, 2015.

(51) Int. Cl.
*G01N 33/68* (2006.01)
*C07K 16/24* (2006.01)
*A61K 39/00* (2006.01)

(52) U.S. Cl.
CPC ....... *G01N 33/6869* (2013.01); *C07K 16/244* (2013.01); *A61K 2039/505* (2013.01); *G01N 2800/065* (2013.01); *G01N 2800/52* (2013.01); *Y02A 50/30* (2018.01)

(58) Field of Classification Search
None
See application file for complete search history.

(56) References Cited

U.S. PATENT DOCUMENTS

| 4,833,074 A | 5/1989 | Fagerhol et al. |
| 5,455,160 A | 10/1995 | Fagerhol et al. |
| 6,171,586 B1 | 1/2001 | Lam et al. |
| 6,225,072 B1 | 5/2001 | Holtund et al. |
| 7,445,905 B2 | 11/2008 | Gurney et al. |
| 7,491,391 B2 | 2/2009 | Benson et al. |
| 7,790,862 B2 | 9/2010 | Lewis et al. |
| 7,807,160 B2 | 10/2010 | Presta et al. |
| 7,807,414 B2 | 10/2010 | Benson et al. |
| 7,872,102 B2 | 1/2011 | Beidler et al. |
| 7,935,344 B2 | 5/2011 | Benson et al. |
| 8,362,212 B2 | 1/2013 | Presta |

(Continued)

FOREIGN PATENT DOCUMENTS

| EP | 1311679 B1 | 10/2008 |
| EP | 1986627 A2 | 11/2008 |

(Continued)

OTHER PUBLICATIONS

Usta et al, Plos One, 2014; vol. 9, No. 3, pp. 1-12.*

(Continued)

*Primary Examiner* — Joanne Hama
*Assistant Examiner* — Fozia Hamud
(74) *Attorney, Agent, or Firm* — Marshall, Gerstein & Borun LLP

(57) ABSTRACT

The present invention relates to the use of components of the IL23 pathway as biomarkers, e.g., IL22, LCN2 and combinations thereof, to stratify or identify populations of patients suffering from IL23-mediated diseases (e.g., Crohn's disease) responsive to treatment with an anti-IL23 antagonist (including, e.g., anti-IL23 antibodies or antigen-binding fragments thereof). Levels of IL23 pathway biomarkers above or below a predetermined threshold can be used, for example, (i) to determine whether a patient with an IL23-mediated disease or disorder such a Crohn's disease is eligible or non-eligible for treatment with a therapeutic agent (e.g., an ant-IL23 antibody), (ii) to determine whether treatment with a certain agent should be commenced, suspended, or modified, (iii) to diagnose whether the IL23-mediated disease is treatable or not treatable with a specific therapeutic agent, or (iv) to predict the outcome of treating the IL23-mediated disease with a specific therapeutic agent.

22 Claims, 12 Drawing Sheets

Figure 1:
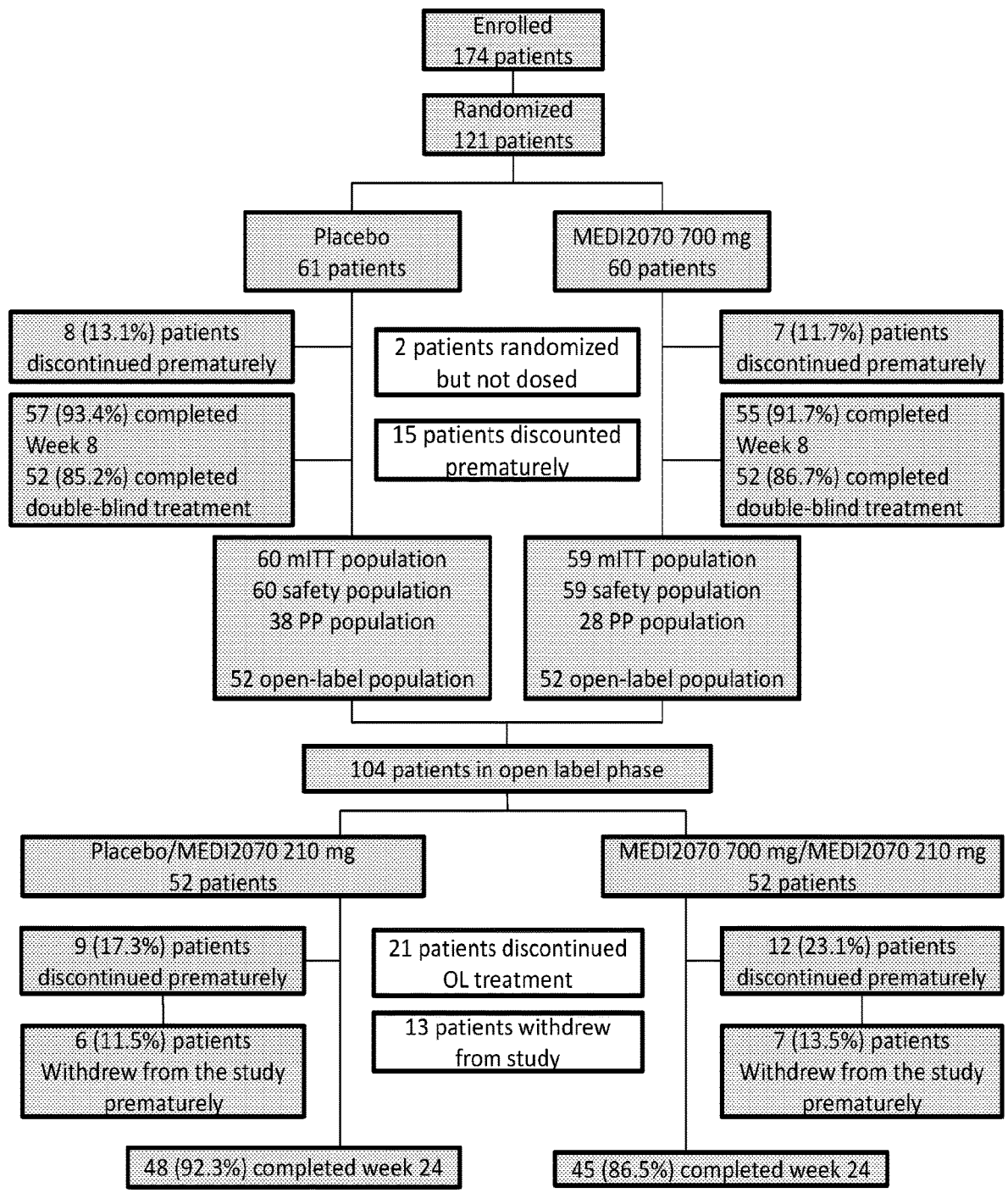

Specification includes a Sequence Listing.

(56) References Cited

U.S. PATENT DOCUMENTS

| | | | |
|---|---|---|---|
| 8,524,230 | B2 | 9/2013 | Cua et al. |
| 8,541,180 | B1 | 9/2013 | Hanaway et al. |
| 8,722,033 | B2 | 5/2014 | Towne et al. |
| 9,487,580 | B2 | 11/2016 | Towne et al. |
| 9,951,129 | B2 | 4/2018 | Towne et al. |
| 2005/0261191 | A1 | 11/2005 | Barasch et al. |
| 2007/0066550 | A1 | 3/2007 | Diener et al. |
| 2007/0203216 | A1 | 8/2007 | Ebert et al. |
| 2007/0212723 | A1 | 9/2007 | Dudley et al. |
| 2009/0123479 | A1 | 5/2009 | Bembridge et al. |
| 2009/0123946 | A1 | 5/2009 | Birkenmeyer et al. |
| 2009/0233304 | A1 | 9/2009 | Harris et al. |
| 2009/0269777 | A1 | 10/2009 | Birkenmeyer et al. |
| 2010/0105150 | A1 | 4/2010 | Adamczyk et al. |
| 2010/0227775 | A1 | 9/2010 | Birkenmeyer et al. |
| 2011/0212099 | A1 | 9/2011 | Liang et al. |
| 2011/0212104 | A1 | 9/2011 | Beaumont et al. |
| 2012/0128689 | A1 | 5/2012 | Clarkson et al. |
| 2012/0171221 | A1 | 7/2012 | Hamm-Alvarez et al. |
| 2012/0264917 | A1 | 10/2012 | Saunders et al. |
| 2012/0282269 | A1 | 11/2012 | Barrett et al. |
| 2013/0005596 | A1 | 1/2013 | Gong et al. |
| 2013/0303398 | A1 | 11/2013 | Panja |
| 2014/0080134 | A1 | 3/2014 | Platt et al. |
| 2014/0141990 | A1 | 5/2014 | Jones et al. |
| 2014/0199709 | A1 | 7/2014 | Gong et al. |
| 2014/0227725 | A1 | 8/2014 | Fagerhol |
| 2014/0342468 | A1 | 11/2014 | Todd et al. |
| 2015/0065530 | A1 | 3/2015 | Merchant et al. |
| 2016/0000936 | A1 | 1/2016 | Cuff et al. |
| 2017/0089892 | A1 | 3/2017 | Aghvanyan et al. |
| 2018/0252728 | A1 | 9/2018 | Georgantas, III et al. |

FOREIGN PATENT DOCUMENTS

| | | | |
|---|---|---|---|
| EP | 2029171 | A1 | 3/2009 |
| EP | 2352762 | A1 | 8/2011 |
| EP | 2356458 | A1 | 8/2011 |
| EP | 2451969 | A2 | 5/2012 |
| EP | 2661627 | A1 | 11/2013 |
| EP | 2702411 | A1 | 3/2014 |
| EP | 2742154 | A2 | 6/2014 |
| EP | 3143401 | A1 | 3/2017 |
| EP | 3349854 | A1 | 7/2018 |
| EP | 3393515 | A1 | 10/2018 |
| WO | WO-1999/05280 | A1 | 2/1999 |
| WO | WO-2006/091035 | A1 | 8/2006 |
| WO | WO-2007/027714 | A2 | 3/2007 |
| WO | WO-2007/076524 | A2 | 7/2007 |
| WO | WO-2007/093183 | A2 | 8/2007 |
| WO | WO-2007/147019 | A2 | 12/2007 |
| WO | WO-2007/149814 | A1 | 12/2007 |
| WO | WO-2008/003926 | A1 | 1/2008 |
| WO | WO-2008/028044 | A2 | 3/2008 |
| WO | WO-2008/103432 | A1 | 8/2008 |
| WO | WO-2008/103473 | A1 | 8/2008 |
| WO | WO-2009/043933 | A1 | 4/2009 |
| WO | WO-2009/052392 | A1 | 4/2009 |
| WO | WO-2009/062520 | A1 | 5/2009 |
| WO | WO-2009/082624 | A2 | 7/2009 |
| WO | WO-2010/0027766 | A1 | 3/2010 |
| WO | WO-2010/048354 | A1 | 4/2010 |
| WO | WO-2010/062663 | A1 | 6/2010 |
| WO | WO-2010/129964 | A1 | 11/2010 |
| WO | WO-2011/005779 | A2 | 1/2011 |
| WO | WO-2011/088120 | A1 | 7/2011 |
| WO | WO-2012/009760 | A1 | 1/2012 |
| WO | WO-2012/061448 | A1 | 5/2012 |
| WO | WO-2012/093254 | A1 | 7/2012 |
| WO | WO-2012/094651 | A2 | 7/2012 |
| WO | WO-2012/115885 | A1 | 8/2012 |
| WO | WO-2012/149550 | A1 | 11/2012 |
| WO | WO-2012/175602 | A2 | 12/2012 |
| WO | WO-2012/175616 | A1 | 12/2012 |
| WO | WO-2013/022995 | A2 | 2/2013 |
| WO | WO-2013/132338 | A2 | 9/2013 |
| WO | WO-2013/132347 | A2 | 9/2013 |
| WO | WO-2015/175856 | A1 | 11/2015 |
| WO | WO-2015/191783 | A2 | 12/2015 |
| WO | WO-2016/014775 | A1 | 1/2016 |
| WO | WO-2017/093750 | A1 | 6/2017 |
| WO | WO-2018/089693 | A2 | 5/2018 |
| WO | WO-2018/119626 | A1 | 7/2018 |

OTHER PUBLICATIONS

Paul, Fundamental Immunology, 3rd Edition, 1993, pp. 292-295.*
Rudikoff et al. (Proc Natl Acad Sci USA. vol. 79, p. 1979, 1982.*
Colman P. M. (Research in Immunology, 11994; vol. 45, pp. 33-36.*
Casset et al. (Biochemical and Biophysical Research Communications, 2003 vol. 307, pp. 198-205.*
Leonard et al, Lancet, 2008, vol. 371, pp. 1665-1674.*
Brand et al., "Crohn's disease: Th1, TH17 or both? The change of a paradigm: new immunological and genetic insights implicate Th17 cells in the pathogenesis of Crohn's disease," Recent advances in basic science, 58(8):1152-1167 (2009).
Duvallet et al., "Interleukin-23: A key cytokine in inflammatory diseases," Annals of Medicine 43:503-511 (2011).
Ghosh et al., "Successful Therapy of Visceral Leishmaniasis with Curdlan Involves T-Helper 17 Cytokines," Journal of Infectious Diseases 207:1016-1025 (2013).
Ahern et al., The interleukin-23 axis in intestinal inflammation, Immunol. Rev., 226:147-59 (2008).
Akerstrom et al., Lipocalins: unity in diversity, Biochim. Biophys. Acta, 1482(1-2):1-8 (2000).
Angriman et al., Enzymes in feces: useful markers of chronic inflammatory bowel disease, Clin. Chim. Acta, 381(1):63-8 (2007).
Behnsen et al., The cytokine IL-22 promotes pathogen colonization by suppressing related commensal bacteria, Immunity, 40(2):262-73 (2014).
Best et al., Development of a Crohn's disease activity index. National Cooperative Crohn's Disease Study, Gastroenterology, 70(3):439-44 (1976).
Boniface et al., IL-22 inhibits epidermal differentiation and induces proinflammatory gene expression and migration of human keratinocytes, J. Immunol., 174(6):3695-702 (2005).
Brand et al., IL-22 is increased in active Crohn's disease and promotes proinflammatory gene expression and intestinal epithelial cell migration, Am. J. Physiol. Gastrointest. Liver Physiol., 290(4):G821-38 (2006).
Bundegaard et al., Molecular cloning and expression of a cDNA encoding NGAL: a lipocalin expressed in human neutrophils, Biochem. Biophys. Res. Commun., 202(3):1468-75 (1994).
Burton et al., Association scan of 14,500 nonsynonymous SNPs in four diseases identifies autoimmunity variants, Nat. Genet., 39(11):1329-37 (2007).
Buxton et al., Mapping from disease-specific measures to utility: an analysis of the relationships between the Inflammatory Bowel Disease Questionnaire and Crohn's Disease Activity Index in Crohn's disease and measures of utility, Value Health, 10(3):214-20 (2007).
Cargill et al., A large-scale genetic association study confirms IL12B and leads to the identification of IL23R as psoriasis-risk genes, Am. J. Hum. Genet., 80(2):273-90 (2007).
Corbin et al., Metal chelation and inhibition of bacterial growth in tissue abscesses, Science, 319(5865):962-5 (2008).
Cua et al., Interleukin-23 rather than interleukin-12 is the critical cytokine for autoimmune inflammation of the brain, Nature, 421(6924):744-8 (2003).
Dige et al., Increased levels of circulating Th17 cells in quiescent versus active Crohn's disease, J. Crohns Colitis, 7(3):248-55 (2013).
Dong, Diversification of T-helper-cell lineages: finding the family root of IL-17-producing cells, Nat. Rev. Immunol., 6(4):329-33 (2006).
Duerr et al., A genome-wide association study identifies IL23R as an inflammatory bowel disease gene, Science, 314(5804):1461-3 (2006).

(56) References Cited

OTHER PUBLICATIONS

Dumoutier et al., Human interleukin-10-related T cell-derived inducible factor: molecular cloning and functional characterization as an hepatocyte-stimulating factor, Proc. Natl. Acad. Sci. USA, 97(18):10144-9 (2000).

El-Behi et al., The encephalitogenicity of T(H)17 cells is dependent on IL-1- and IL-23-induced production of the cytokine GM-CSF, Nat. Immunol., 12(6):568-75 (2011).

Faragó et al., Functional variants of interleukin-23 receptor gene confer risk for rheumatoid arthritis but not for systemic sclerosis, Ann. Rheum. Dis., 67(2):248-50 (2008).

Flower, The lipocalin protein family: structure and function, Biochem. J., 318(Pt. 1):1-14 (1996).

Foell et al., S100 proteins expressed in phagocytes: a novel group of damage-associated molecular pattern molecules, J. Leukoc. Biol., 81(1):28-37 (2007).

Gaffen et al., The IL-23-IL-17 immune axis: from mechanisms to therapeutic testing, Nat. Rev. Immunol., 14(9):585-600 (2014).

Gordon et al., A phase III, randomized, controlled trial of the fully human IL-12/23 mAb briakinumab in moderate-to-severe psoriasis, J. Invest. Dermatol., 132(2):304-14 (2012).

Gottlieb et al., Efficacy and safety of briakinumab vs. etanercept and placebo in patients with moderate to severe chronic plaque psoriasis, Br. J. Dermatol., 165(3):652-60 (2011).

Guttman-Yassky et al., Low expression of the IL-23/Th17 pathway in atopic dermatitis compared to psoriasis, J. Immunol., 181(10):7420-7 (2008).

Guyatt et al., A new measure of health status for clinical trials in inflammatory bowel disease, Gastroenterology, 96(3):804-10 (1989).

Haider et al., Identification of cellular pathways of "type 1," Th17 T cells, and TNF- and inducible nitric oxide synthase-producing dendritic cells in autoimmune inflammation through pharmacogenomic study of cyclosporine A in psoriasis, J. Immunol., 180(3):1913-20 (2008).

Illes et al., 3'UTR C2370A allele of the IL-23 receptor gene is associated with relapsing-remitting multiple sclerosis, Neurosci. Lett., 431(1):36-8 (2008).

International Application No. PCT/US2016/52060, International Preliminary Report on Patentability, dated Mar. 20, 2018.

International Application No. PCT/US2016/52060, International Search Report and Written Opinion, dated Dec. 1, 2016.

Keshet et al., Diagnostic and prognostic significance of serum C-reactive protein levels in patients admitted to the department of medicine, Am. J. Med. Sci., 337(4):248-55 (2009).

Khader et al., Th17 cells at the crossroads of innate and adaptive immunity against infectious diseases at the mucosa, Mucosal Immunol., 2(5):403-11 (2009).

Kimball et al., Long-term efficacy and safety of ustekinumab in patients with moderate to severe psoriasis through 5 years of follow-up: results from teh PHOENIX 1 long-term extension, Br. J. Dermatology, 167(Suppl 1): Abstract P94 (2012).

Kjeldsen et al., Isolation and primary structure of NGAL, a novel protein associated with human neutrophil gelatinase, J. Biol. Chem., 268(14):10425-32 (1993).

Krueger et al., Anti-IL-23A mAb BI 655066 for treatment of moderate-to-severe psoriasis: Safety, efficacy, pharmacokinetics, and biomarker results of a single-rising-dose, randomized, double-blind, placebo-controlled trial, J. Allergy Clin. Immunol., 136(1):116-24 (2015).

Langhorst et al., Noninvasive markers in the assessment of intestinal inflammation in inflammatory bowel diseases: performance of fecal lactoferrin, calprotectin, and PMN-elastase, CRP, and clinical indices, Am. J. Gastroenterol., 10391):162-9 (2008).

Langley et al., Interim results from an open-label extension study of briakinumab for the treatment of moderate to severe psoriasis, Poster Abstract, vol. 66, Issue 4, Supplement 1, pp. A1-A16, AB1-AB296 (Apr. 2012).

Leach et al., Serum and mucosal S100 proteins, calprotectin (S100A8/S100A9) and S100A12, are elevated at diagnosis in children with inflammatory bowel disease, Scand J. Gastroenterol., 42(11):1321-31 (2007).

Lee et al., Increased expression of interleukin 23 p19 and p40 in lesional skin of patients with psoriasis vulgaris, J. Exp. Med., 199(1):125-30 (2004).

Leonardi et al., Efficacy and safety of ustekinumab, a human interleukin-12/23 monoclonal antibody, in patients with psoriasis: 76-week results from a randomised, double-blind, placebo-controlled trial (PHOENIX 1), Lancet, 371(9625):1665-74 (2008).

Li et al., Increased IL-23p19 expression in multiple sclerosis lesions and its induction in microglia, Brain, 130(Pt. 2):490-501 (2007).

Lügering et al., Immunohistochemical distribution and serum levels of the Ca(2+)-binding proteins MRP8, MRP14 and their heterodimeric form MRP8/14 in Crohn's disease, Digestion, 56(5):406-14 (1995).

Mannon et al., Anti-interleukin-12 antibody for active Crohn's disease, N. Engl. J. Med., 351(20):2069-79 (2004).

Nakae et al., Phenotypic differences between Th1 and Th17 cells and negative regulation of Th1 cell differentiation by IL-17, J. Leukoc. Biol., 81(5):1258-68 (2007).

Papp et al., Efficacy and safety of ustekinumab, a human interleukin-12/23 monoclonal antibody, in patients with psoriasis: 52-week results from a randomised, double-blind, placebo-controlled trial (PHOENIX 2), Lancet, 371(9625):1675-84 (2008).

Quiniou et al., Specific targeting of the IL-23 receptor, using a novel small peptide noncompetitive antagonist, decreases the inflammatory response, Am. J. Physiol. Regul. Integr. Comp. Physiol., 307(10):R1216-30 (2014).

Reich et al., A 52-week trial comparing briakinumab with methotrexate in patients with psoriasis, N. Engl. J. Med., 365(17):1586-96 (2011).

Rutgeerts et al., Review article: the expanding role of biological agents in the treatment of inflammatory bowel disease—focus on selective adhesion molecule inhibition, Aliment. Pharmacol. Ther., 17(12):1435-50 (2003).

Sandborn et al., A randomized trial of Ustekinumab, a human interleukin-12/23 monoclonal antibody, in patients with moderate-to-severe Crohn's disease, Gastroenterology, 135(4):1130-41 (2008).

Sandborn et al., Adalimumab induction therapy for Crohn disease previously treated with infliximab: a randomized trial, Ann. Intern. Med., 146(12):829-38 (2007).

Sandborn et al., Ustekinumab induction and maintenance therapy in refractory Crohn's disease, N. Engl. J. Med., 367(16):1519-28 (2012).

Sands et al., Effects of vedolizumab induction therapy for patients with Crohn's disease in whom tumor necrosis factor antagonist treatment failed, Gastroenterology, 147(3):618-27 (2014).

Sands et al., Infliximab maintenance therapy for fistulizing Crohn's disease, N. Engl. J. Med., 350(9):876-85 (2004).

Schmechel et al., Linking genetic susceptibility to Crohn's disease with Th17 cell function: IL-22 serum levels are increased in Crohn's disease and correlate with disease activity and IL23R genotype status, Inflamm. Bowel Dis., 14(2):204-12 (2008).

Schmidt et al., Expression of interleukin-12-related cytokine transcripts in inflammatory bowel disease: elevated interleukin-23p19 and interleukin-27p28 in Crohn's disease but not in ulcerative colitis, Inflamm. Bowel Dis., 11(1):16-23 (2005).

Shang et al., Human heart failure is associated with abnormal C-terminal splicing variants in the cardiac sodium channel, Circ. Res., 101(11):1146-54 (2007).

Sofen et al., Clobetasol propionate 0.05% spray for the management of moderate-to-severe plaque psoriasis of the scalp: results from a randomized controlled trial, J. Drugs Dermatol., 10(8):885-92 (2011).

Sonnenberg et al., Functional biology of the IL-22-IL-22R pathway in regulating immunity and inflammation at barrier surfaces, Adv. Immunol., 107:1-29 (2010).

Stallhofer et al., Lipocalin-2 Is a Disease Activity Marker in Inflammatory Bowel Disease Regulated by IL-17A, IL-22, and TNF-a and Modulated by IL23R Genotype Status, Inflamm. Bowel Dis., 21(10):2327-40 (2015).

Strober et al., Efficacy and safety results from a phase III, randomized controlled trial comparing the safety and efficacy of briakinumab

(56) References Cited

OTHER PUBLICATIONS with etanercept and placebo in patients with moderate to severe chronic plaque psoriasis, Br. J. Dermatol., 165(3):661-8 (2011).
Toedter et al., Relationship of C-reactive protein with clinical response after therapy with ustekinumab in Crohn's disease, Am. J. Gastroenterol., 104(11):2768-73 (2009).
Tzellos et al., Association of anti-IL-12/23 biologic agents ustekinumab and briakinumab with major adverse cardiovascular events, J. Eur. Acad. Dermatol. Venereol., 27(12):1586-7 (2013).
Vaknin-Dembinsky et al., IL-23 is increased in dendritic cells in multiple sclerosis and down-regulation of IL-23 by antisense oligos increases dendritic cell IL-10 production, J. Immunol., 176(12):7768-74 (2006).
Van Roon et al., Diagnostic precision of fecal calprotectin for inflammatory bowel disease and colorectal malignancy, Am. J. Gastroenterol., 102(4):803-13 (2007).
Veldhoen et al., TGFbeta in the context of an inflammatory cytokine milieu supports de novo differentiation of IL-17-producing T cells, Immunity, 24(2):179-89 (2006).
Vermeire et al., C-reactive protein as a marker for inflammatory bowel disease, Inflamm. Bowel Dis., 10(5):661-5 (2004).
Voitk et al., Experience with elemental diet in the treatment of inflammatory bowel disease. Is this primary therapy?, Arch. Surg., 107(2):329-33 (1973).
Wilson et al., Development, cytokine profile and function of human interleukin 17-producing helper T cells, Nat. Immunol., 8(9):950-7 (2007).
Xie et al., Interleukin (IL)-22, a novel human cytokine that signals through the interferon receptor-related proteins CRF2-4 and IL-22R, J. Biol. Chem., 275(40):31335-9 (2000).
Yago et al., IL-23 induces human osteoclastogenesis via IL-17 in vitro, and anti-IL-23 antibody attenuates collagen-induced arthritis in rats, Arthritis Res. Ther., 9(5):R96 (2007).
Yamamoto et al., Enteral nutrition to suppress postoperative Crohn's disease recurrence: a five-year prospective cohort study, Int. J. Colorectal Dis., 28(3):335-40 (2013).
Zheng et al., Interleukin-22 mediates early host defense against attaching and effacing bacterial pathogens, Nat. Med., 14(3):282-9 (2008).

* cited by examiner

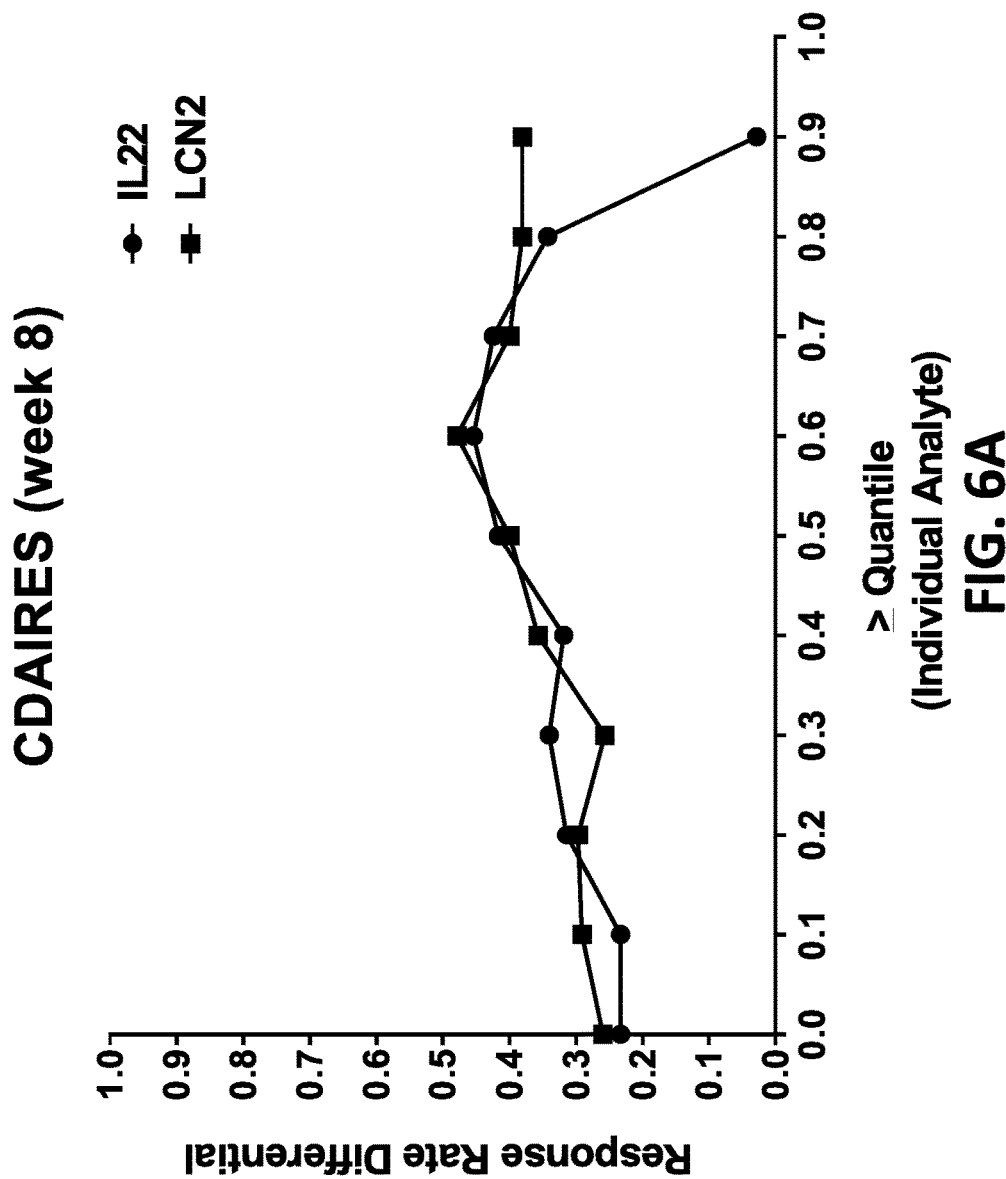

SEQUENCE LISTING

<160> NUMBER OF SEQ ID NOS: 50

<210> SEQ ID NO 1
<211> LENGTH: 1147
<212> TYPE: DNA
<213> ORGANISM: Homo sapiens

<400> SEQUENCE: 1

```
cgaccaggtt ctccttcccc agtcaccagt tgctcgagtt agaattgtct gcaatggccg      60
ccctgcagaa atctgtgagc tctttcctta tggggaccct ggccaccagc tgcctccttc     120
tcttggccct cttggtacag ggaggagcag ctgcgcccat cagctcccac tgcaggcttg     180
acaagtccaa cttccagcag ccctatatca ccaaccgcac cttcatgctg gctaaggagg     240
ctagcttggc tgataacaac acagacgttc gtctcattgg ggagaaactg ttccacggag     300
tcagtatgag tgagcgctgc tatctgatga agcaggtgct gaacttcacc cttgaagaag     360
tgctgttccc tcaatctgat aggttccagc cttatatgca ggaggtggtg cccttcctgg     420
ccaggctcag caacaggcta agcacatgtc atattgaagg tgatgacctg catatccaga     480
ggaatgtgca aaagctgaag gacacagtga aaaagcttgg agagagtgga gagatcaaag     540
caattggaga actggatttg ctgtttatgt ctctgagaaa tgcctgcatt tgaccagagc     600
aaagctgaaa aatgaataac taacccccctt tccctgctag aaataacaat tagatgcccc     660
aaagcgattt ttttttaacca aaaggaagat gggaagccaa actccatcat gatgggtgga     720
ttccaaatga accctgcgt tagttacaaa ggaaaccaat gccacttttg tttataagac     780
cagaaggtag actttctaag catagatatt tattgataac atttcattgt aactggtgtt     840
ctatacacag aaaacaattt attttttaaa taattgtctt tttccataaa aaagattact     900
ttccattcct tagggaaa aaacccctaa atagcttcat gtttccataa tcagtacttt         960
atatttataa atgtatttat tattattata agactgcatt ttatttatat cattttatta    1020
atatggattt atttatagaa acatcattcg atattgctac ttgagtgtaa ggctaatatt    1080
gatatttatg acaataatta tagagctata acatgtttat ttgacctcaa taaacacttg    1140
gatatcc                                                              1147
```

<210> SEQ ID NO 2
<211> LENGTH: 179
<212> TYPE: PRT

<213> ORGANISM: Homo sapiens

<400> SEQUENCE: 2

```
Met Ala Ala Leu Gln Lys Ser Val Ser Ser Phe Leu Met Gly Thr Leu
1               5                   10                  15
Ala Thr Ser Cys Leu Leu Leu Leu Ala Leu Leu Val Gln Gly Gly Ala
            20                  25                  30
Ala Ala Pro Ile Ser Ser His Cys Arg Leu Asp Lys Ser Asn Phe Gln
        35                  40                  45
Gln Pro Tyr Ile Thr Asn Arg Thr Phe Met Leu Ala Lys Glu Ala Ser
    50                  55                  60
Leu Ala Asp Asn Asn Thr Asp Val Arg Leu Ile Gly Glu Lys Leu Phe
65                  70                  75                  80
His Gly Val Ser Met Ser Glu Arg Cys Tyr Leu Met Lys Gln Val Leu
                85                  90                  95
Asn Phe Thr Leu Glu Glu Val Leu Phe Pro Gln Ser Asp Arg Phe Gln
            100                 105                 110
Pro Tyr Met Gln Glu Val Val Pro Phe Leu Ala Arg Leu Ser Asn Arg
        115                 120                 125
Leu Ser Thr Cys His Ile Glu Gly Asp Asp Leu His Ile Gln Arg Asn
    130                 135                 140
Val Gln Lys Leu Lys Asp Thr Val Lys Lys Leu Gly Glu Ser Gly Glu
145                 150                 155                 160
Ile Lys Ala Ile Gly Glu Leu Asp Leu Leu Phe Met Ser Leu Arg Asn
                165                 170                 175
Ala Cys Ile
```

<210> SEQ ID NO 3
<211> LENGTH: 840
<212> TYPE: DNA
<213> ORGANISM: Homo sapiens

<400> SEQUENCE: 3

```
actcgccacc tcctcttcca cccctgccag gcccagcagc caccacagcg cctgcttcct    60
cggccctgaa atcatgcccc taggtctcct gtggctgggc ctagccctgt gggggctct   120
gcatgcccag gcccaggact ccacctcaga cctgatccca gccccacctc tgagcaaggt   180
ccctctgcag cagaacttcc aggacaacca attccagggg aagtggtatg tggtaggcct   240
ggcagggaat gcaattctca gagaagacaa agacccgcaa agatgtatg ccaccatcta   300
tgagctgaaa gaagacaaga gctacaatgt cacctccgtc ctgtttagga aaaagaagtg   360
tgactactgg atcaggactt ttgttccagg ttgccagccc ggcgagttca cgctgggcaa   420
cattaagagt taccctggat taacgagtta cctcgtccga gtggtgagca ccaactacaa   480
ccagcatgct atggtgttct tcaagaaagt ttctcaaaac agggagtact caagatcac   540
cctctacggg agaaccaagg agctgacttc ggaactaaag agaacttca tccgcttctc   600
caaatctctg ggcctcctg aaaaccacat cgtcttccct gtcccaatcg accagtgtat   660
cgacggctga gtgcacaggt gccgccagct gccgcaccag cccgaacacc attgagggag   720
ctgggagacc ctccccacag tgccacccat gcagctgctc cccaggccac cccgctgatg   780
gagccccacc ttgtctgcta ataaacatg tgccctcagg ccaaaaaaaa aaaaaaaaa   840
```

<210> SEQ ID NO 4
<211> LENGTH: 198
<212> TYPE: PRT

<213> ORGANISM: Homo sapiens

<400> SEQUENCE: 4

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
            20                  25                  30

Leu Ser Lys Val Pro Leu Gln Gln Asn Phe Gln Asp Asn Gln Phe Gln
        35                  40                  45

Gly Lys Trp Tyr Val Val Gly Leu Ala Gly Asn Ala Ile Leu Arg Glu
50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Asp Gln Cys Ile Asp Gly
        195

<210> SEQ ID NO 5
<211> LENGTH: 124
<212> TYPE: PRT
<213> ORGANISM: Homo sapiens

<400> SEQUENCE: 5

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Glu Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Thr Ser Ser Trp Tyr Pro Asp Ala Phe Asp
            100                 105                 110

Ile Trp Gly Gln Gly Thr Met Val Thr Val Ser Ser
        115                 120

<210> SEQ ID NO 6
<211> LENGTH: 111
<212> TYPE: PRT

<213> ORGANISM: Homo sapiens

<400> SEQUENCE: 6

```
Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Thr Gly Ala Gly
            20                  25                  30
Tyr Asp Val His Trp Tyr Gln Gln Val Pro Gly Thr Ala Pro Lys Leu
        35                  40                  45
Leu Ile Tyr Gly Ser Gly Asn Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Asp Ser Ser
                85                  90                  95
Leu Ser Gly Trp Val Phe Gly Gly Gly Thr Arg Leu Thr Val Leu
            100                 105                 110
```

<210> SEQ ID NO 7
<211> LENGTH: 2024
<212> TYPE: DNA
<213> ORGANISM: Homo sapiens

<400> SEQUENCE: 7

| | | | | | |
|---|---|---|---|---|---|
| aaggcaagag | atctaggact | tctagcccct | gaactttcag | ccgaatacat | cttttccaaa | 60 |
| ggagtgaatt | caggcccttg | tatcactggc | agcaggacgt | gaccatggag | aagctgttgt | 120 |
| gtttcttggt | cttgaccagc | ctctctcatg | cttttggcca | gacagacatg | tcgaggaagg | 180 |
| cttttgtgtt | tcccaaagag | tcggatactt | cctatgtatc | cctcaaagca | ccgttaacga | 240 |
| agcctctcaa | agccttcact | gtgtgcctcc | acttctacac | ggaactgtcc | tcgaccgtg  | 300 |
| ggtacagtat | tttctcgtat | gccaccaaga | gacaagacaa | tgagattctc | atattttggt | 360 |
| ctaaggatat | aggatacagt | tttacagtgg | gtgggtctga | aatattattc | gaggttcctg | 420 |
| aagtcacagt | agctccagta | cacatttgta | caagctggga | gtccgcctca | gggatcgtgg | 480 |
| agttctgggt | agatgggaag | cccagggtga | ggaagagtct | gaagaaggga | tacactgtgg | 540 |
| gggcagaagc | aagcatcatc | ttggggcagg | agcaggattc | cttcggtggg | aactttgaag | 600 |
| gaagccagtc | cctggtggga | gacattggaa | atgtgaacat | gtgggacttt | gtgctgtcac | 660 |
| cagatgagat | taacaccatc | tatcttggcg | ggcccttcag | tcctaatgtc | ctgaactggc | 720 |
| gggcactgaa | gtatgaagtg | caaggcgaag | tgttcaccaa | accccagctg | tggccctgag | 780 |
| gcccagctgt | gggtcctgaa | ggtacctccc | ggttttttac | accgcatggg | ccccacgtct | 840 |
| ctgtctctgg | tacctcccgc | ttttttacac | tgcatggttc | ccacgtctct | gtctctgggc | 900 |
| ctttgttccc | ctatatgcat | tgcaggcctg | ctccacccctc | ctcagcgcct | gagaatggag | 960 |
| gtaaagtgtc | tggtctggga | gctcgttaac | tatgctggga | acggtccaa  | agaatcaga  | 1020 |
| atttgaggtg | ttttgttttc | atttttattt | caagttggac | agatcttgga | gataatttct | 1080 |
| tacctcacat | agatgagaaa | actaacaccc | agaaaggaga | aatgatgtta | taaaaaactc | 1140 |
| ataaggcaag | agctgagaag | gaagcgctga | tcttctattt | aattccccac | ccatgacccc | 1200 |
| cagaaagcag | gagggcattg | cccacattca | cagggctctt | cagtctcaga | atcaggacac | 1260 |
| tggccaggtg | tctggtttgg | gtccagagtg | ctcatcatca | tgtcatagaa | ctgctgggcc | 1320 |
| caggtctcct | gaaatgggaa | gcccagcaat | accacgcagt | ccctccactt | tctcaaagca | 1380 |

```
cactggaaag gccattagaa ttgccccagc agagcagatc tgcttttttt ccagagcaaa    1440
atgaagcact aggtataaat atgttgttac tgccaagaac ttaaatgact ggttttttgtt   1500 tgcttgcagt gctttcttaa ttttatggct cttctgggaa actcctcccc ttttccacac    1560
gaaccttgtg gggctgtgaa ttcttttcttc atccccgcat tcccaatata cccaggccac   1620
aagagtggac gtgaaccaca gggtgtcctg tcagaggagc ccatctccca tctccccagc    1680
tccctatctg gaggatagtt ggatagttac gtgttcctag caggaccaac tacagtcttc    1740
ccaaggattg agttatggac tttgggagtg agacatcttc ttgctgctgg atttccaagc    1800
tgagaggacg tgaacctggg accaccagta gccatcttgt ttgccacatg gagagagact    1860
gtgaggacag aagccaaact ggaagtggag gagccaaggg attgacaaac aacagagcct    1920
tgaccacgtg gagtctctga atcagccttg tctggaacca gatctacacc tggactgccc    1980
aggtctataa gccaataaag ccctgtttta cttgaaaaaa aaaa                      2024
```

<210> SEQ ID NO 8
<211> LENGTH: 224
<212> TYPE: PRT
<213> ORGANISM: Homo sapiens

<400> SEQUENCE: 8

```
Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
    50                  55                  60

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
    130                 135                 140

Val Gly Ala Glu Ala Ser Ile Ile Leu Gly Gln Glu Gln Asp Ser Phe
145                 150                 155                 160

Gly Gly Asn Phe Glu Gly Ser Gln Ser Leu Val Gly Asp Ile Gly Asn
                165                 170                 175

Val Asn Met Trp Asp Phe Val Leu Ser Pro Asp Glu Ile Asn Thr Ile
            180                 185                 190

Tyr Leu Gly Gly Pro Phe Ser Pro Asn Val Leu Asn Trp Arg Ala Leu
        195                 200                 205

Lys Tyr Glu Val Gln Gly Glu Val Phe Thr Lys Pro Gln Leu Trp Pro
    210                 215                 220
```

<210> SEQ ID NO 9
<211> LENGTH: 428
<212> TYPE: DNA
<213> ORGANISM: Homo sapiens

<400> SEQUENCE: 9

```
atgtctcttg tcagctgtct ttcagaagac ctggtggggc aagtccgtgg gcatcatgtt    60
gaccgagctg gagaaagcct tgaactctat catcgacgtc taccacaagt actccctgat   120 aaagggaat tccatgccg tctacaggga tgacctgaag aaattgctag agaccgagtg   180
tcctcagtat atcaggaaaa agggtgcaga cgtctggttc aaagagttgg atatcaacac   240
tgatggtgca gttaacttcc aggagttcct cattctggtg ataaagatgg cgtggcagc   300 ccacaaaaaa agccatgaag aaagccacaa agagtagctg agttactggg cccagaggct   360
gggcccctgg acatgtacct gcagaataat aaagtcatca atacctcaaa aaaaaaaaa   420 aaaaaaaa                                                             428
```

<210> SEQ ID NO 10
<211> LENGTH: 93
<212> TYPE: PRT
<213> ORGANISM: Homo sapiens

<400> SEQUENCE: 10

```
Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90
```

<210> SEQ ID NO 11
<211> LENGTH: 586
<212> TYPE: DNA
<213> ORGANISM: Homo sapiens

<400> SEQUENCE: 11

```
aaacactctg tgtggctcct cggctttgac agagtgcaag acgatgactt gcaaaatgtc    60
gcagctggaa cgcaacatag agaccatcat caacaccttc caccaatact ctgtgaagct   120
ggggcaccca gacaccctga accaggggga attcaaagag ctggtgcgaa agatctgca   180 aaattttctc aagaaggaga ataagaatga aaaggtcata gaacacatca tggaggacct   240
ggacacaaat gcagacaagc agctgagctt cgaggagttc atcatgctga tggcgaggct   300
aacctgggcc tccacgagag agatgcacga gggtgacgag ggccctggcc accaccataa   360
gccaggcctc ggggagggca ccccctaaga ccacagtggc caagatcaca gtggccacgg   420
ccacggccac agtcatggtg ccacggcca gcccactaa tcaggaggcc aggccaccct   480
gcctctaccc aaccagggcc ccggggcctg ttatgtcaaa ctgtcttggc tgtggggcta   540
ggggctgggg ccaaataaag tctcttcctc caagtcaaaa aaaaaa                   586
```

<210> SEQ ID NO 12
<211> LENGTH: 114
<212> TYPE: PRT
<213> ORGANISM: Homo sapiens

<400> SEQUENCE: 12

```
Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His Lys Pro Gly Leu Gly Glu Gly
                100                 105                 110

Thr Pro
```

<210> SEQ ID NO 13
<211> LENGTH: 189
<212> TYPE: PRT
<213> ORGANISM: Homo sapiens

<400> SEQUENCE: 13

```
Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
                100                 105                 110

Pro Ser Leu Leu Pro Asp Ser Pro Val Gly Gln Leu His Ala Ser Leu
                115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

<210> SEQ ID NO 14
<211> LENGTH: 328
<212> TYPE: PRT
<213> ORGANISM: Homo sapiens

<400> SEQUENCE: 14

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
```

```
            20                  25                  30
Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
 50                  55                  60

Ser Ser Glu Val Leu Gly Ser Gly Lys Thr Leu Thr Ile Gln Val Lys
 65                  70                  75                  80

Glu Phe Gly Asp Ala Gly Gln Tyr Thr Cys His Lys Gly Gly Glu Val
                 85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
            130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
            195                 200                 205

Glu Val Met Val Asp Ala Val His Lys Leu Lys Tyr Glu Asn Tyr Thr
            210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
            275                 280                 285

Val Phe Thr Asp Lys Thr Ser Ala Thr Val Ile Cys Arg Lys Asn Ala
            290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 15
<211> LENGTH: 450
<212> TYPE: PRT
<213> ORGANISM: Homo sapiens

<400> SEQUENCE: 15

Gln Val Gln Leu Val Glu Ser Gly Gly Gly Val Val Gln Pro Gly Arg
 1                   5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Glu Tyr Tyr Ala Asp Ser Val
 50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Gly Tyr Thr Ser Ser Trp Tyr Pro Asp Ala Phe Asp
        100                 105                 110

Ile Trp Gly Gln Gly Thr Met Val Thr Val Ser Ser Ala Ser Thr Lys
    115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
        180                 185                 190

Val Thr Val Pro Ser Ser Asn Phe Gly Thr Gln Thr Tyr Thr Cys Asn
    195                 200                 205

Val Asp His Lys Pro Ser Asn Thr Lys Val Asp Lys Thr Val Glu Arg
210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Phe Asn Ser Thr Phe Arg
290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
            325                 330                 335

Lys Thr Ile Ser Lys Thr Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 16
<211> LENGTH: 217
<212> TYPE: PRT

<213> ORGANISM: Homo sapiens

<400> SEQUENCE: 16

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Thr Gly Ala Gly
            20                  25                  30

Tyr Asp Val His Trp Tyr Gln Gln Val Pro Gly Thr Ala Pro Lys Leu
        35                  40                  45

Leu Ile Tyr Gly Ser Gly Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Trp Val Phe Gly Gly Thr Arg Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 17
<211> LENGTH: 449
<212> TYPE: PRT
<213> ORGANISM: Homo sapiens

<400> SEQUENCE: 17

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45

Gly Ile Met Ser Pro Val Asp Ser Asp Ile Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly
            100                 105                 110

Thr Leu Val Thr Val Ser Ser Ser Thr Lys Gly Pro Ser Val Phe
        115                 120                 125

Pro Leu Ala Pro Ser Ser Lys Ser Thr Ser Gly Gly Thr Ala Ala Leu

```
                130             135             140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 18
<211> LENGTH: 214
<212> TYPE: PRT
<213> ORGANISM: Homo sapiens

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 451
<212> TYPE: PRT
<213> ORGANISM: Homo sapiens

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Ser Tyr
                20                  25                  30

Trp Met His Trp Val Arg Gln Ala Pro Gly Gln Arg Leu Glu Trp Ile
            35                  40                  45

Gly Glu Ile Asp Pro Ser Glu Ser Asn Thr Asn Tyr Asn Gln Lys Phe
        50                  55                  60

Lys Gly Arg Val Thr Leu Thr Val Asp Ile Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Gly Trp Asp Tyr Ala Ile Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

```
Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Ala Gly
225                 230                 235                 240

Ala Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 20
<211> LENGTH: 219
<212> TYPE: PRT
<213> ORGANISM: Homo sapiens

<400> SEQUENCE: 20

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Ala Lys Ser
            20                  25                  30

Tyr Gly Asn Thr Tyr Leu Ser Trp Tyr Leu Gln Lys Pro Gly Gln Ser
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                85                  90                  95

Thr His Gln Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125
```

```
Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 21
<211> LENGTH: 451
<212> TYPE: PRT
<213> ORGANISM: Homo sapiens

<400> SEQUENCE: 21

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Val Tyr Val Asp Gly Val Glu Val
```

```
                275                 280                 285
His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
        450

<210> SEQ ID NO 22
<211> LENGTH: 214
<212> TYPE: PRT
<213> ORGANISM: Homo sapiens

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 23
<211> LENGTH: 229
<212> TYPE: PRT
<213> ORGANISM: Homo sapiens

<400> SEQUENCE: 23

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala
225
```

<210> SEQ ID NO 24
<211> LENGTH: 214
<212> TYPE: PRT
<213> ORGANISM: Homo sapiens

<400> SEQUENCE: 24

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ile Tyr Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 445
<212> TYPE: PRT
<213> ORGANISM: Homo sapiens

<400> SEQUENCE: 25

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                 90                  95

Lys Thr His Gly Ser His Asp Asn Trp Gly Gln Gly Thr Met Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220
```

```
Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 26
<211> LENGTH: 217
<212> TYPE: PRT
<213> ORGANISM: Homo sapiens

<400> SEQUENCE: 26

Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Tyr Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Ser Arg Tyr Thr
                85                  90                  95

His Pro Ala Leu Leu Phe Gly Thr Gly Thr Lys Val Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
```

```
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Cys Ser
                210                 215

<210> SEQ ID NO 27
<211> LENGTH: 446
<212> TYPE: PRT
<213> ORGANISM: Homo sapiens

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ile Thr Tyr
                20                  25                  30

Trp Met Thr Trp Val Arg Gln Ala Pro Gly Gln Gly Leu Glu Trp Met
            35                  40                  45

Gly Gln Ile Phe Pro Ala Ser Gly Ser Ala Asp Tyr Asn Glu Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Gly Gly Phe Ala Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300
```

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 28
<211> LENGTH: 214
<212> TYPE: PRT
<213> ORGANISM: Homo sapiens

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Ile Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29

<211> LENGTH: 446
<212> TYPE: PRT
<213> ORGANISM: Homo sapiens

<400> SEQUENCE: 29

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Phe Ile Thr Asn Asn
            20                  25                  30

Tyr Trp Gly Trp Val Arg Gln Ala Pro Gly Lys Gly Leu Glu Trp Val
        35                  40                  45

Gly Tyr Ile Ser Tyr Ser Gly Ser Thr Ser Tyr Asn Pro Ser Leu Lys
    50                  55                  60

Ser Arg Phe Thr Ile Ser Arg Asp Thr Ser Lys Asn Thr Phe Tyr Leu
65                  70                  75                  80

Gln Met Asn Ser Leu Arg Ala Glu Asp Thr Ala Val Tyr Tyr Cys Ala
                85                  90                  95

Arg Thr Gly Ser Ser Gly Tyr Phe Asp Phe Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
```

```
                385                 390                 395                 400
Asp Gly Ser Phe Phe Leu Tyr Ser Lys Leu Thr Val Asp Lys Ser Arg
                    405                 410                 415
Trp Gln Gln Gly Asn Val Phe Ser Cys Ser Val Met His Glu Ala Leu
                    420                 425                 430
His Asn His Tyr Thr Gln Lys Ser Leu Ser Leu Ser Pro Gly
                    435                 440                 445

<210> SEQ ID NO 30
<211> LENGTH: 214
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
1               5                   10                  15
Asp Arg Val Thr Ile Thr Cys Arg Ala Ser Glu Ser Val Asp Asp Leu
            20                  25                  30
Leu His Trp Tyr Gln Gln Lys Pro Gly Lys Ala Pro Lys Leu Leu Ile
        35                  40                  45
Lys Tyr Ala Ser Gln Ser Ile Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Asn Ser Leu Pro Asn
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 31
<211> LENGTH: 5
<212> TYPE: PRT
<213> ORGANISM: Homo sapiens

<400> SEQUENCE: 31

Ser Tyr Gly Met His
1               5

<210> SEQ ID NO 32
<211> LENGTH: 17
<212> TYPE: PRT
<213> ORGANISM: Homo sapiens

<400> SEQUENCE: 32
```

```
Val Ile Trp Tyr Asp Gly Ser Asn Glu Tyr Tyr Ala Asp Ser Val Lys
1               5                   10                  15

Gly
```

<210> SEQ ID NO 33
<211> LENGTH: 15
<212> TYPE: PRT
<213> ORGANISM: Homo sapiens

<400> SEQUENCE: 33

```
Asp Arg Gly Tyr Thr Ser Ser Trp Tyr Pro Asp Ala Phe Asp Ile
1               5                   10                  15
```

<210> SEQ ID NO 34
<211> LENGTH: 14
<212> TYPE: PRT
<213> ORGANISM: Homo sapiens

<400> SEQUENCE: 34

```
Thr Gly Ser Ser Ser Asn Thr Gly Ala Gly Tyr Asp Val His
1               5                   10
```

<210> SEQ ID NO 35
<211> LENGTH: 7
<212> TYPE: PRT
<213> ORGANISM: Homo sapiens

<400> SEQUENCE: 35

```
Gly Ser Gly Asn Arg Pro Ser
1               5
```

<210> SEQ ID NO 36
<211> LENGTH: 11
<212> TYPE: PRT
<213> ORGANISM: Homo sapiens

<400> SEQUENCE: 36

```
Gln Ser Tyr Asp Ser Ser Leu Ser Gly Trp Val
1               5                   10
```

<210> SEQ ID NO 37
<211> LENGTH: 6
<212> TYPE: PRT
<213> ORGANISM: Homo sapiens

<400> SEQUENCE: 37

```
Asp Gln Cys Ile Asp Gly
1               5
```

<210> SEQ ID NO 38
<211> LENGTH: 6
<212> TYPE: PRT
<213> ORGANISM: Homo sapiens

<400> SEQUENCE: 38

```
Gly Asn Gly Gln Ser Gly
1               5
```

<210> SEQ ID NO 39
<211> LENGTH: 16
<212> TYPE: PRT
<213> ORGANISM: Homo sapiens

<400> SEQUENCE: 39

-continued

Tyr Ser Ile Phe Ser Tyr Ala Thr Lys Arg Gln Asp Asn Glu Ile Leu
1               5                   10                  15

<210> SEQ ID NO 40
<211> LENGTH: 16
<212> TYPE: PRT
<213> ORGANISM: Homo sapiens

<400> SEQUENCE: 40

Thr Val Phe Ser Arg Met Pro Pro Arg Asp Lys Thr Met Arg Phe Phe
1               5                   10                  15

<210> SEQ ID NO 41
<211> LENGTH: 14
<212> TYPE: PRT
<213> ORGANISM: Homo sapiens

<400> SEQUENCE: 41

Val Ala Ala His Lys Lys Ser His Glu Ser His Lys Glu
1               5                   10

<210> SEQ ID NO 42
<211> LENGTH: 15
<212> TYPE: PRT
<213> ORGANISM: Homo sapiens

<400> SEQUENCE: 42

Trp Gln Pro Thr Lys Lys Ala Met Lys Lys Ala Thr Lys Ser Ser
1               5                   10                  15

<210> SEQ ID NO 43
<211> LENGTH: 120
<212> TYPE: PRT
<213> ORGANISM: Homo sapiens

<400> SEQUENCE: 43

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly His Ile His Tyr Ser Gly Asn Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Lys Asn Arg Gly Phe Tyr Tyr Gly Met Asp Val Trp Gly Gln
            100                 105                 110

Gly Thr Thr Val Thr Val Ser Ser
        115                 120

<210> SEQ ID NO 44
<211> LENGTH: 107
<212> TYPE: PRT
<213> ORGANISM: Homo sapiens

<400> SEQUENCE: 44

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Val Ile Ser Ser Trp
                20                  25                  30

Leu Ala Trp Tyr Gln Gln Lys Pro Gly Lys Ala Pro Ser Leu Leu Ile
             35                  40                  45

Tyr Ala Ala Ser Ser Leu Gln Ser Gly Val Pro Ser Arg Phe Ser Gly
 50                  55                  60

Ser Val Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Phe
                 85                  90                  95

Thr Phe Gly Pro Gly Thr Lys Val Asp Phe Lys
                100                 105

<210> SEQ ID NO 45
<211> LENGTH: 7
<212> TYPE: PRT
<213> ORGANISM: Homo sapiens

<400> SEQUENCE: 45

Ser Gly Gly Tyr Tyr Trp Ser
1               5

<210> SEQ ID NO 46
<211> LENGTH: 16
<212> TYPE: PRT
<213> ORGANISM: Homo sapiens

<400> SEQUENCE: 46

His Ile His Tyr Ser Gly Asn Thr Tyr Tyr Asn Pro Ser Leu Lys Ser
1               5                   10                  15

<210> SEQ ID NO 47
<211> LENGTH: 10
<212> TYPE: PRT
<213> ORGANISM: Homo sapiens

<400> SEQUENCE: 47

Asn Arg Gly Phe Tyr Tyr Gly Met Asp Val
1               5                   10

<210> SEQ ID NO 48
<211> LENGTH: 11
<212> TYPE: PRT
<213> ORGANISM: Homo sapiens

<400> SEQUENCE: 48

Arg Ala Ser Gln Val Ile Ser Ser Trp Leu Ala
1               5                   10

<210> SEQ ID NO 49
<211> LENGTH: 7
<212> TYPE: PRT
<213> ORGANISM: Homo sapiens

<400> SEQUENCE: 49

Ala Ala Ser Ser Leu Gln Ser
1               5

<210> SEQ ID NO 50
<211> LENGTH: 9
<212> TYPE: PRT

```
<400> SEQUENCE: 50

Gln Gln Ala Asn Ser Phe Pro Phe Thr
1               5
```

PREDICTION OF CLINICAL RESPONSE TO IL23-ANTAGONISTS USING IL23 PATHWAY BIOMARKERS

CROSS-REFERENCE TO RELATED APPLICATIONS

This application is the U.S. national phase of PCT/US2016/52060, filed Sep. 16, 2016, which claims the priority benefit of provisional U.S. patent application No. 62/220,062, filed Sep. 17, 2015, each incorporated herein by reference in its entirety.

REFERENCE TO SEQUENCE LISTING SUBMITTED ELECTRONICALLY

The content of the electronically submitted sequence listing in ASCII text file Name X49653US_Seqlisting.txt; Size: 70,895 bytes; and Date of Creation: Jun. 16, 2017) filed with the application is incorporated herein by reference in its entirety.

FIELD

The present disclosure relates to the use of IL23 pathway biomarkers, e.g., interleukin-22, lipocalin-2, and combinations thereof, to stratify and/or identify populations of patients having an IL23-mediated disease or disorder suitable for treatment with an IL23 antagonist (including, e.g., an anti-IL23 antibody or fragment thereof).

BACKGROUND

Interleukin (IL)-23 is a proinflammatory cytokine implicated in the pathogenesis of various inflammatory conditions including but not limited to Crohn's disease (CD), ulcerative colitis (UC), psoriasis, psoriatic arthritis, rheumatoid arthritis, and ankylosing spondylitis. IL23 induces T-cells to express a number of inflammatory genes including IL17A, IL17A receptor, TNF-α, and GM-CSF. The main known effects of IL23 are to drive the differentiation of T helper Th17 cells, as well as macrophages, natural killer (NK) cells, dendritic cells, and innate lymphoid cells leading to up-regulation of IL17, IL22, TNFα, GMCSF, and IFN-γ, and down-regulation of IL10.

Interleukin (IL)-23 is a heterodimeric cytokine consisting of 2 subunits: p40 and p19. The p40 subunit is shared by IL12 and IL23 as a common subunit, and is targeted by inhibitors of IL12/23, e.g., ustekinumab/STELARA® (Janssen Biotech, Inc, Horsham, Pa.) and briakinumab/ABT-874 (Abbott Laboratories, Abbott Park, Ill.).

Studies in patients have demonstrated that IL23 is upregulated in cells and target tissues of Crohn's disease (CD) and ulcerative colitis (UC), while IL12 is not (Schmidt et al. Inflamm Bowel Dis. 11(1):16-23 (2005)). Similar observations have been reported in dendritic cells from patients with multiple sclerosis (MS; Vaknin et al. J of Immunol. 176: 7768 74 (2006)), patients with psoriasis (Lee et al J Exp Med 199:125-30 (2004)), and active lesions from patients with MS (Li et al. Brain. 130(2):490-501 (2007)). IL23 is also elevated in other diseases including rheumatoid arthritis (RA), ankylosing spondylitis (AS), chronic obstructive pulmonary disease (COPD), and neuromyelitis optica. Genome-wide association studies in CD and psoriasis (PsO) patients showed significant association between polymorphisms in the unique IL23 receptor component (IL23R) and disease (Cargill et al. Am J of Human Gen. 80:273-90 (2007); Duerr et al. Science 314:1461-63 (2006)). Furthermore, allelic variants of IL23R have shown significant correlation with the frequency of UC (Cargill et al. Am. J. Hum. Gen. 80:273-90 (2007)), RA (Farago et al. Ann. Rheum. Dis. 67:248-50 (2008)), AS (Burton et al. Nature Gen. 39:1329-37 (2007)), and MS (Illes et al. Neuro Letters. 431:36-38 (2008)). Therefore, both IL23 and its receptor are very attractive targets for drug development.

In preclinical models of inflammatory bowel disease (IBD) (Ahern et al. Immun Rev. 226:147-59 (2008)), PsO inflammatory arthritis (Yago et al. Arthritis Res and Ther. 9:R96 (2007)), and MS (Cua et al. Nature 421:744-48 (2003), the beneficial effects of anti-IL12/23p40 antibodies have been recapitulated through the blockade of IL23 alone while sparing IL12. In the clinic, anti-IL12/23p40 antibodies (e.g., ustekinumab and briakinumab) have been shown to induce clinical responses in CD (Phase 2 studies; Toedter et al. Am J Gastroenterol. 104(11):2768-73 (2009); Sandborn et al. Gastroenterol. 135:1130-41 (2008); Mannon et al. N Eng J of Med. 351(20):2069-79 (2004)) and PsO (Phase 2 and 3 studies; Gordon et al. J. Invest. Dermatol. 132:304-314 (2012); Kimball et al. Br J Dermatol. 167(Suppl. 1):64 (Abstract P94) (2012); Langley et al. J Am Acad Dermatol. 66:AB195 (Abstract 4779) (2012); Gottlieb et al. Br. J. Dermatol. 165:652-660 (2011); Reich et al. N Engl J Med. 365:1586-1596 (2011); Strober et al. Br J Dermatol. 165: 661-668 (2011); Leonardi et al. Lancet. 371(9625):1665-74 (2008); Papp et al. Lancet. 371(9625):1675-84 (2008)). Phase 1 clinical studies with anti-IL23 antibodies MEDI2070 (NCT01094093) and CNTO 1959 (Sofen et al. Drugs Dermatol. 10(8):885-92 (2011)) in subjects with PsO have demonstrated clinical efficacy comparable with antibodies targeting IL12 and IL23 indicating that therapeutic effects of the anti-IL12/23p40 antibodies may be due to neutralization of IL23 alone.

Although several agents targeting different elements of the IL23 pathway are currently approved or under development, the morbidity, complications and intrinsic heterogeneity of IL23-mediated diseases continue to demand new therapies and/or improved methods of identifying specific populations of patients suitable for treatment with IL23 antagonists. See, e.g., Gaffe et al. Nature Revs. Immunol. 14:585-600 (2014).

BRIEF SUMMARY

The present disclosure provides a method of treating an interleukin-23 (IL23)-mediated disease in a patient, comprising administering an IL23 antagonist to a patient if the patient is determined or identified to have (i) a higher or increased level of interleukin-22 (IL22) and/or (ii) a higher or increased level of lipocalin 2 (LCN2) in one or more samples taken from the patient compared to a predetermined IL22 and/or LCN2 threshold level, or compared to a IL22 and/or LCN2 level in one or more control samples.

Also provided is method of treating a patient having an IL23-mediated disease comprising suspending or not initiating the administration of an IL23 antagonist to a patient if the patient is determined or identified to have (i) a lower or decreased level of interleukin-22 (IL22) and/or (ii) a lower or decreased level of lipocalin 2 (LCN2) in one or more samples taken from the patient compared to a predetermined IL22 and/or LCN2 threshold level, or compared to a IL22 and/or LCN2 level in one or more control samples.

Also provided is a method of treating an interleukin-23 (IL23)-mediated disease in a patient, wherein the patient failed, was non-responsive, or was intolerant to treatment with an anti-TNF agent comprising administering an IL23 antagonist to the patient if the patient is determined or identified to have (i) a higher or increased level of interleukin-22 (IL22) and/or (ii) a higher or increased level of lipocalin 2 (LCN2) one or more samples taken from the patient compared to a predetermined IL22 and/or LCN2 threshold level, or compared to a IL22 and/or LCN2 level in one or more control samples.

The disclosure also provides a method of determining whether to treat a patient having an IL23-mediated disease with an IL23 antagonist, comprising determining to treat the patient if the patient is determined or identified to have (i) a higher or increased level of interleukin-22 (IL22) and/or (ii) a higher or increased level of lipocalin 2 (LCN2) in one or more samples taken from the patient compared to a predetermined IL22 and/or LCN2 threshold level, or compared to a IL22 and/or LCN2 level in one or more control samples.

In addition, the disclosure provides a method of selecting a patient diagnosed with an IL23-mediated disease as a candidate for treatment with an IL23 antagonist, comprising selecting the patient for treatment if the patient is determined or identified to have (i) a higher or increased level of interleukin-22 (IL22) and/or (ii) a higher or increased level of lipocalin 2 (LCN2) in one or more samples taken from the patient compared to a predetermined IL22 and/or LCN2 threshold level, or compared to a IL22 and/or LCN2 level in one or more control samples.

In some aspects, the methods disclosed herein further comprise measuring the level of IL22 and/or LCN2 in one or more of the samples obtained from the patient or instructing a clinical laboratory or healthcare provider to measure the level of IL22 and/or LCN2 in the sample and/or submitting the one or more samples obtained from the patient to a clinical laboratory or healthcare provider to measure the level of IL22 and/or LCN2 in the sample.

In some aspects, the methods disclosed herein further comprise determining the level of IL22 and/or LCN2 in the one or more samples obtained from the patient.

In some aspects, the methods disclosed herein further comprise advising a healthcare provider to administer an IL23 antagonist to the patient if the patient is determined or identified to have (i) a higher or increased level of IL22 and/or (ii) a higher or increased level of LCN2 in one or more of the samples compared to a predetermined IL22 and/or LCN2 threshold level, or compared to a IL22 and/or LCN2 level in one or more control samples, or to suspend or deny the administration of an IL23 antagonist to the patient if the patient is determined or identified to have (i) a lower or decreased level of IL22 and/or (ii) a lower or decreased level of LCN2 in one or more of the samples compared to a predetermined IL22 and/or LCN2 threshold level, or compared to a IL22 and/or LCN2 level in one or more control samples.

The present disclosure also provides a method of measuring the efficacy or pharmacodynamics of an IL23 antagonist in a patient diagnosed with an IL23-mediated disease, comprising: (a) measuring the level of IL22 and/or LCN2 in a first sample taken from the patient; (b) administering an IL23 antagonist; and (c) measuring the level of IL22 and/or LCN2 in a second sample taken from the patient, wherein a reduction in the level of IL22 and/or LCN2 in the second sample compared to the patient's level IL22 and/or LCN2 in the first sample indicates that the patient is responding to treatment. In some aspects, the second sample is taken 1, 2, 4, 8, 12, or 28 weeks, or at intervening times, after administering the IL23 antagonist.

In some aspects, the IL23 antagonist is an anti-IL23 antibody or antigen-binding fragment thereof. In some aspects, the anti-IL23 antibody or antigen-binding fragment thereof binds to the p19 subunit of IL23 (SEQ ID NO: 13), to the p40 subunit of IL23 (SEQ ID NO: 14), or both. In some aspects, the anti-IL23 antibody or antigen-binding fragment thereof comprises ustekinumab, briakinumab, guselkumab, BI-655066, tildrakinumab, LY-3074828, or an antigen-binding fragment thereof. In some aspects, the anti-IL23 antibody or antigen-binding fragment thereof comprises the variable region (VH) (SEQ ID NO: 5) and/or the light chain variable region (VL) (SEQ ID NO: 6) of MEDI2070. In some aspects, the anti-IL23 antibody or antigen-binding fragment thereof comprises at least one of the complementarity determining regions of MEDI2070 (SEQ ID NOS: 31-36). In some aspects, the antibody is administered at a fixed dose. In some aspects, the fixed dose is between 10 and 1000 mg/dose. In some aspects, the fixed dose is about 210 mg/dose or about 700 mg/dose.

In some aspects, the patient has been treated before, during, after, or alternatively to the administration of an IL23 antagonist or anti-IL23 antibody or antigen-binding fragment with one or more additional therapies for the treatment of the IL23-mediated disease or disorder. In some aspects, the one or more samples taken from the patient and/or the one or more control samples are one or more samples selected from the group consisting of: whole blood, blood serum, plasma, saliva, sputum, bronchoalveolar lavage fluid, cerebrospinal fluid, pleural fluid, pericardial fluid, ascites, synovial fluid, epithelial cells, urine, stool, skin, tissue biopsy, or a combination thereof. In some aspects, the one or more control samples are (i) a sample or samples obtained from normal healthy individuals; (ii) a sample or samples obtained from patients with a non-IL23-mediated disease; or (iii) a combination thereof. In some aspects, the patient's level of IL22 and/or LCN2 is measured in an immunoassay described in Example 3.

In some aspects, the methods disclosed above further comprise determining the level of one or more IL23 pathway biomarkers selected from the group consisting of IL17F, IL17A/F, IL23R, IL12B, IL6, IL21, TNF, CCR6, CCL22, IL1R1, IFNγ, S100A12, DEFB-2, DEFB-4, IL1, SERPINB3, PI3/Elafin, LL37, RORγ, RORγT, IL26, S100A7, DEFB103B, and GM-CSF.

In some aspects, the predetermined threshold level of IL22 and/or LCN2 is selected from the group consisting of: (a) about the mean level of IL22 and/or LCN2; (b) about the median level of IL22 and/or LCN2; and (c) about the $1^{st}$, $2^{nd}$, $3^{rd}$, $4^{th}$, $5^{th}$, $6^{th}$, $7^{th}$, $8^{th}$, or $9^{th}$ decile baseline level of IL22 and/or LCN2 as described in FIG. 6 or TABLES 4 or 5 in Example 4; as measured in the serum using an immunoassay from a plurality of (i) normal healthy patients, (ii) patients with a non-IL23-mediated disease, or (iii) patients with an IL23-mediated disease.

In some aspects, the IL23-mediated disease or disorder is a pulmonary disease, an inflammatory bowel disease, a chronic inflammatory skin disease, an inflammatory disease, an autoimmune disease, a neurodegenerative disease, or a cancer. In some aspects, the IL23-mediated disease or disorder is selected from the group consisting of: asthma, IPF, COPD. Crohn's disease, ulcerative colitis (UC), celiac disease, atopic dermatitis, allergic contact dermatitis, eczema, psoriasis, alopecia areata, palmoplantar pustulosis, psoriatic arthritis, anklyosing spondylitis, arthritis, rheumatoid arthritis (RA), a rheumatic disorder, ANCA vasculitis, Bechet's disease, autoimmune thyroiditis, type 1 diabetes, multiple sclerosis (MS), Sjogren's syndrome (SS), systemic lupus erythematosus (SLE), Alzheimer's disease, gastric cancer, colorectal cancer, esophageal cancer, leukemia, hepatitis B virus (HBV)-related hepatocellular carcinoma, breast cancer, lung cancer, and nasopharyngeal cancer. In some aspects, the inflammatory bowel disease is Crohn's disease, UC or Celiac Disease.

In some aspects, the patient is determined to have a high level of CRP≥5 mg/L and/or a high level of FCP≥250 µg/g, a high level of FCP≥200 µg/g, a high level of FCP≥150 µg/g, a high level of FCP≥100 µg/g, or a high level of FCP at least about 100 µg/g to at least about 250 µg/g in one or more samples taken from the patient. In some aspects, (a) the predetermined IL22 threshold level is at least about 7.9 pg/mL to at least about 31.4 pg/mL as measured using an immunoassay; and/or, (b) the predetermined LCN2 threshold level is at least about 143 ng/mL to at least about 261 ng/mL as measured using an immunoassay. In some aspects, (a) the predetermined IL22 threshold level is about 15.6 pg/mL as measured using an immunoassay; and/or, (b) the predetermined LCN2 threshold level is about 215 ng/mL as measured using an immunoassay. In some aspects, the patient is determined to have (a) a level of CRP≥5 mg/L and/or a level of FCP≥250 µg/g, a level of FCP≥200 µg/g, a level of FCP≥150 µg/g, a level of FCP≥100 µg/g, or a level of FCP at least about 100 µg/g to at least about 250 µg/g; (b) (i) the predetermined IL22 threshold level is at least about 7.9 pg/mL to at least about 31.4 pg/mL as measured using an immunoassay; and/or, (ii) the predetermined LCN2 threshold level is at least about 143 ng/mL to at least about 261 ng/mL as measured using an immunoassay; and/or (c) (i) the predetermined IL22 threshold level is about 15.6 pg/mL as measured using an immunoassay; and/or, (ii) the predetermined LCN2 threshold level is about 215 ng/mL as measured using an immunoassay; in one or more samples taken from the patient.

In some aspects, administration of the IL23 antagonist or anti-IL23 antibody or antigen-binding fragment thereof results in a Crohn's Disease Activity Index (CDAI) response score reduction of at least 100 points after first administering the anti-IL23 antibody or antigen-binding fragment thereof and/or a reduction of the total CDAI score to below 150 points after first administering the anti-IL23 antibody or antigen-binding fragment thereof. In some aspects, the CDAI response score reduction of at least 100 points, or reduction of the total CDAI score to below 150 points occurs within 1, 2, 4, 8, 12, 16 or 24 weeks or later after first administering the IL23 antagonist or anti-IL23 antibody or antigen-binding fragment thereof.

BRIEF DESCRIPTION OF THE DRAWINGS/FIGURES

FIG. 1 shows patient disposition up to Week 24. The chart summarizes the number and disposition of enrolled and randomized patients in a phase 2a study (clinicaltrials.gov identifier: NCT01714726) evaluating MEDI2070 in patients having moderate or severe CD. mITT, Modified Intent-to-Treat Population; PP, per protocol; OL, Open Label.

Figure 2A:
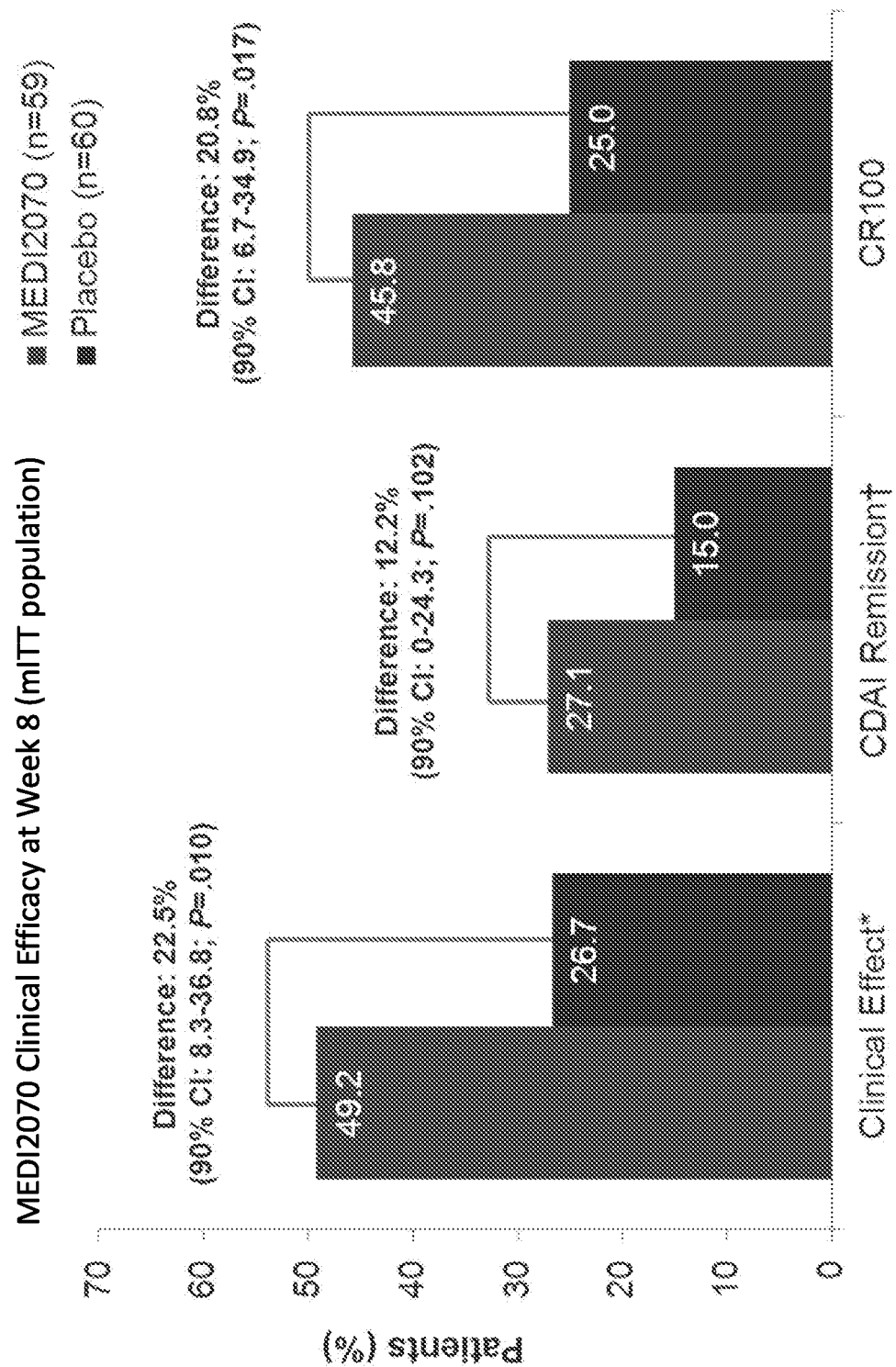

FIG. 2A shows clinical efficacy at Week 8 in the Modified Intent-to-Treat Population as indicated by CDAI clinical effect, CDAI remission, and CR100. The rate of CDAI clinical effect (defined as a CDAI score less than 150 or reduction from baseline in CDAI score of at least 100 points) at week 8 was significantly higher in the MEDI2070 group versus the placebo group (49.2% vs. 26.7%, respectively; P=0.01). CDAI remission (defined as a CDAI score less than 150) rates were 27.1% with MEDI2070 and 15.0% with placebo (P=0.10). CR100 rates (defined as at least a 100-point CDAI score reduction) were 45.8% and 25.0% in the MEDI2070 and placebo groups, respectively (P=0.02).

Figure 2B:
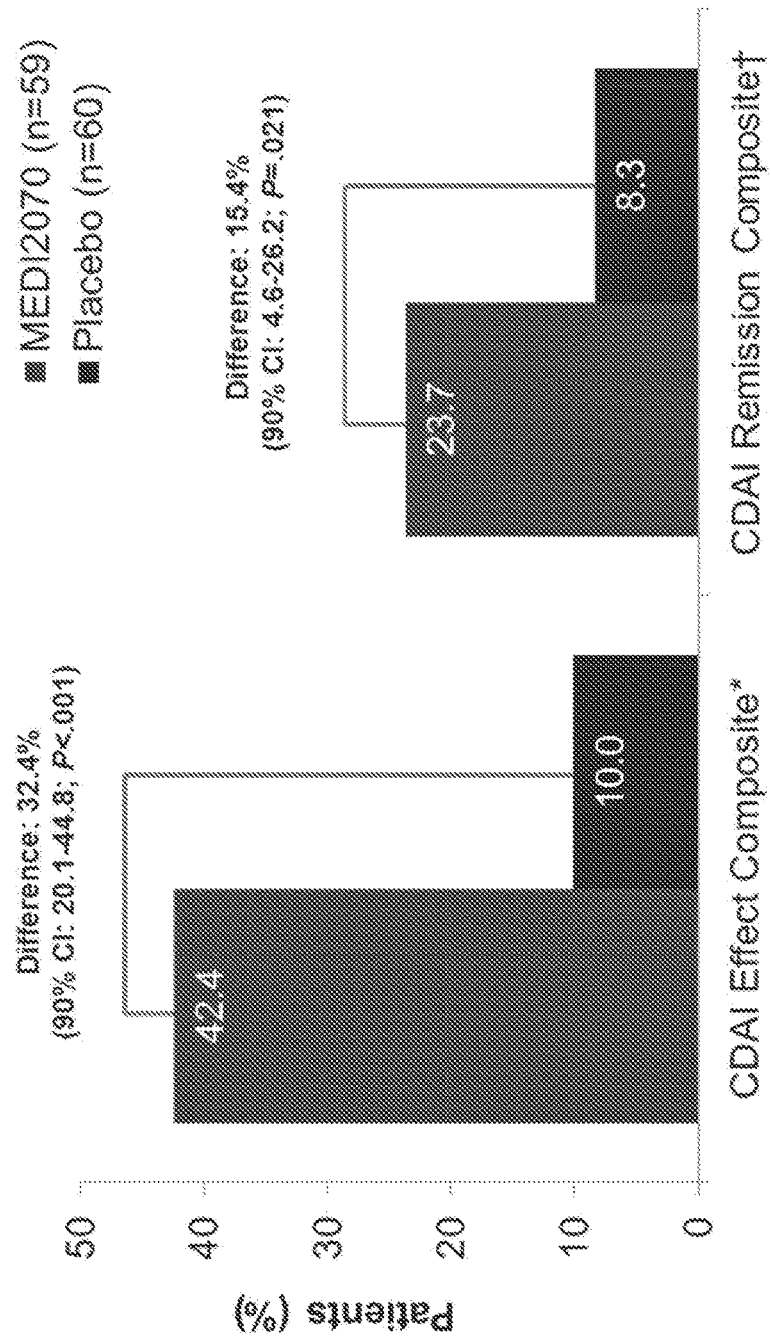

FIG. 2B shows clinical efficacy at Week 8 in the Modified Intent-to-Treat Population as indicated by composite end points. A significantly greater proportion of patients receiving MEDI2070 achieved the composite end points of CDAI effect and 50% reduction in FCP or CRP versus baseline (P<0.001), and CDAI remission and 50% reduction in FCP or CRP versus baseline (P=0.02). CDAI, Crohn's Disease Activity Index; CI, confidence interval; CRP, C-reactive protein; FCP, fecal calprotectin; p, p-value.

Figure 3A:
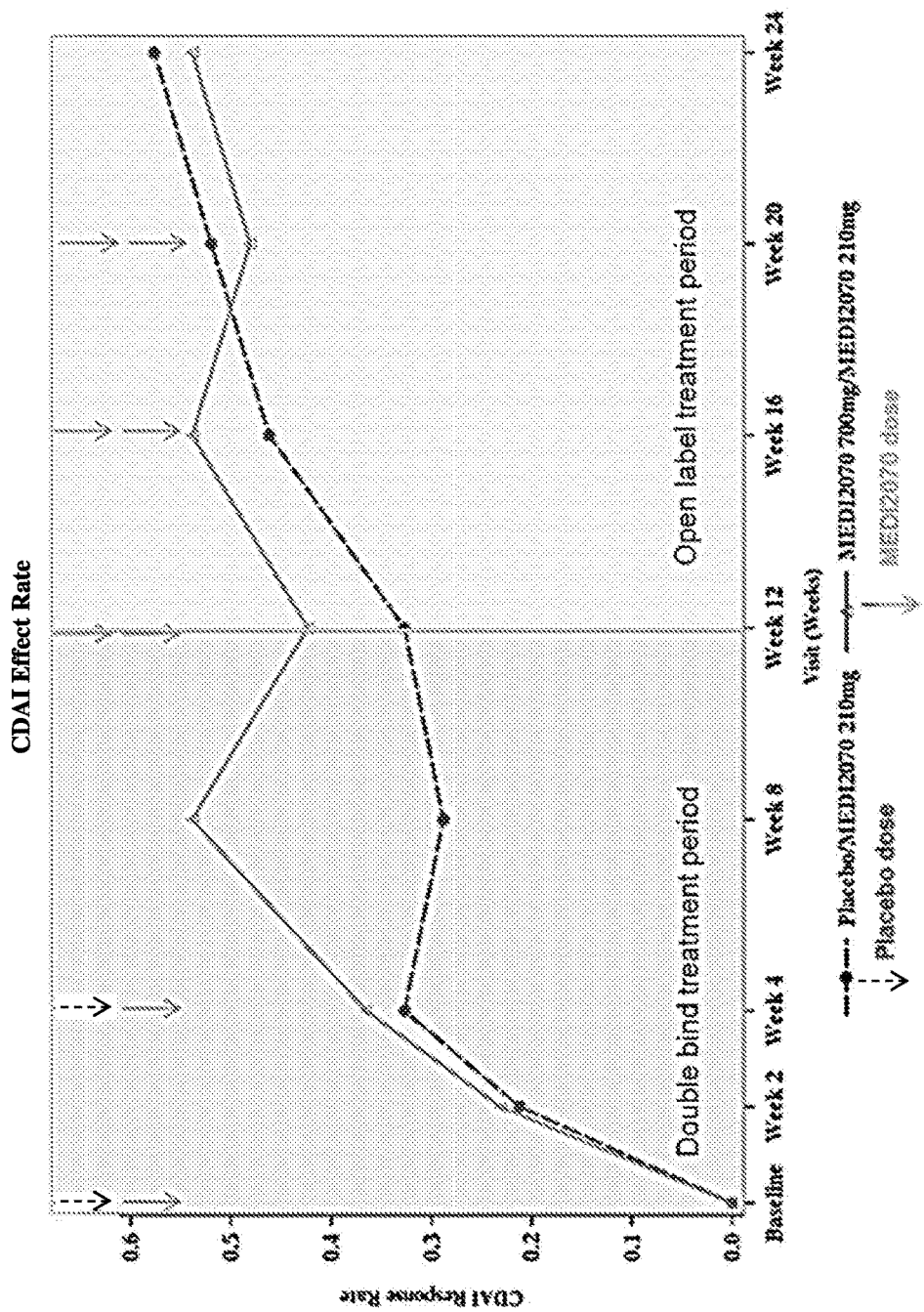

FIG. 3A shows efficacy at various time points through Week 24 in the Open-Label Population using nonresponder imputation as indicated by Crohn's Disease Activity Index effect rate (from baseline to week 24). Sample size of open-label period: placebo/MEDI2070 group (n=52); MEDI2070 group (n=52).

Figure 3B:
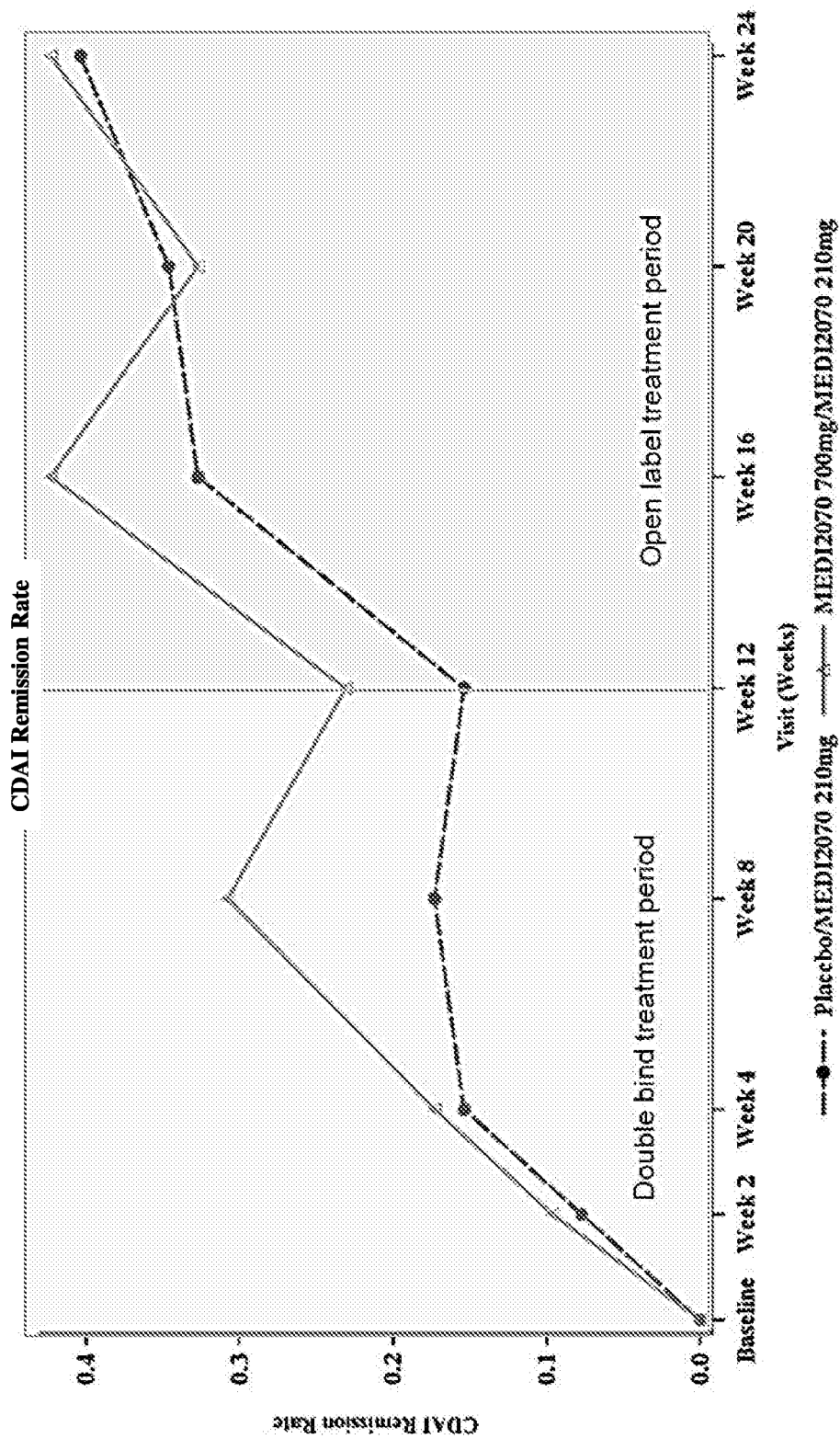

FIG. 3B shows efficacy at various time points through Week 24 in the open-label population using nonresponder imputation as indicated by Crohn's Disease Activity Index remission rate (from baseline to week 24). Sample size of open-label period: placebo/MEDI2070 group (n=52); MEDI2070 group (n=52).

Figure 4:
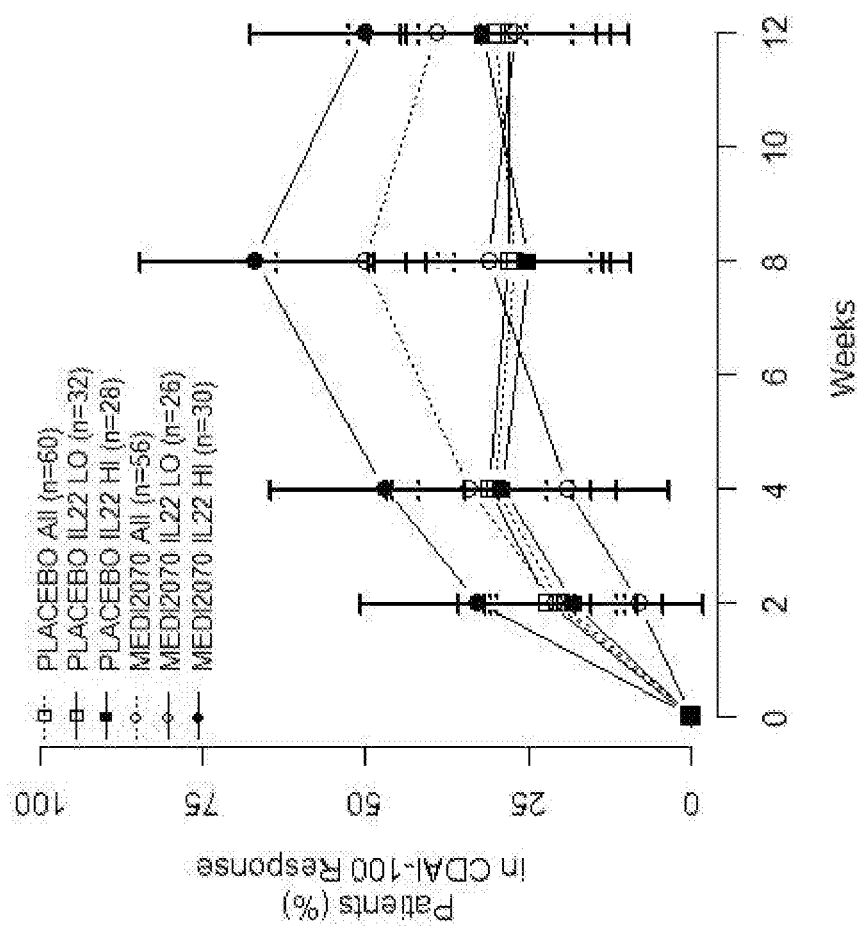

FIG. 4 shows percent of patients with CDAI-100 response over time by baseline IL22 levels. IL22 LO, baseline IL22<15.6 pg/mL; IL22 HI, baseline IL22≥15.6 pg/mL. CI, confidence interval. Median IL22 concentration across study population: 15.6 pg/mL. 116 patients had evaluable baseline IL22 values. Patients with baseline serum IL22 levels≥15.6 µg/mL had a statistically significant increased CDAI-100 response compared to placebo at week 8.

Figure 5:
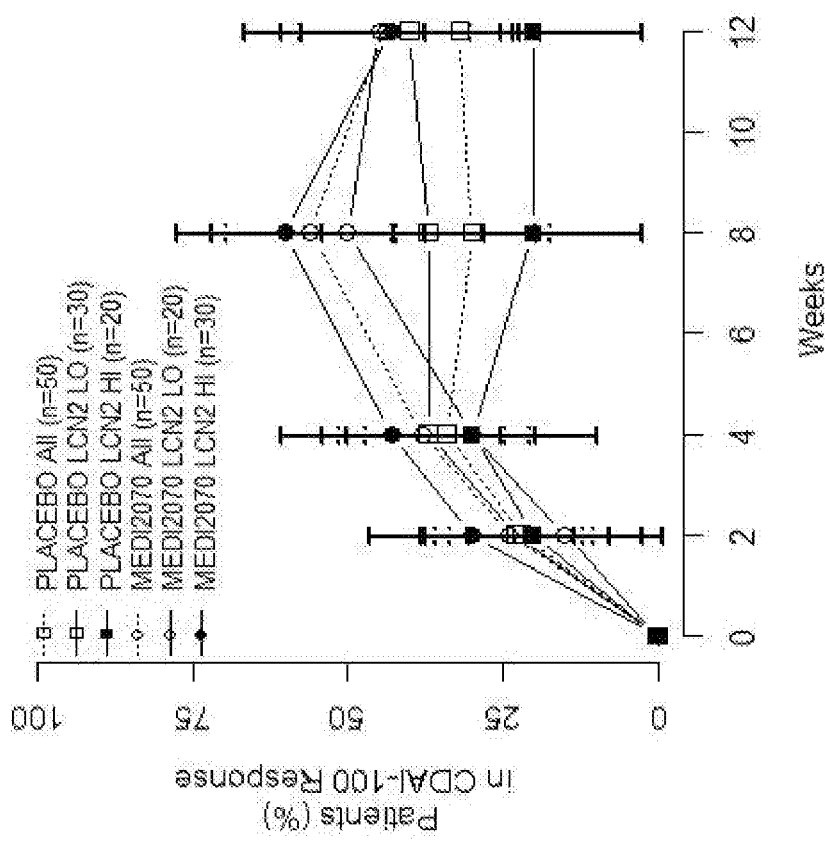

FIG. 5 shows percent of patients with CDAI-100 response over time by baseline LCN2 Levels. LCN2 LO, baseline LCN2<215 ng/mL; LCN2 HI, baseline LCN2≥215 ng/mL. CI, confidence interval. Median LCN2 concentration across study population: 215 ng/mL. Patients with baseline serum LCN2 levels ≥215 ng/mL had a statistically significant increased CDAI-100 response compared to placebo at week 8.

Figure 6B:
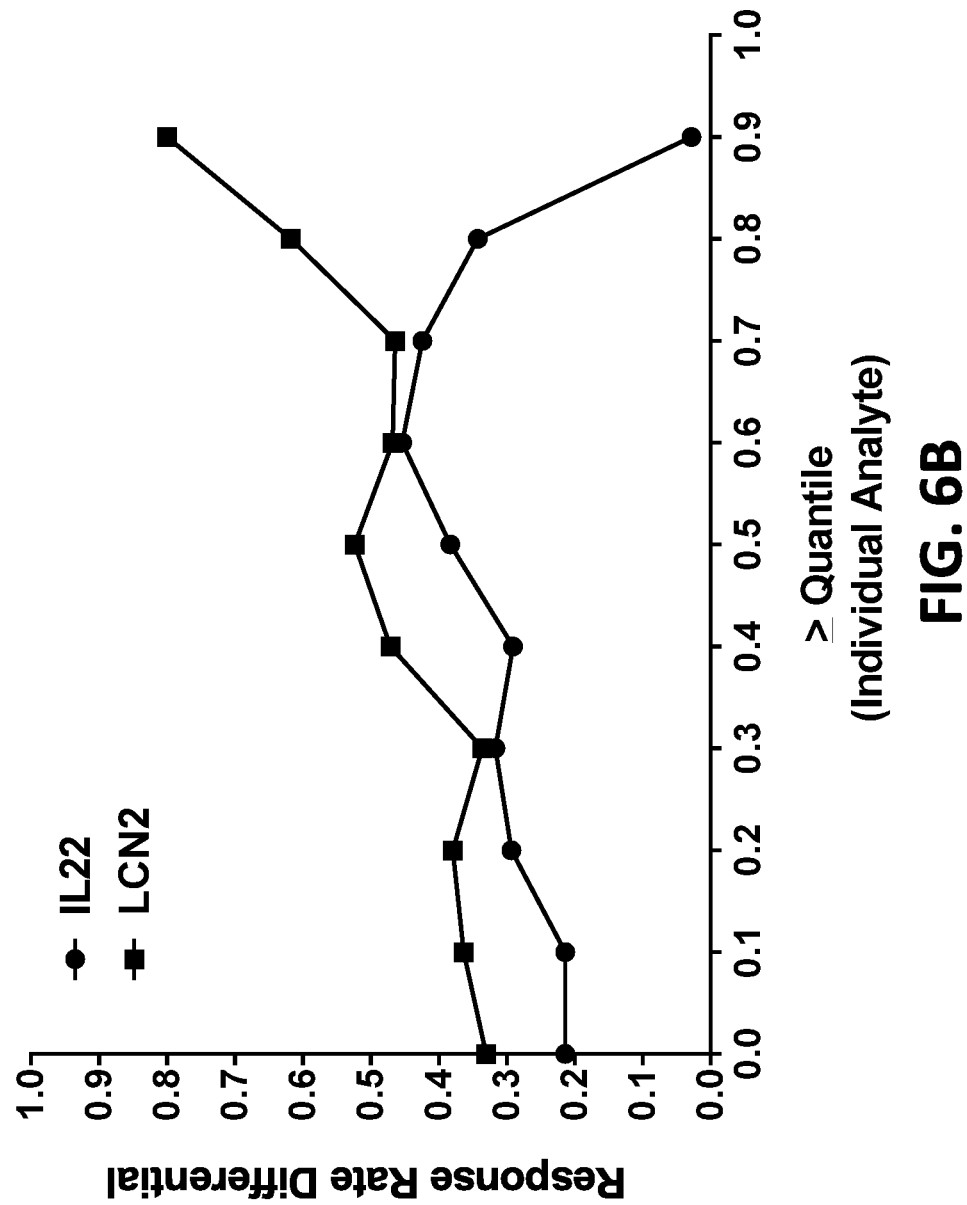
Figure 6C:
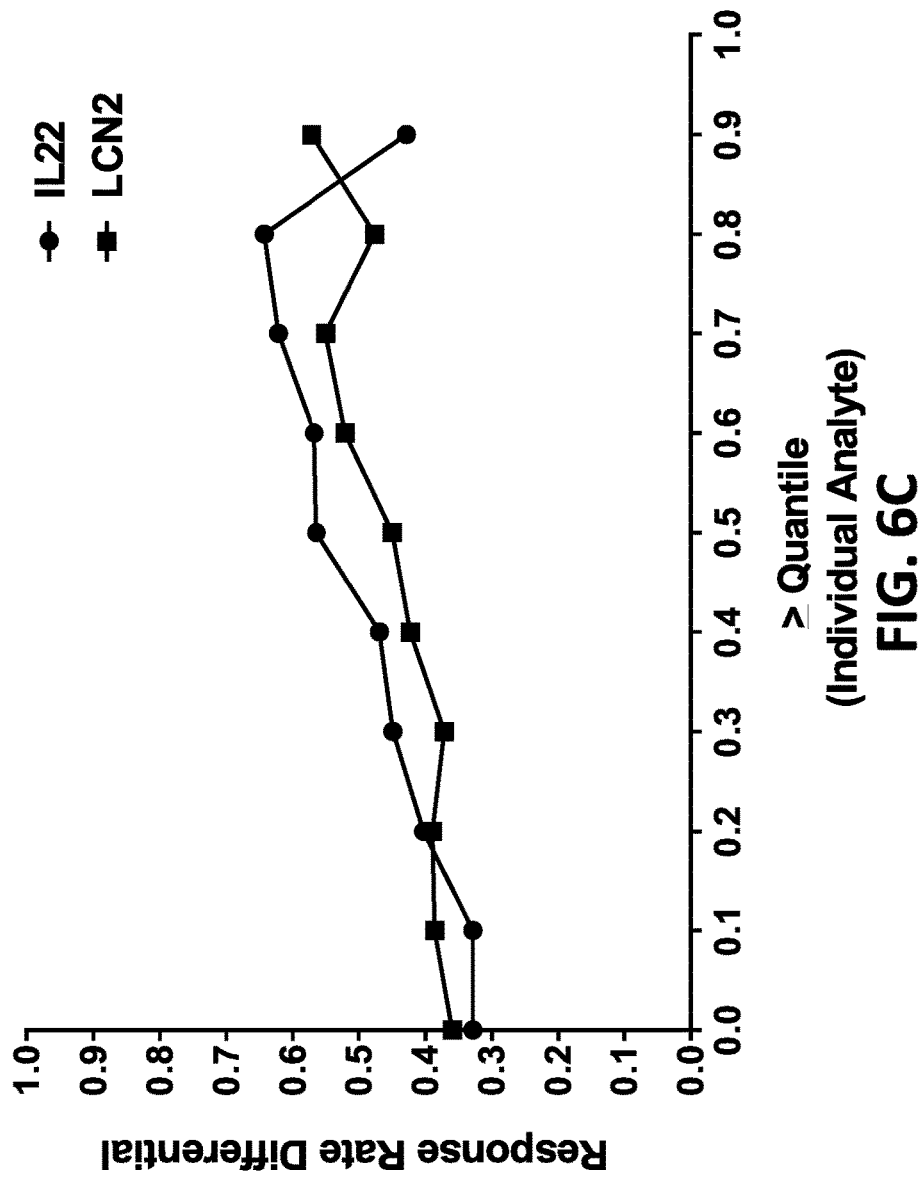

FIGS. 6A-C show the differential clinical response rate between subjects treated with MEDI2070 compared to placebo as measured by: (FIG. 6A) the difference between the percentage (%) of subjects achieving a CDAI score <150 or a reduction in CDAI score of >100); (FIG. 6B) the difference between the percentage (%) of subjects achieving a 100 point improvement in CDAI score; or (FIG. 6C) the difference between the percentage (%) of subjects achieving a CDAI score <150 or a reduction in CDAI score of >100, + also achieving a >50% reduction in either FCP or CRP compared to baseline FCP or CRP; between subjects treated with MEDI2070 and placebo at Week 8 as a function of baseline IL22 and LCN2 levels. Clinical Response rates are reported as the delta or difference between the rate observed for MEDI2070 treated subjects and the rate observed for subjects treated with placebo ("Response Rate Differential"). For the set of baseline values of IL22 or LCN2 across the entire study population, each distribution was divided into 10 levels, or deciles, such that each of the 11 analyte cut-offs (noted as "quantile" in FIGS. 6A-C) progressively segmented the study population into groups with 10% less of the total study population. For example, at $4^{th}$ decile (shown as the 0.4 quantile), 40% of the total study population had a baseline IL-22 or LCN2 serum level less than a particular analyte level while 60% of the total study population had a baseline IL-22 or LCN2 serum level greater than or equal to the particular analyte level. As shown in FIGS. 6A-C, CD patients treated with MEDI2070 having increasingly higher levels of baseline IL22 or LCN2 achieved higher clinical response rates (as measured using three different clinical response measurements) compared to placebo, illustrating that MEDI2070 induced better clinical responses in patients with high baseline IL22 or LCN2 serum levels at week 8. Subjects with high levels of IL22 or LCN2 (including, e.g., subjects with IL22 or LCN2 levels at the $5^{th}$, $6^{th}$ or $7^{th}$ deciles (0.5, 0.6 or 0.7 quantiles)) had greater clinical response rate differences from placebo (irrespective of which of the three different clinical response measurements was used) compared to the IL22 or LCN2 low subjects (including, e.g. subjects with IL22 or LCN2 levels at the $1^{st}$ or $2^{nd}$ deciles (0.1 or 0.2 quantiles)). These results underscore the predictive value of high or elevated IL22 and/or LCN2 serum levels in identifying patients responsive to treatment with MEDI2070. A summary of the baseline IL22 or LCN2 serum levels corresponding to each of the deciles described in FIGS. 6A-C is provided in Example 4 (see TABLE 4 (IL22) or TABLE 5 (LCN2)).

Figure 7:
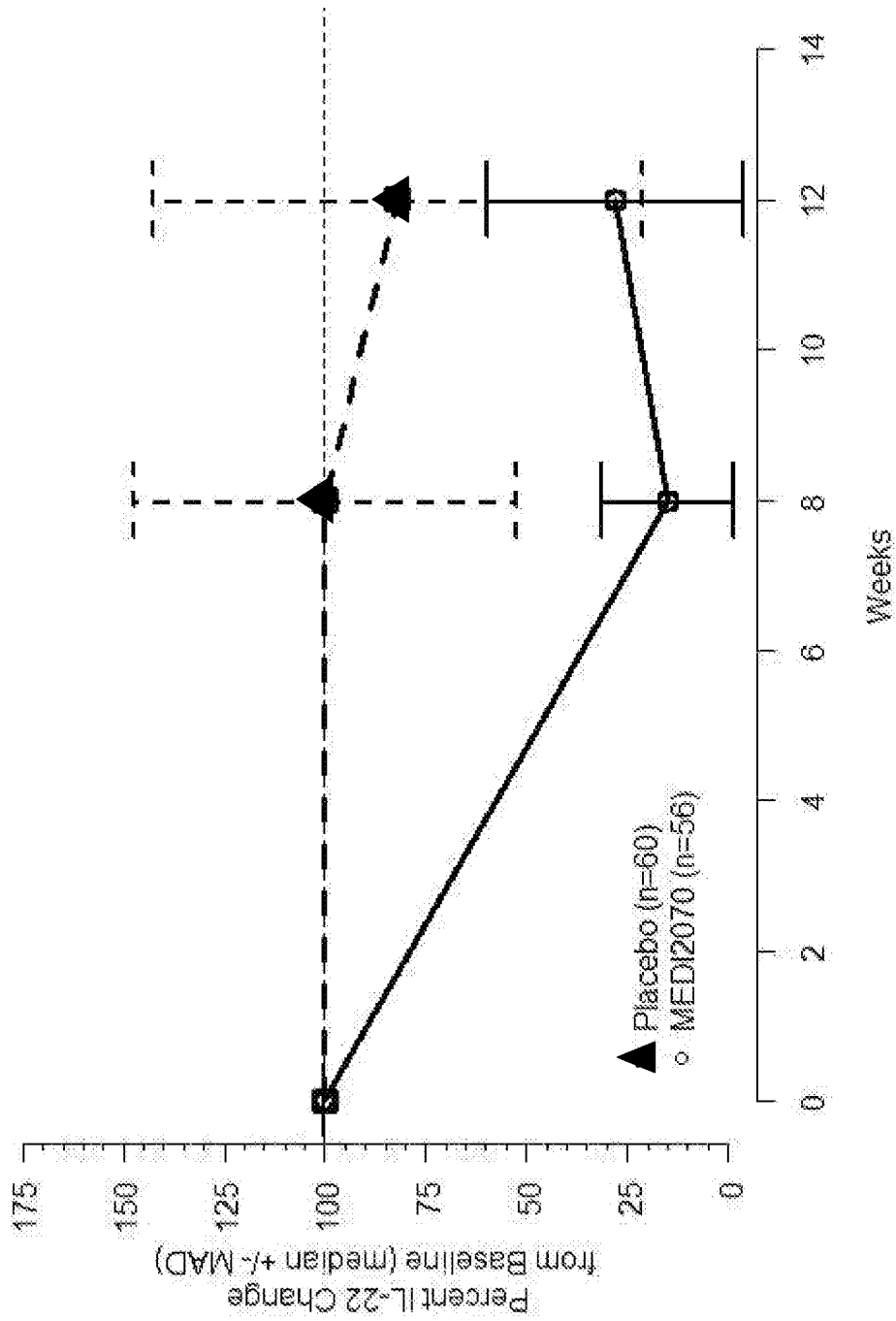

FIG. 7 shows percent reduction from baseline in serum IL22 levels in MEDI2070 and placebo groups. Error bars represent median absolute deviation (MAD). Compared to treatment with placebo, treatment with MEDI2070 was associated with a significantly greater drop in serum IL-22 levels by Week 8. "N" corresponds to the number of subjects at week 0.

Figure 8:
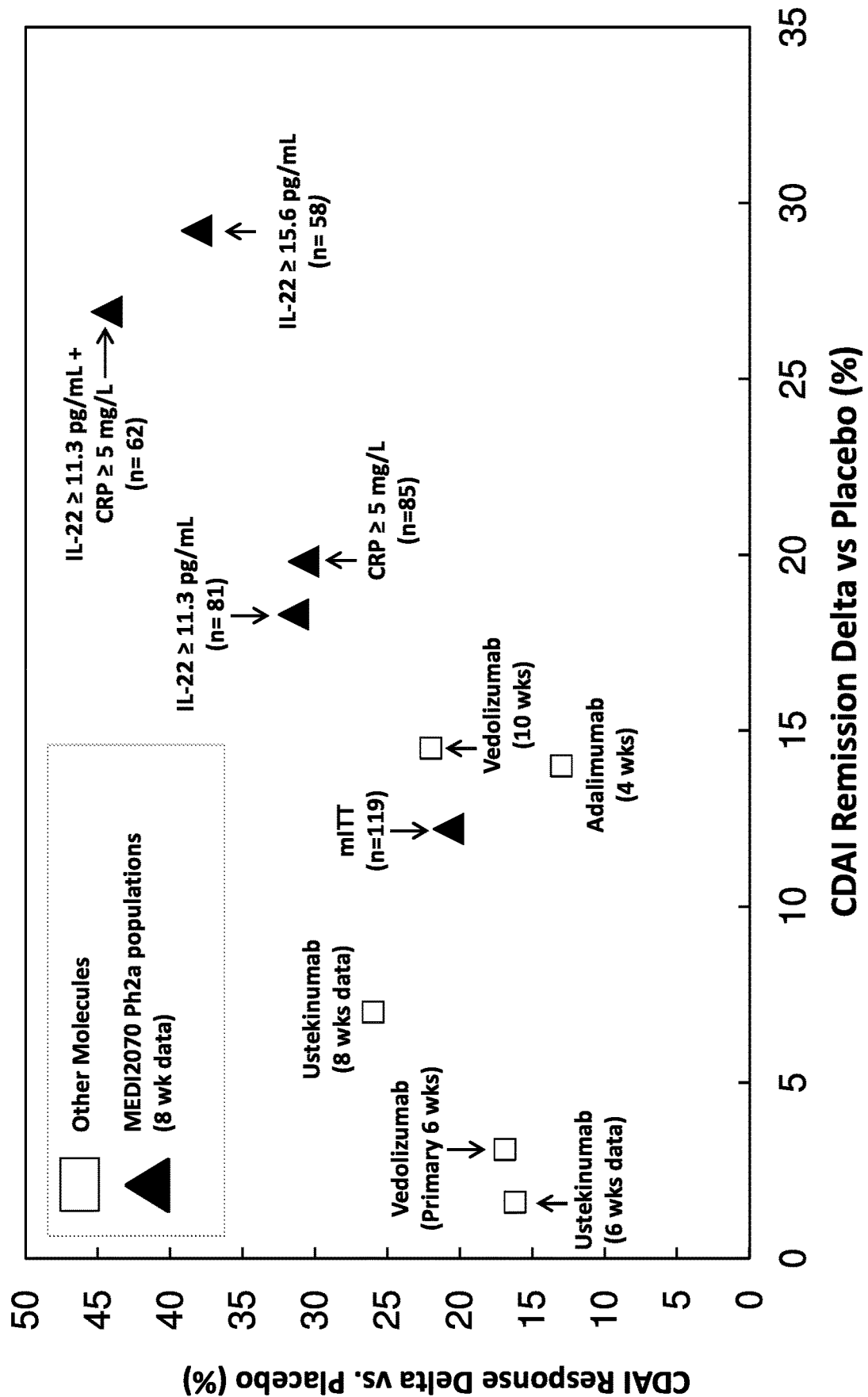

FIG. 8 compares the differential clinical response rate (defined as the difference in the percentage (%) of subjects achieving a CDAI-100 response between treatment and placebo ("CDAI Response Delta vs. Placebo")) (y axis) and the differential clinical remission rate (defined as the difference in the percentage (%) of subjects achieving a total CDAI score of below 150 points between treatment and placebo ("CDAI Remission Delta vs. Placebo")) (x axis) for patients treated with various molecules administered for 4-10 weeks as shown. Patients treated with MEDI2070 for 8 weeks who had a baseline CRP≥5 mg/L (n=85); baseline IL-22≥11.3 pg/mL (n=81); baseline IL-22≥15.6 pg/mL (n=58); or baseline IL-22≥11.3 pg/mL+CRP≥5 mg/L (n=62) (as measured using the IL22 immunoassay described in Example 3) had increased CDAI-100 response rates and/or CDAI remission rates. Both the CDAI-100 response rates and the CDAI remission rates of patients treated with MEDI2070 for 8 weeks who had a baseline CRP≥5 mg/L; baseline IL-22≥11.3 pg/mL; baseline IL-22≥15.6 pg/mL; or baseline IL-22≥11.3 pg/mL+CRP≥5 mg/L (as measured using the IL22 immunoassay described in Example 3) were greater than the reported CDAI-100 response rates and/or the CDAI remission rates for other molecules currently approved or under development to treat CD patients including: Ustekinumab (after 6 weeks or 8 weeks of treatment with a 6 mg/kg dose as reported in FIG. 1 of Sandborn et al., N Engl J Med. 2012 Oct. 18; 367(16):1519-28); Vedolizumab (after 6 weeks or 10 weeks of treatment as reported in FIG. 3 of Sands et. al., Gastroenterology. 2014 September; 147(3):618-627); or Adalimumab (after 4 weeks of treatment in patients who are secondary failures to infliximab as reported in Sandborn et. al, Ann Intern Med. 2007; 146:829-838). The overall clinical response and clinical remission rates for all patients treated with MEDI2070 in the Phase 2a study, irrespective of biomarker status (mITT (n=119)), was similar to the response rates of other molecules currently approved or under development. mITT, Modified Intent-to-Treat Population. TABLE 6 summarizes the CDAI-100 response rate differential and the CDAI remission rate differential for each of the MEDI2070-treated subgroups plotted in FIG. 8.

DETAILED DESCRIPTION

The present disclosure relates to the use of one or more IL23 pathway proteins (including but not limited to interleukin-22 (IL22) and/or lipocalin-2 (LCN2)) as biomarkers to predict clinical outcomes in patients suffering from interleukin 23 (IL23)-mediated diseases and treated with an IL23 antagonist which target, for example, the p40 subunit of IL12 and IL23 (targeted, e.g., by ustekinumab), or the p19 subunit of IL23 (targeted, e.g., by tildrakinumab, guselkumab, MEDI2070, BI-655066, and LY-3074828).

One or more genes or proteins in the IL23 pathway that can be used as biomarkers according to the methods disclosed herein include, e.g., interleukin-22 (IL22), lipocalin-2 (LCN2), chemokine (CC motif) ligand 20 (CCL20, MIP-3a), IL23R, IL12B, IL6, IL21, TNF, CCR6, CCL22, IL1R1, IFN gamma, S100 calcium-binding protein A12 (S100A12), defensin B2 (DEFB-2, DEFB-4), interleukin-1 beta (IL13), serine (or cysteine) proteinase inhibitor member 3 (SERPINB3), peptidase inhibitor 3 (PI3)/Elafin, human cathelicidin (LL37), retinoid-related orphan receptor-γ (RORγ and RORγT), interleukin-26 (IL26), psoriasin (S100A7), defensin beta 103B (DEFB103B), or GM-CSF. See Haider et al. J. Immunol. 180: 1913-1920 (2008); Nakae et al. J. Leukocyte Biol. 81: 1258-1268 (2007); Guttman-Yassky et al. J Immunol. 181(10): 7420-7427 (2008); El-Behi Nature Immunol. 12:568-75 (2011), Wilson, et al., Nature Immunology 8:950-7 (2007); all of which are herein incorporated by reference in their entireties.

The present disclosure provides, for example, methods to treat, prevent and/or ameliorate an IL23-mediated disease, to predict clinical outcomes, select patients for treatment, or stratify a population of patients suffering from a specific disease or disorder mediated by IL23 based on determining the expression levels of one, two, three, or more IL23 pathway biomarkers, including, e.g., IL22 and/or LCN2. Accordingly, in one aspect, the present disclosure provides methods comprising determining the expression levels of one or more IL23 pathway biomarkers (e.g., levels of IL22, levels of LCN2, or combinations thereof) in a sample obtained from a subject having an Il23-mediated disease to determine the appropriate course of treatment.

CD is a chronic transmural inflammatory disease of unknown etiology that most commonly affects the distal ileum and colon, and may occur in any part of the gastrointestinal (GI) tract. Patients with CD have uncontrolled inflammation that causes direct or collateral damage to the intestinal mucosa. The leading current hypothesis is that, in genetically predisposed individuals, this inflammation can result either from persistence of inflammatory stimulus, due to impaired gut barrier function, or from a dysregulated inflammatory response (Sandborn et al. Gastroenterol. 135: 1130-41 (2008); Rutgeerts et al. Aliment Pharmacol Ther. 17(12):1435-50 (2003)). CD occurs most commonly between the ages of 15 and 35 years, although patients of any age may be affected.

Commonly used medical therapies include aminosalicylates, (including sulfasalazine and mesalamine), systemic corticosteroids, immunosuppressive agents (e.g., azathioprine and methotrexate); antibacterial agents; and biologic agent, e.g., adalimumab/HUMIRA® (Abbott laboratories, IL) (SEQ ID NOS:21, 22), infliximab/REMICADE® (Janssen Biotech, Inc), certolizumab/CIMZIA® (UCB, Inc, Smyrna, Ga.)

(SEQ ID NOS: 23, 24), vedolizumab/ENTYVIO® (Takeda Pharmaceuticals America, Inc., Deerfield, Ill.), and Natalizumab/TYSABRI™ (Biogen Idec Inc, Cambridge, Mass.). Being a highly heterogeneous disease, it is difficult to predict whether a patient will respond favorably to a certain therapy.

The IL23 pathway biomarkers disclosed herein (e.g., expression ranges and/or threshold levels of IL22 and/or LCN2, alone or in combination with, for example, elevated or high levels of clinical biomarkers including CRP and/or FCP), can be used to stratify and/or identify a population of subjects having an IL23-mediated disease such as CD suitable for treatment with an IL23 antagonists (including, e.g., an anti-IL23 antibody or antigen-binding fragment thereof). Within each one of the strata, the IL23 pathway biomarkers disclosed herein can be used, for example, for diagnosing a patient, treating a patient, for example, with an IL23 antagonist (e.g., an anti-IL23 antibody targeting, e.g., the p19 subunit of IL23); selecting or non-selecting a patient for treatment, for example, with an IL23 antagonist (e.g., an anti-IL23 antibody targeting, e.g., the p19 subunit of IL23); selecting a certain treatment, for example, with an IL23 antagonist (e.g., an anti-IL23 antibody targeting, e.g., the p19 subunit of IL23); suspending or modifying temporarily or permanently a treatment; determining the prognosis of a patient; or monitoring the effect of a treatment, wherein those methods comprise, for example, determining expression ranges and/or threshold levels of IL22 and/or LCN2 alone or in combination with other biomarkers.

In some aspects, the IL23 antagonist is an anti-IL23 antibody which can specifically bind to the p19 subunit of IL23 (SEQ ID NO: 13), to the p40 subunit of IL23 (SEQ ID NO: 14), or both. In some aspects, the IL23 antagonist is an anti-IL23 antibody or other molecule (e.g., small molecule, aptamer, scaffolding molecule, etc) which can compete for binding to the p19 subunit of IL23 (SEQ ID NO: 13), to the p40 subunit of IL23 (SEQ ID NO: 14), or both, with MEDI2070 or another anti-IL23 antibody known in the art.

In some aspects, the anti-IL23 antibody or antigen-binding fragment thereof comprises the heavy chain (HC) (SEQ ID NO: 15) and/or the light chain (SEQ ID NO: 16) of MEDI2070, or an antigen-binding fragment, variant, or derivative thereof. In some aspects, the anti-IL23 antibody or antigen-binding fragment thereof comprises the variable region (VH) (SEQ ID NO: 5) and/or the light chain variable region (VL) (SEQ ID NO: 6) of MEDI2070. In some aspects, the anti-IL23 antibody or antigen-binding fragment thereof comprises at least one of the complementarity determining regions of MEDI2070 (SEQ ID NOS: 31-36). In some aspects, the anti-IL23 antibody or antigen-binding fragment thereof comprises a VH region comprising the sequence of SEQ ID NO: 43 and/or a VL region comprising the sequence of SEQ ID NO: 44, or an antigen-binding fragment, variant, or derivative thereof. In some aspects, the anti-IL23 antibody or antigen-binding fragment thereof comprises at least one of the complementarity determining regions of SEQ ID NOS:45-47 (CDRs of the VH of SEQ ID NO:43) and/or SEQ ID NOS: 48-50 (CDRs of the VL of SEQ ID NO:44).

In other aspects, the IL23 antagonist is an anti-IL23 antibody selected from ustekinumab or briakinumab (targeting the p40 subunit of IL23), guselkumab, tildrakizumab, BI-655066 or LY-3074828 (targeting the p19 subunit of IL23), an antigen-binding fragment thereof, or a combination thereof. In other aspects, the IL23 antagonist is a molecule competing with ustekinumab or briakinumab (targeting the p40 subunit of IL23), guselkumab, tildrakizumab, BI-655066 or LY-3074828 (targeting the p19 subunit of IL23), an antigen-binding fragment thereof, or a combination thereof for binding to IL23.

The methods disclosed herein are not only applicable to IL23-binding antibodies. The method disclosed herein can be applied to any inhibitors of the p19 subunit of IL23, including for example antibodies and antigen-binding fragments thereof, aptamers, scaffolding molecules, small molecules, soluble IL23 receptors, etc.

In order that the present disclosure can be more readily understood, certain terms are first defined. Additional definitions are set forth throughout the detailed description.

I. Definitions

The headings provided herein are not limitations of the various aspects or aspects of the disclosure, which can be had by reference to the specification as a whole. Accordingly, the terms defined immediately below are more fully defined by reference to the specification in its entirety.

In this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Wherever aspects are described herein with the language "comprising," otherwise analogous aspects described in terms of "consisting of" and/or "consisting essentially of" are also provided.

The term "about" as used in connection with a numerical value throughout the specification and the claims denotes an interval of accuracy, familiar and acceptable to a person skilled in the art. In general, such interval of accuracy is ±15%.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form.

Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

Nucleotides are referred to by their commonly accepted single-letter codes. Unless otherwise indicated, nucleic acids are written left to right in 5' to 3' orientation. Nucleotides are referred to herein by their commonly known one-letter symbols recommended by the IUPAC-IUB Biochemical Nomenclature Commission. Accordingly, A represents adenine, C represents cytosine, G represents guanine, T represents thymine, U represents uracil.

The terms "polynucleotide," "oligonucleotide," "nucleic acid" and "nucleic acid molecule" and "gene" are used interchangeably herein to refer to polymers of nucleotides of any length, and ribonucleotides, deoxyribonucleotides, analogs thereof, or mixtures thereof.

The phrase "DNA sequence" refers to a contiguous nucleic acid sequence. The sequence can be either single stranded or double stranded, DNA or RNA, but double stranded DNA sequences are preferable. The sequence can be an oligonucleotide of 6 to 20 nucleotides in length to a full length genomic sequence of thousands or hundreds of thousands of base pairs.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

A polypeptide, antibody, polynucleotide, vector, cell, or composition which is "isolated" is a polypeptide, polynucleotide, or composition which is in a form not found in nature. Isolated polypeptides, polynucleotides, or compositions include those which have been purified to a degree that they are no longer in a form in which they are found in nature. In some aspects, a polypeptide, polynucleotide, or composition which is isolated is substantially pure.

The term "amino acid substitution" refers to replacing an amino acid residue present in a parent sequence with another amino acid residue. An amino acid can be substituted in a parent sequence, for example, via chemical peptide synthesis or through recombinant methods known in the art. Accordingly, references to a "substitution at position X" or "substitution at position X" refer to the substitution of an amino acid present at position X with an alternative amino acid residue. In some aspects, substitution patterns can described according to the schema AXY, wherein A is the single letter code corresponding to the amino acid naturally present at position X, and Y is the substituting amino acid residue. In other aspects, substitution patterns can described according to the schema XY, wherein Y is the single letter code corresponding to the amino acid residue substituting the amino acid naturally present at position X.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

Non-conservative substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala, Ser) or no side chain (e.g., Gly).

Other substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

The term "amino acid insertion" refers to introducing a new amino acid residue between two amino acid residues present in the parent sequence. An amino acid can be inserted in a parent sequence, for example, via chemical peptide synthesis or through recombinant methods known in the art. Accordingly as used herein, the phrase "insertion between positions X and Y" wherein X and Y correspond to amino acid positions, refers to the insertion of an amino acid between the X and Y positions, and also to the insertion in a nucleic acid sequence of a codon encoding an amino acid between the codons encoding the amino acids at positions X and Y.

The term "percent sequence identity" between two polypeptide or polynucleotide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that align with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

As used herein, the term "antibody" refers to at least the minimal portion of an antibody which is capable of binding to antigen, e.g. IL23, comprising at least the variable domain of a heavy chain (VH) and the variable domain of a light chain (VL) in the context of a typical antibody produced by a B cell. Basic antibody structures in vertebrate systems are relatively well understood. See, e.g., Harlow et al., Antibodies: A Laboratory Manual, (Cold Spring Harbor Laboratory Press, 2nd ed. 1988).

Antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG, IgG2, IgG3, IgG4, IgA1 and IgA2) or subclass of immunoglobulin molecule.

Thus, in view if this definition of the term "antibody," references to an antibody, e.g., the anti-IL23 antibody MEDI2070, refer to the MEDI2070 antibody and also to antigen-binding fragments, variants, and derivatives thereof. In some aspects, the antibody is an anti-IL23 antibody which can specifically bind to the p19 subunit of IL23 (SEQ ID NO: 13), to the p40 subunit of IL23 (SEQ ID NO: 14), or both.

In some aspects, the anti-IL23 antibody or antigen-binding fragment thereof comprises, consists, or consists essentially of the heavy chain (HC) (SEQ ID NO: 15) and/or the light chain (SEQ ID NO: 16) of MEDI2070, or an antigen-binding fragment, variant, or derivative thereof. In some aspects, the anti-IL23 antibody or antigen-binding fragment thereof comprises, consists, or consists essentially of the heavy chain variable region (VH) (SEQ ID NO: 5) and/or the light chain variable region (VL) (SEQ ID NO: 6) of MEDI2070. In some aspects, the anti-IL23 antibody or antigen-binding fragment thereof comprises at least one of the complementarity determining regions of MEDI2070 (SEQ ID NOS: 31-36), e.g., it comprises one, two, three, four, five, or the six complementarity determining regions of MEDI2070.

In some aspects, the anti-IL23 antibody or antigen-binding fragment thereof comprises a VH region comprising, consisting, or consisting essentially of the sequence of SEQ ID NO:43 and/or a VL region comprising, consisting, or consisting essentially of the sequence of SEQ ID NO:44, or an antigen-binding fragment, variant, or derivative thereof. In some aspects, the anti-IL23 antibody or antigen-binding fragment thereof comprises at least one of the complementarity determining regions of SEQ ID NOS:45-47 (CDRs of the VH of SEQ ID NO:43) and/or SEQ ID NOS: 48-50 (CDRs of the VL of SEQ ID NO:44). See U.S. Pat. No. 8,722,033, which is herein incorporated by reference in its entirety.

In other aspects, the IL23 antagonist is an anti-IL23 antibody selected from ustekinumab or briakinumab (targeting the p40 subunit of IL23), guselkumab, tildrakizumab, BI-655066 or LY-3074828 (targeting the p19 subunit of IL23), an antigen-binding fragment thereof, or a combination thereof. In other aspects, the IL23 antagonist is a molecule competing with ustekinumab or briakinumab (targeting the p40 subunit of IL23), guselkumab, tildrakizumab, BI-655066 or LY-3074828 (targeting the p19 subunit of IL23), an antigen-binding fragment thereof, or a combination thereof, for binding to IL23.

In some aspects, the antibody is a naturally-occurring antibody, e.g., an antibody isolated and/or purified from a mammal, or produced by a hybridoma generated from a mammalian cell. In some aspects, the antibody is a genetically-engineered antibody, e.g., a humanized antibody, a chimeric antibody, a CDR-grafted antibody, a humaneered antibody, a bispecific antibody, a trispecific antibody, and the like. Genetic engineering techniques also provide the ability to make fully human antibodies in a non-human source. In some aspects, the antibody is generated using phage display.

In some aspects, the antibody is in polymeric, oligomeric, or multimeric form. In certain aspects in which the antibody comprises two or more distinct antigen binding regions fragments, the antibody is considered bispecific, trispecific, or multi-specific, or bivalent, trivalent, or multivalent, depending on the number of distinct epitopes that are recognized and bound by the antibody.

In some aspects, the binding agent is an antigen binding fragment of any antibody of the preceding paragraphs. The antigen binding fragment (also referred to herein as "antigen binding portion") may be an antigen binding fragment of any of the antibodies described herein. The antigen binding fragment can be any part of an antibody that has at least one antigen binding site, including, but not limited to, Fab, Fab', F(ab')2, Fd, Fvs, dsFv, disulfide-linked Fvs (sdFv), single chain Fvs (scFVs), fragments comprising either a light or heavy chain variable domain, single-chain antibodies, diabodies, triabodies, bis-scFvs, fragments expressed by a Fab expression library, domain antibodies, VhH domains, V-NAR domains, VH domains, VL domains, and the like.

A typical antibody comprises at least two heavy (H) chains and two light (L) chains interconnected by disulfide bonds. Each heavy chain is comprised of a heavy chain variable region (abbreviated herein as VH, VH region, or VH domain) and a heavy chain constant region. The heavy chain constant region is comprised of three or four constant domains, CH1, CH2, CH3, and CH4. Each light chain is comprised of a light chain variable region (abbreviated herein as VL, VL region, or VL domain) and a light chain constant region. The light chain constant region is comprised of one domain, CL.

The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. Framework regions can be designated according to their respective VH and VL regions. Thus, e.g., VH-FW1 would refer to the first framework region of VH. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

By "specifically binds," it is generally meant that an antibody (e.g., an anti-IL23 antibody) or fragment, variant, or derivative thereof binds to an epitope via its antigen-binding domain, and that the binding entails some complementarity between the antigen binding domain and the epitope. According to this definition, an antibody is said to "specifically bind" to an epitope when it binds to that epitope via its antigen-binding domain more readily than it would bind to a random, unrelated epitope.

The term "epitope" as used herein refers to an antigenic protein determinant capable of binding to an antibody (e.g., an anti-IL23 antibody) or fragment, variant, or derivative thereof binds disclosed herein. In some aspects, the term epitope refers to a protein determinant (e.g., an amino acid sequence) of the p19 subunit of IL23. In some aspects, the term epitope refers to a protein determinant (e.g., an amino acid sequence) of the p40 subunit of IL23. Epitopes usually consist of chemically active surface groupings of molecules such as amino acids or sugar side chains and usually have specific three dimensional structural characteristics, as well as specific charge characteristics. The part of an antibody or binding molecule that recognizes the epitope is called a paratope. The epitopes of protein antigens are divided into two categories, conformational epitopes and linear epitopes, based on their structure and interaction with the paratope. A conformational epitope is composed of discontinuous sections of the antigen's amino acid sequence. These epitopes interact with the paratope based on the 3-D surface features and shape or tertiary structure of the antigen. By contrast, linear epitopes interact with the paratope based on their primary structure. A linear epitope is formed by a continuous sequence of amino acids from the antigen.

The term "antibody binding site" refers to a region in the antigen (e.g., an amino acid sequence of the p19 subunit of IL23, or an amino acid sequence of the p40 subunit of IL23) comprising a continuous or discontinuous site (i.e., an epitope) to which a complementary antibody specifically binds. Thus, the antibody binding site can contain additional areas in the antigen which are beyond the epitope and which can determine properties such as binding affinity and/or stability, or affect properties such as antigen enzymatic activity or dimerization. Accordingly, even if two antibodies bind to the same epitope within an antigen, if the antibody molecules establish distinct intermolecular contacts with amino acids outside of the epitope, such antibodies are considered to bind to distinct antibody binding sites.

An antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen-binding fragment to a given epitope by at least 90%, at least 80%, at least 70%, at least 60%, or at least 50%.

Antibodies or antigen-binding fragments, variants, or derivatives thereof disclosed herein can be described or specified in terms of the epitope(s) or portion(s) of an antigen, e.g., a target polysaccharide that they recognize or specifically bind. For example, the portion of IL23 that specifically interacts with the antigen-binding domain of an anti-Il23 antibody (e.g., MEDI2070) is an "epitope."

The term "IL23-mediated disease or disorder," used interchangeably with "IL23-mediated disease" herein, as well as grammatical variants thereof, refers to any pathology known in the art to be caused by (alone or in association with other mediators), exacerbated by, associated with, or prolonged by abnormal levels of IL23 or abnormal activation of the IL23 pathway in the subject having the disorder. Non-limiting examples include IL23-mediated inflammatory bowel diseases (e.g., Crohn's disease), as well as pulmonary diseases, chronic inflammatory skin diseases, inflammatory diseases, autoimmune diseases, neurodegenerative diseases, or cancer. In some aspects, the IL23-mediated inflammatory bowel disease is CD, ulcerative colitis (UC), Behçet's disease, or celiac disease. In some aspects, the IL23-mediated pulmonary disease is asthma (e.g., allergic asthma, atopic asthma, corticosteroid naive asthma, chronic asthma, corticosteroid resistant asthma, corticosteroid refractory asthma, asthma due to smoking, or asthma uncontrolled on corticosteroids), idiopathic pulmonary fibrosis (IPF), or chronic obstructive pulmonary disease (COPD). In some aspects, the IL23-mediated chronic inflammatory skin disease is atopic dermatitis, allergic contact dermatitis, eczema, psoriasis, alopecia areata, or palmoplantar pustulosis. In some aspects, the IL23-mediated inflammatory disease is psoriatic arthritis, anklyosing spondylitis, arthritis, rheumatoid arthritis (RA), a rheumatic disorder, ANCA vasculitis, Bechet's disease, or autoimmune thyroiditis. In some aspects, the IL23-mediated autoimmune disease is multiple sclerosis (MS), Sjogren's syndrome (SS), systemic lupus erythematosus (SLE), autoimmune encephalomyelitis, collagen-induced arthritis, or type 1 diabetes mellitus. In some aspects, the IL23-mediated neurodegenerative disease is Alzheimer's disease. In some aspects, the IL23-mediated cancer is melanoma, colorectal cancer, stomach cancer, myeloma, prostate cancer, colitis-associated cancer, ovarian cancer, oral cancer, esophageal cancer, leukemia hepatitis B virus (HBV)-related hepatocellular carcinoma, breast cancer, lung cancer, and nasopharyngeal cancer. In some aspects, the IL23-mediated disease or disorder is a microbial infection, including, e.g., mycobacterial disease, or leishmaniasis. In some aspects, the IL23-mediated disease or disorder is a fungal or a viral infection (see, e.g., Khader et al., Mucosal Immunol 2(5): 403-411 (2009)).

As used herein, the terms "treat," "treating," "treatment," or "treatment of" as used herein refers methods that are aimed at (1) to reducing the potential for an IL23-mediated disease or disorder, e.g., delaying or preventing the onset of an IL23-mediated disease or disorder, (2) reducing the occurrence of the IL23-mediated disease or disorder, e.g., slowing down or stopping the progression or aggravation of the symptoms or physical deterioration associated with the IL23-mediated disease or disorder, (3) a reduction in the severity or amelioration of the symptoms of the IL23-mediated disease or disorder, preferably, to an extent that the subject no longer suffers discomfort and/or altered function due to it (for example, a relative reduction in CD exacerbations or disease severity when compared to untreated patients), and/or (4) curing the IL23-mediated disease or disorder.

Unless otherwise specified, the terms "treat," "treating," "treatment," or "treatment of" (or grammatically equivalent terms) refer to both prophylactic and therapeutic treatment regimes. Thus, a treatment may be administered prior to the onset of the disease, for a prophylactic or preventive action. It may also be administered after initiation of the IL23-mediated disease or disorder, for a therapeutic action. In some aspects, treatment of an IL23-mediated disease or disorder can comprise surgery.

The terms "subject" or "patient" as used herein refer to any subject, particularly a mammalian subject, for whom diagnosis, prognosis, or therapy of an IL23-mediated disease or disorder is desired. As used herein, the terms "subject" or "patient" include any human or nonhuman animal. The term "nonhuman animal" includes all vertebrates, e.g., mammals and non-mammals, such as nonhuman primates, sheep, dogs, cats, horses, cows, bears, chickens, amphibians, reptiles, etc. As used herein, phrases such as "a patient having an IL23-mediated disease" includes subjects, such as mammalian subjects, including humans that would benefit from the administration of a therapy, imaging or other diagnostic procedure, and/or preventive treatment for that IL23-mediated disease.

In some aspects, a subject is a naïve subject. A "naïve subject" is a subject that has not been administered a therapy, for example a therapeutic agent. In some aspects, a naïve subject has not been treated with a therapeutic agent prior to being diagnosed as having an IL23-mediated disease. In some aspects, a subject has received therapy and/or one or more doses of a therapeutic agent (e.g., a therapeutic agent capable of modulating an IL23-mediated disease) prior to being diagnosed as having an IL23-mediated disease.

In some aspects, the term "patient having an IL23-mediated disease or disorder," for example a patient having a specific IL23-mediated disease such as Crohn's disease (i.e., a "Crohn's disease patient" or "CD patient"), refers to a subject that presents one or more symptoms indicative of the IL23-mediated disease or disorder (e.g., CD) or that is screened for a particular IL23-mediated disease or disorder (e.g., CD). Alternatively or additionally, the term "patient having an IL23-mediated disease" also encompasses subjects suspected of having an IL23-mediated disease or disorder (e.g., CD) or who may have one or more risk factor (e.g., age, sex, family history, etc). The term also encompasses subjects that have not been tested for an IL23-mediated disease or disorder, as well as subjects that have received an initial diagnosis.

The term "therapy" as used herein includes any means for curing, mitigating, or preventing an IL23-mediated disease or disorder, including, for example, therapeutic agents, instrumentation, supportive measures, and surgical or rehabilitative procedures. In this respect, the term therapy encompasses any protocol, method and/or therapeutic or diagnostic that can be used in prevention, management, treatment, and/or amelioration of an IL23-mediated disease or disorder.

The term "therapeutic agent" as used herein refers to any therapeutically active substance that is administered to a subject having an IL23-mediated disease or disorder to produce a desired, usually beneficial, effect. The term therapeutic agent includes, e.g., classical low molecular weight therapeutic agents commonly referred to as small molecule drugs and biologics including but not limited to antibodies or active fragments thereof, peptides, protein drugs, protein conjugate drugs, etc. A therapeutic agent can also be a pro-drug, which metabolizes into the desired therapeutically active substance when administered to a subject. In some aspects, the therapeutic agent is a prophylactic agent. In addition, a therapeutic agent can be pharmaceutically formulated.

As used herein, the term "effective amount" or "pharmaceutically effective amount" or "therapeutically effective amount" refers to a quantity of the compound(s) in a preparation which, when administered to a subject is sufficient to achieve a desired therapeutic and/or prophylactic effect, e.g., an amount which alleviates a symptom, ameliorates a condition, or slows the onset of disease conditions according to clinically acceptable standards for the disorder or condition to be treated. The amount of a composition administered to the subject will depend on the type and severity of the IL23-mediated disease or disorder and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds and/or treatments.

The term "biological sample" is used herein in its broadest sense. The methods disclosed herein can be carried out using any sample that may contain the disclosed IL23 pathway biomarkers, e.g., IL22, LCN2, or a combination thereof. A biological sample is generally obtained from a subject. A sample may be of any biological tissue or fluid with which biomarkers of the present disclosure may be assayed. Frequently, a sample will be a "clinical sample", i.e., a sample derived from a patient.

With regard to the methods disclosed herein, non-limiting examples of the sample obtained from the subject comprises, for example, whole blood, blood serum, plasma, saliva, sputum, bronchoalveolar lavage fluid, cerebrospinal fluid, pleural fluid, pericardial fluid, ascites, synovial fluid, epithelial cells, urine, stool, skin, tissue, pinch or fine needle biopsy samples, and archival samples with known diagnosis, treatment and/or outcome history. Biological samples may also include sections of tissues such as frozen sections taken for histological purposes, or combinations thereof. Samples can be obtained by any means known in the art.

The term "biological sample" also encompasses any material derived by processing a biological sample. Derived materials include, but are not limited to, proteins extracted from the sample, nucleic acids extract from the sample, or nucleic acid sequences PCR amplified from the sample. Processing of a biological sample may involve one or more of: filtration, distillation, extraction, concentration, inactivation of interfering components, addition of reagents, and the like. For example, a blood sample can be fractionated into serum or into fractions containing particular types of cells In some aspects, a sample can be a combination of samples from an individual, such as a combination of a tissue and fluid sample. The sample can be pretreated as necessary by dilution in an appropriate buffer solution or concentrated. Any of a number of standard aqueous buffer solutions and/or protease inhibitor, employing any of a variety of buffers, such as phosphate, TRIS, or the like, at physiological pH, can be used.

The samples obtained to diagnose and/or determine expression levels of biomarkers for a certain IL23-mediated disease or disorder can vary depending on the specific methods used in the art. Thus, samples can be, for example, biological samples (whole blood, blood serum, plasma, saliva, sputum, bronchoalveolar lavage fluid, stool, epithelial cells, tissue biopsy samples, intestinal tissue biopsy samples, urine, skin, polyps, cerebrospinal fluid, pleural fluid, pericardial fluid, ascites, synovial fluid. etc), physical exam data (e.g., presence of fever, pain and/or abdominal tenderness), family history, results from laboratory tests (e.g., blood protein levels, blood sedimentation rates, body mineral levels, red blood cell counts, white blood cell counts, presence of blood and/or infectious microbes in stool samples), imaging studies and endoscopy (e.g., barium X-rays and other X-rays, CT scans, colonoscopy, sigmoidoscopy, video capsule endoscopy), etc.

As used herein, the term "control", when used to characterize a subject, refers to a subject that is healthy or to a patient who has been diagnosed with a specific disease other than an IL23-mediated disease or disorder. The term "control sample" refers to one, or more than one, biological samples obtained from a healthy subject or from a patient diagnosed with a disease other than an IL23-mediated disease or disorder.

A sample from a patient can be obtained before or after the administration of a therapy to treat an IL23-mediated disease or disorder. In some cases, successive samples can be obtained from the patient after therapy has commenced or after therapy has ceased. Samples can, for example, be requested by a healthcare provider (e.g., a doctor) or healthcare benefits provider, obtained and/or processed by the same or a different healthcare provider (e.g., a nurse, a hospital) or a clinical laboratory, and after processing, the results can be forwarded to the original healthcare provider or yet another healthcare provider, healthcare benefits provider or the patient.

Similarly, the quantification of the expression level of an IL23 pathway biomarker disclosed herein, e.g., IL22, LCN2, or a combination thereof; comparisons and/or ratios between biomarker gene or protein expression levels; evaluation of the absence or presence biomarkers; determination of biomarker levels with respect to a certain threshold; treatment decisions; or combinations thereof, can be performed by one or more healthcare providers, healthcare benefits providers, and/or clinical laboratories.

As used herein, the term "healthcare provider" refers to individuals or institutions that directly interact and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

As used herein, the term "clinical laboratory" refers to a facility for the examination or processing of materials derived from a living subject, e.g., a human being. Non-limiting examples of processing include biological, biochemical, serological, chemical, immunohematological, hematological, biophysical, cytological, pathological, genetic, or other examination of materials derived from the human body for the purpose of providing information, e.g., for the diagnosis, prevention, or treatment of any disease or impairment of, or the assessment of the health of living subjects, e.g., human beings. These examinations can also include procedures to collect or otherwise obtain a sample, prepare, determine, measure, or otherwise describe the presence or absence of various substances in the body of a living subject, e.g., a human being, or a sample obtained from the body of a living subject, e.g., a human being.

A clinical laboratory can, for example, collect or obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, or other related activities.

As used herein, the term "healthcare benefits provider" encompasses individual parties, organizations, or groups providing, presenting, offering, paying for in whole or in part, or being otherwise associated with giving a patient access to one or more healthcare benefits, benefit plans, health insurance, and/or healthcare expense account programs.

In some aspects, a healthcare provider can administer or instruct another healthcare provider to administer a therapy to treat an IL23-mediated disease or disorder. A healthcare provider can implement or instruct another healthcare provider or patient to perform, for example, the following actions: obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, administer a therapy (e.g., a therapeutic agent that treats a IL23-mediated disease or disorder), commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent.

In some aspects, a healthcare benefits provider can authorize or deny, for example, collection of a sample, processing of a sample, submission of a sample, receipt of a sample, transfer of a sample, analysis or measurement a sample, quantification a sample, provision of results obtained after analyzing/measuring/quantifying a sample, transfer of results obtained after analyzing/measuring/quantifying a sample, comparison/scoring of results obtained after analyzing/measuring/quantifying one or more samples, transfer of the comparison/score from one or more samples, administration of a therapy or therapeutic agent, commencement of the administration of a therapy or therapeutic agent, cessation of the administration of a therapy or therapeutic agent, continuation of the administration of a therapy or therapeutic agent, temporary interruption of the administration of a therapy or therapeutic agent, increase of the amount of administered therapeutic agent, decrease of the amount of administered therapeutic agent, continuation of the administration of an amount of a therapeutic agent, increase in the frequency of administration of a therapeutic agent, decrease in the frequency of administration of a therapeutic agent, maintain the same dosing frequency on a therapeutic agent, replace a therapy or therapeutic agent by at least another therapy or therapeutic agent, or combine a therapy or therapeutic agent with at least another therapy or additional therapeutic agent.

In addition, a healthcare benefits provider can, e.g., authorize or deny the prescription of a therapy, authorize or deny coverage for therapy, authorize or deny reimbursement for the cost of therapy, determine or deny eligibility for therapy, etc.

II. IL23 Pathway Components as Clinical Response Biomarkers

The recent discovery of a new $CD4^+$ T cell subset, Th17, has transformed our understanding of the pathogenic basis of an increasing number of chronic immune-mediated diseases. Particularly in tissues that interface with the microbial environment-such as the intestinal and respiratory tracts and the skin—where most of the Th17 cells in the body reside, dysregulated immunity to self (or the extended self, the diverse microbiota that normally colonize these tissues) can result in chronic inflammatory disease. Various inflammatory conditions have potential targets for pharmacological development along the IL23 pathway. These include, for example, IL23, which affects the differentiation of Th17 cells.

Some IL23-mediated diseases and disorders, for example CD or psoriasis, are heterogeneous diseases showing a wide spectrum of symptoms, severity and therefore drug responsiveness. One of the problems in clinical management of IL23-mediated diseases and disorders is the difficulty to identify specific subgroups of patients undergoing early clinical flare-up of symptoms for a timely and appropriate treatment, or the identification of specific subgroups of patients that may or may not benefit from a certain therapy, e.g., treatment with an IL23-antagonist.

It has been reported that several genes and proteins are overexpressed in the serum of patients with IL23-mediated diseases and disorders. For example, elevated levels of IL22 and LCN2 have been reported in CD patients or in murine models of inflammatory bowel syndrome. Dige et al., Journal of Crohn's and Colitis 7:248-255 (2013) suggested that levels of IL22-producing $CD45RO^+CD4^+$ T cells may serve as a predictor of clinical response for the treatment of CD using an anti-TNFα antibody. However, the experimental data provided by Dige indicated that high baseline plasma levels of IL22 did not predict general responsiveness of an anti-TNFα treatment in CD patients, concluding that although the significance of IL22 was unknown, IL22 expression in CD patients supported the known heterogeneity of CD. Similarly, Schemmel et al. Inflamm. Bowel Dis. 14:204-212 (2008) disclosed that IL22 was elevated in serum of CD patients compared to healthy controls, and that IL22 serum expression correlated with disease activity; however, Schemmel was silent about the potential use of IL22, alone or in combination with other biomarkers, to stratify or identify a population of CD patients with higher responsiveness to a specific treatment. In addition, U.S. Publ. No. 2011/0212104 disclosed that levels of a number of molecules, including IL22 and LCN2 were elevated in CD patients and proposed IL22 and LCN2 as potential biomarkers for IBD (including CD and UC). Importantly, none of the references cited above disclosed thresholds, levels or ranges for those IL23 pathway biomarkers, including IL22 and/or LCN2, that could be used to stratify or identify a population of patients having an IL23-mediated disease and/or to select subpopulations of patients having an IL23-mediated disease for treatment with a specific IL23 antagonist (e.g., an anti-IL23 antibody targeting, e.g., the p19 subunit of IL23). Thus, there still remains a need in the art for methods of identifying and treating specific groups of patients having an IL23-mediated disease who are responsive to anti-IL23 therapies.

New therapeutic options, e.g., antibodies specifically targeting IL23 such as MEDI2070, have the potential to address the unmet medical needs of patients suffering from IL23-mediated diseases. Accordingly, means to identify, for example, groups of patients who are likely to have a good clinical response to MEDI2070 (e.g., a diagnostic biomarker or combination thereof) and/or other anti-IL23 therapeutics known in the art, could greatly augment their utility.

In general, the methods disclosed herein are based on the detection of changes in the levels of specific IL23 pathway biomarkers (including, e.g., IL22 and/or LCN2) in patients with IL23-mediated diseases or disorders (e.g., CD), and the correlation of these changes with increased clinical response to therapy with an IL23 antagonist (including, for example, an anti-IL23 antibody or antigen binding fragment thereof targeting, e.g., the p19 subunit of IL23). In other words, specific levels of IL23 pathway biomarkers (including, e.g., IL22 and/or LCN2) are correlated with clinical efficacy of therapies and useful to predict clinical outcomes in specific populations of patients suffering from an IL23-mediated disease or disorder, e.g., CD.

The term "IL23 pathway biomarker" as used herein encompasses proteins in the IL23 pathway including, e.g., interleukin-22 (IL22), lipocalin-2 (LCN2), chemokine (CC motif) ligand 20 (CCL20, MIP-3α), interleukin-17F (IL17F), IL17A/IL17F (IL17A/F), S100 calcium-binding protein A12 (S100A12), interleukin 23 receptor (IL23R), interleukin 12B (IL12B), interleukin 23A (IL23A), defensin B2 (DEFB-2, DEFB-4), IL1β, serine (or cysteine) proteinase inhibitor member 3 (SERPINB3), tumor necrosis factor alpha (TNF-α), CCL6, α3 integrin, interleukin-21 (IL21), CCR6, CCL22, IL1R1, IFNγ, PI3/Elafin, LL37, RORγ, RORγT, IL26, S100A7, DEFB103B, GM-CSF, or combinations thereof. See, e.g., Haider et al. J. Immunol. 180: 1913-1920 (2008); Nakae et al. J. Leukocyte Biol. 81: 1258-1268 (2007); Guttman-Yassky et al. J Immunol. 181 (10): 7420-7427 (2008), Wilson, et al. Nature Immunology 8:950-7 (2007); all of which are herein incorporated by reference in their entireties. In some aspects, the set of IL23 pathway biomarkers used by the methods disclosed herein comprises IL22 and/or LCN2.

In some aspects, the IL23 pathway biomarkers IL22 and/or LCN2 can be substituted or combined with one or more molecules present in other inflammation pathways known in the art, and/or with other biomarkers linked to IL23-mediated diseases or disorders known in the art, including, but not limited to, for example, C-reactive protein (CRP), calprotectin (S100A8/S100A9 complex), DMBT1, MIF, PAP/REG3α, REG3γ, haptoglobin, interleukin-6 (IL6), lactoferrin, GP-39 (YKL-40), GPX-2, GPX-3, neutrophil elastase, etc.

The term "biomarker" refers to a factor that is a distinctive indicator of a biological process, biological event, and/or pathologic condition, e.g., a predictor of clinical response to treatment with an IL23 antagonist (e.g., an anti-IL23 antibody targeting, e.g., the p19 subunit of IL23, or an antigen-binding fragment thereof). As used herein, the term biomarker encompasses both clinical markers and biological markers. Thus, in the context of the present invention, the term "biomarker" encompasses, e.g., "biological biomarkers" comprising, for example, IL23 pathway biomarkers such as IL22 and/or LCN2, other biomarkers liked to IL23-mediated diseases or disorders (e.g., CRP or calprotectin), and combinations thereof. The biological markers disclosed herein also include the genes encoding those proteins (DNA and/or RNA), as well as metabolic products.

The term "biomarker" also encompasses "clinical biomarkers" (also referred to as "clinical status markers") that can be predictive of response to biological therapies, for example, gender, age, concomitant drugs, smoking status, body mass index (BMI), etc. See, e.g., U.S. Publ. Nos. US20150065530, US20140141990, US20130005596, US20090233304, US 20140199709, US20130303398, US20110212104, which are herein incorporated by reference in their entireties.

The biomarkers disclosed herein (e.g., IL23 pathway components such as IL22 and/or LCN2) also include proteins having 80%, 81%, 82%, 83%, 84%, 85%, 86%, 87%, 88%, 89%, 90%, 91%, 92%, 93%, 94%, 95%, 96%, 97%, 98% or 99% sequence identity to their respective wild type sequences (e.g., in the case of IL22 and LCN2 to SEQ ID NOS: 2, and 4, respectively), and nucleic acids having 80%, 81%, 82%, 83%, 84%, 85%, 86%, 87%, 88%, 89%, 90%, 91%, 92%, 93%, 94%, 95%, 96%, 97%, 98% or 99% sequence identity to their respective wild type sequence (e.g., in the case of IL22 and LCN2 to SEQ ID NOS: 1, and 3, respectively).

The IL23 pathway biomarkers disclosed herein, e.g., IL22 and/or LCN2, also include fragments, variants, and derivatives thereof. As used herein, a "variant" biomarker contains at least one amino acid sequence alteration as compared to the amino acid sequence of the corresponding wild-type polypeptide. An amino acid sequence alteration can be, for example, a substitution, a deletion, or an insertion of one or more amino acids, preferably conservative substitutions. A variant biomarker can have any combination of amino acid substitutions, deletions or insertions. In one aspect, a biomarker variant polypeptide can have an integer number of amino acid alterations such that its amino acid sequence shares at least 60, 70, 80, 85, 90, 95, 97, 98, 99, 99.5 or 100% identity with the amino acid sequence of the corresponding wild-type polypeptide.

Descriptions for some of the IL23 pathway biomarkers discussed in the instant application are provided below.

a. Interleukin 22 (IL22)

The term "IL22" as used herein refer to the interleukin 22 protein (NCBI Reference Sequence NP_065386.1; SEQ ID NO: 2) encoded by the IL22 gene (NCBI Reference Sequence NM_020525.4; SEQ ID NO: 1). See also Uniprot Acc. No. Q9GZX6 herein incorporated by reference in its entirety. IL22 is a pro-inflammatory cytokine known to be expressed from Th17 cells. Wilson et al. Nature Immunol. 8:950 (2007). Increased serum levels of IL22 have also been associated with IBD. See, e.g., Schmechel et al. Inflamm. Bowel Dis. 14:204 (2008); and Brand et al. Am. J. Physiol. Gastrointest. Liver Physiol 290:G827-G838 (2006). IL22 has been shown to induce haptoglobin expression in hepatic cells (Dumoutier et al. Proc. Nat'l. Acad. Sci USA 97:10144 (2000)), to upregulate expression of REG3α, REG3γ, S100A8, S100A9 and haptoglobin in colon epithelial cells (Zheng et al. Nature Medicine 14:282 (2008)), and to upregulate expression of S100A8 and S100A9 in keratinocytes (Boniface et al. J. Immunol. 174:3695 (2005)).

IL22 has a 33 amino acid signal sequence, i.e., residues 34-179 of SEQ ID NO: 2 correspond to mature IL22. Xie et al. J. Biol. Chem. 275:31335 (2000).

The term IL22 also includes fragments, variants (e.g., S158G and other variants known in the art), and derivatives thereof (e.g., glycosylated or aglycosilated forms of the IL22 protein, or otherwise chemically modified forms of the protein). In some aspects, the term IL22 refers to the IL22 gene, which includes genomic DNA, cDNA, mRNA, and fragments thereof. In some aspects, the term IL22 also refers to oligonucleotides capable of specifically hybridizing to the IL22 gene under stringent conditions.

b. Lipocalin-2 (LCN2)

The term "LCN2" as used herein refers to the lipocalin-2 protein (NCBI Reference Sequence NP_005555.2; SEQ ID NO: 4) encoded by the LCN2 gene (NCBI Reference Sequence NM_005564.3; SEQ ID NO: 3). See also Uniprot Acc. No. P80188 herein incorporated by reference in its entirety. LCN2, also known as 24p3 and neutrophil gelatinase-associated lipocalin (NGAL) (Kjeldsen et al. J. Biol. Chem. 268:10425-10432 (1993)), is a 25 kDa secretory glycoprotein that was originally identified in mouse kidney cells and human neutrophil granules. It belongs to the lipocalin superfamily that includes over 20 small secretory proteins, such as RBP4, fatty acid binding proteins (FABP), major urinary proteins (MUP), apolipoprotein D (apoD) and prostaglandin D synthases (PODS). See Akerstrom et al. Biochim Biophys Acta. 1482:1-8 (2000). The common feature of this protein family is their capacity to bind and transport small lipophilic substances, such as free fatty acids, retinoids, arachidonic acid and various steroids (Flower, Biochem J. 318:1-14 (1996). LCN2 is expressed in colon epithelial cells and leukocytes in Crohn's disease colon.

LCN2 has a 20 amino acid signal sequence, i.e., residues 21-198 of SEQ ID NO: 4 correspond to mature LCN2. See Bundgaard et al. Biochem. Biophys. Res. Comm. 202:1468 (1994); International Appl. Publ. No. WO 2006/091035; and U.S. Pat. App. Pub. No. 20050261191, which are herein incorporated by reference in their entireties.

The term LCN2 also includes fragments, isoforms (e.g., isoform 2 in which the sequence DQCIDG (SEQ ID NO: 37) between residues 193 and 198 is replaced with the sequence GNGQSG (SEQ ID NO: 38), variants (e.g., G9R, L13S, K82N, I155V, S178Y, and other variants known in the art), and derivatives thereof (e.g., glycosylated or aglycosilated forms of the LCN2 protein, or otherwise chemically modified forms of the protein). In some aspects, the term LCN2 refers to the LCN2 gene, which includes genomic DNA, cDNA, mRNA, and fragments thereof. In some aspects, the term LCN2 also refers to oligonucleotides capable of specifically hybridizing to the LCN2 gene under stringent conditions.

c. C-Reactive Protein (CRP)

The IL23 pathway biomarkers disclosed herein, e.g., IL22 and/or LCN2, can be combined for diagnostic, predictive, or monitoring purposes with other IL23 pathway biomarkers, biomarkers downstream from the therapeutic intervention point (e.g., IL23), or biomarkers specific for a certain IL23-mediated disease or disorders. For example, for inflammatory bowel disease (IBD) (including, e.g., CD or UC), such specific biomarkers include C-reactive protein (CRP) and/or calprotectin, which are described below.

The term "CRP" as used herein refers to the C-reactive protein (NCBI Reference Sequence NP_000558.2; SEQ ID NO: 8) encoded by the CRP gene (NCBI Reference Sequence NM_000567.2; SEQ ID NO: 7). See also Uniprot Acc. No. P02741 herein incorporated by reference in its entirety. CRP (also known as PTX1) has long been recognized as an acute phase reactant that rises dramatically in concentration after tissue injury or inflammation. Elevated CRP levels have been associated with coronary artery disease. CRP has long been used as a marker for inflammatory bowel disease, especially Crohn's disease. See, e.g., Vermerie et cd. (2004) Inflamm. Bowel Dis. 10:661 and Keshet et al. (2009) Am. J. Med. ScL 337:248. For use as a biomarker in humans, CRP levels may be determined using a custom-designed ELISA assay, or, for example, using a commercially available ELISA kit, such as the QUANTIKINE® human CRP Immunoassay kit from R&D Systems (Minneapolis, Minn., USA) and the AssayMax® human lactoferrin ELISA kit from AssayPro (St. Charles, Mo., USA).

CRP has an 18 amino acid signal sequence, i.e., residues 19-224 of SEQ ID NO: 8 correspond to mature CRP.

The term CRP also includes fragments, variants (e.g., K1G, T1G, L170V, substitution of the sequence YSIFSYATKRQDNEIL (SEQ ID NO: 39) starting at position 16 with the sequence TVFSRMPPRDKTMRFF (SEQ ID NO: 40), deletion of sequence from position 80 to 98, and other variants known in the art), and derivatives thereof (e.g., the pyrrolidine N-terminal carboxylic acid modified form of CRP produced after cleavage of the residues 1-19 signal peptide, and other chemically modified forms of the protein). In isoform 2 of CRP the sequence from position 67 to 199 is missing. In some aspects, the term CRP refers to the CRP gene, which includes genomic DNA, cDNA, mRNA, and fragments thereof. In some aspects, the term CRP also refers to oligonucleotides capable of specifically hybridizing to the CRP gene under stringent conditions.

d. Calprotectin (S100A8/S100A9)

Calprotectin is a complex of the mammalian proteins S100A8 and S100A9 produced by neutrophils, monocytes, and epithelial cells under inflammatory conditions, Foell et al. J. Leukocyte Biol. 81:28 (2007). Calprotectin can inhibit the growth of *Staphylococcus aureus* in abscesses by chelation of nutrient $Mn^{2+}$ and $Zn^{2+}$. Corbin et al. Science 319:962 (2008). Calprotectin has long been associated with intestinal inflammation, and has been proposed as a marker for IBD. See, e.g., Lugering et al. Digestion 56:406 (1995); von Roon et al. Am. J. Gastroenterol. 102:803 (2007); Leach et al. Scand. J. Gastroenterol. 42:1321(2007); Langhorst et al. Am. J. Gastroenterol. 103:162 (2008). Its measurement in feces has been shown to be useful in detecting active IBD and predicting recurrence of disease. Angriman et al. Clinica Chimica Acta 381:63 (2007). In 2006, the U.S. Food & Drug Administration (FDA) approved the PHICAL® Fecal Calprotectin Immunoassay (Genova Diagnostics, Inc., Asheville, N.C., USA) for use in diagnosing IBD. See U.S. Pat. Nos. 4,833,074; 5,455,160; and 6,225,072. The test involves an ELISA assay with colorimetric readout. Other human calprotectin detection kits are also commercially available. See, e.g., U.S. Pat. No. 6,225,072. Detection of fecal calprotectin at levels greater than 100 µg/g of stool is diagnostic for IBD. von Roon et al. Am. J. Gastroenterol. 102:803 (2007). According to literature provided with the PHICAL® Test fecal calprotectin levels of over 50 µg/g are regarded as a "positive" result, based on median fecal calprotectin levels of over 1700 µg/g (e.g. 200-20.000 µg/g) in IBD patients and 25 µg/g normal healthy subjects.

S100A8 (S100 calcium-binding protein A8) (NCBI Reference Sequence NP_002955.2; SEQ ID NO: 10), also known as calgranulin A, cystic fibrosis antigen, myeloid-related protein 8, granulocyte L1 protein, calprotectin L1L subunit, CFAG, leukocyte L1 complex light chain, migration inhibitory factor-related protein 8, MRP-8, S100 calcium-binding protein A8, and urinary stone protein band A, is encoded by the S100A8 gene (NCBI Reference Sequence NM_002964.3; SEQ ID NO: 9). See also Uniprot Acc. No. P05109 herein incorporated by reference in its entirety.

S100A9 (S100 calcium-binding protein A9) (NCBI Reference Sequence NP_002956.1; SEQ ID NO: 12), also known as calgranulin B, cystic fibrosis antigen B, myeloid-related protein 14, calprotectin L1H subunit, leukocyte L1 complex heavy chain, migration inhibitory factor-related protein 14, and MRP-14, is encoded by the S100A9 gene (NCBI Reference Sequence NM_002965.3; SEQ ID NO: 11).

Neither S100A8 nor S100A9 have a classical signal sequence. Rammes et al. J. Bio. Chem. 272:9496 (1997). See also Uniprot Acc. No. P06702 herein incorporated by reference in its entirety. The term calprotectin also includes fragments, variants of the S100A8 and S100A9 proteins. For example, the initiator methionine of the S100A8 can be removed to yield N-terminally processed S100A8 protein comprising amino acid residues 2 to 93. Also, the cysteine amino acid at position 42 in the S100A8 protein can be S-nitrosylated to yield S-nitrosocysteine. In a variant of the S100A8 protein, the sequence from amino positions 80 to 93,VAAHKKSHEESHKE (SEQ ID NO: 41) is replaced with WQPTKKAMKKATKSS (SEQ ID NO: 42). Known variants of the S100A9 subunit of calprotectin include C3A, E36Q, M63A, E78Q, M81A, M83A, S6H, K25F, H28L, and H20R. The initiator methionine of S100A9 can be removed to yield N-terminally processed S100A9 protein comprising amino acid residues 2 to 114. After removal of the N-terminal Met, the N-terminal Thr can be blocked. The cysteine amino acid at position 3 in S100A9 can also be transiently S-nitrosylated to yield S-nitrosocysteine. S-nitrosylation of Cys-3 is implicated in LDL(ox)-induced S-nitrosylation of GAPDH at 'Cys-247' through a transnitrosylase mechanism involving a iNOS-S100A8/S100A9 complex. The histidine at position 105 in S100A9 can also be modified to pros-methylhistidine. In addition, the threonine at position 113 of S100A9 can be phosphorylated by MAPK14 to yield phosphothreonine.

In some aspects, the term calprotectin refers to the genes encoding S100A8 and/or S100A9, which includes genomic DNA, cDNA, mRNA, and fragments thereof. In some aspects, the term calprotectin also refers to oligonucleotides capable of specifically hybridizing to the genes encoding S100A8 or S100A9 under stringent conditions.

In some aspects of the present disclosure, the methods disclosed herein can be applied in IL23-mediated diseases such as inflammatory bowel disease (IBD) (including, e.g., CD or UC) by using a set of biomarkers comprising IL22 and/or LCN2 and optional additional biomarker such as CRP and/or calprotectin, as well as any combination or subset thereof. Throughout any sections of the instant application, the recitation of "IL22 and/or LCN2" encompasses the individual components of the list as well as combinations thereof. Thus, "IL22 and/or LCN2" encompasses IL22 alone; LCN2 alone; and IL22 and LCN2 together.

III. Detection and Quantification of IL23 Pathway Biomarkers

IL23 pathway biomarkers of the present invention, e.g., IL22 and/or LCN2 (either their expressed protein levels, or their respective nucleic acid levels, such as mRNA levels) can be detected and quantified by any of a number of methods well known to those of skill in the art. These methods include analytic biochemical methods such as electrophoresis, capillary electrophoresis, high performance liquid chromatography (HPLC), thin layer chromatography (TLC), hyperdiffusion chromatography, mass spectroscopy and the like, or various immunological methods such as fluid or gel precipitin reactions, immunodiffusion (single or double), immunohistochemistry, affinity chromatography, immunoelectrophoresis, radioimmunoassay (RIA), enzyme-linked immunosorbent assays (ELISAs), immunofluorescent assays, Western blotting, and the like.

In some aspects, the method used to detect and/or quantify the IL23 pathway biomarkers disclosed herein comprises measuring the level, concentration, or amount of RNA, e.g., mRNA, encoded by the gene or gene segments in the sample. Levels of RNA, e.g., mRNA, may be measured by any technique known in the art, including but not limited to northern blotting or quantitative PCR (qPCR), including methods such as reverse transcription qPCR, real time qPCR, and end-point qPCR. Alternatively, "tag based" technologies, such as Serial analysis of gene expression (SAGE) and RNA-Seq, may be carried out to provide a relative measure of the cellular concentration of different mRNAs.

In some aspects, the method used to detect and/or quantify the IL23 pathway biomarkers disclosed herein comprises measuring the level, concentration, or amount of the protein product encoded by the gene or gene segments in the sample. Suitable methods of determining expression levels of protein products are known in the art and include immunoassays (e.g., Western blotting, an enzyme-linked immunosorbent assay (ELISA), a radioimmunoassay (RIA), a sandwich immunoassay or an immunohistochemical assay). For a general review of immunoassays, see Methods in Cell Biology Volume 37: Antibodies in Cell Biology, Asai, ed. Academic Press, Inc. New York (1993); Basic and Clinical Immunology 7th Edition, Stites & Terr, eds. (1991). See also, e.g., U.S. Patent Application Publication No. 2007/0212723 A1, Shang et al., Circulation Research 101: 1146-1154 (2007); and International Patent Application Publication Nos. WO/2012/094651 and WO/2010/129964.

In some aspects, the IL23 pathway biomarkers, e.g., IL22 and/or LCN2, can be detected and/or quantified in an electrophoretic polypeptide separation (e.g., a 1- or 2-dimensional electrophoresis). Means of detecting polypeptides using electrophoretic techniques are well known to those skilled in the art (see generally, R. Scopes (1982) Polypeptide Purification, Springer-Verlag, N.Y.; Deutscher, (1990) Methods in Enzymology Vol. 182: Guide to Polypeptide Purification, Academic Press, Inc., N.Y.). In some aspects, a Western blot (immunoblot) analysis is used to detect and quantify the presence of IL22 and/or LCN2 in the sample. This technique generally comprises separating sample polypeptides by gel electrophoresis on the basis of molecular weight, transferring the separated polypeptides to a suitable solid support (such as a nitrocellulose filter, a nylon filter, or derivatized nylon filter), and incubating the sample with antibodies that specifically bind the analyte. Antibodies that specifically bind to the analyte may be directly labeled or alternatively may be detected subsequently using labeled antibodies (e.g., labeled sheep anti-mouse antibodies) that specifically bind to a domain of the primary antibody.

In some aspects, the IL23 pathway biomarkers, e.g., IL22 and/or LCN2, can be detected and/or quantified in the biological sample using an immunoassay. For a general review of immunoassays, see also Methods in Cell Biology Volume 37: Antibodies in Cell Biology, Asai, ed. Academic Press, Inc. New York (1993); Basic and Clinical Immunology 7th Edition, Stites & Terr, eds. (1991). In some aspects, the immunoassay can use one or more anti-IL22 and/or anti-LCN2 antibodies or antigen binding fragments thereof which recognize human IL22 or human LCN2, respectively.

In some aspects, the immunoassay comprises a sandwich immunoassay, e.g., an enzyme-linked immunosorbent assay (ELISA) or a sandwich electrochemiluminescent (ECL) assay, in which a first anti-IL22 or anti-LCN2 "capture" antibody or antigen-binding fragment thereof is attached to a solid support, antigen from a sample or standard is allowed to bind to the capture antibody, and then a second anti-IL22 or anti-LCN2 "detection" antibody or antigen binding fragment thereof is added and detected either by an enzymatic reaction, an ECL reaction, radioactivity, or other detection method.

In some aspects, the immunoassay comprises the following steps: First, the capture antibody or fragment thereof is allowed to bind to a solid support, e.g., a multi-well plate or other assay device known to those of ordinary skill in the art. The capture antibody is allowed to attach for a period of time, e.g., overnight, and then unbound antibody is removed. The plate can then be washed to remove any unbound capture antibody. The plate can then be treated with a blocking solution to allow non-specific protein to bind to any unbound regions of the solid support. Typical blocking solutions include an unrelated protein, e.g., nonfat dry milk or serum albumin. The plate can then again be washed to remove any unbound blocking solution. Next, a sample suspected of containing IL22 and/or LCN2 is added to the plate. Samples are typically serially diluted and plated in duplicate or triplicate. Controls, including standard amounts of IL22 or LCN2 or a suitable fragment thereof and various negative controls are also included. The antigen is allowed to bind to the capture antibody for a period of time, e.g., one hour at room temperature. Following incubation, the plate can then be washed to remove any unbound antigen. Next, a detection antibody is added. The detection antibody is typically an anti-IL22 or anti-LCN2 antibody that binds to a different IL22 or LCN2 epitope than the capture antibody. The detection antibody can be labeled or unlabeled. Where the detection antibody is unlabeled, an addition step of addition a labeled secondary antibody will be required, as is well known by those of ordinary skill in the art.

The detection antibody can be directly labeled with an enzyme, e.g., horseradish peroxidase or alkaline phosphatase, or can be labeled with a tag that will allow an enzyme to bind. For example the detection antibody can be conjugated to biotin, and the enzyme attached in a subsequent step by allowing enzyme-conjugated streptavidin to bind to the biotin tag. Alternatively, the detection antibody can be conjugated to a chemiluminescent, fluorescent, or ECL tag. An example of the latter is a ruthenium chelate. Following incubation, the plate can then be washed to remove any unbound detection antibody. Detection of the detection antibody can be accomplished by methods that vary based on the type of detection antibody that is used.

If the detection antibody is tagged with biotin, then enzyme-conjugated streptavidin is added, unbound streptavidin is washed away, and a substrate is added which provides a colorimetric reaction that can be read, e.g., on a spectrophotometer. If the detection antibody is conjugated to a ruthenium chelate, the plate is subjected to electrical current, and light emission is measured.

Immunoassays for detecting the IL23 pathway biomarkers disclosed herein, e.g., IL22 and/or LCN2, can be either competitive or noncompetitive. Noncompetitive immunoassays are assays in which the amount of captured analyte is directly measured. In competitive assays, the amount of analyte in the sample is measured indirectly by measuring the amount of an added (exogenous) labeled analyte displaced (or competed away) from a capture agent by the analyte present in the sample. In one competitive assay, a known amount of, in this case, labeled IL22 and/or LCN2 is added to the sample, and the sample is then contacted with a capture agent. The amount of labeled IL22 or LCN2 bound to the antibody is inversely proportional to the concentration of IL22 or LCN2 present in the sample.

In some aspects, the method directly measures IL22 and/or LCN2 levels in a patient sample, where absolute levels are calculated by plotting the immunoassay results on a standard curve using, e.g., purified full length or an IL22 or LCN2 fragment. The detected signal from the detection antibody can then be quantitated based on the various standards and controls included on the plate. By plotting the results on a standard curve, the absolute levels of IL22 and/or LCN2 in the test samples can be calculated, e.g., in pg or ng of IL22 and/or LCN2 per mL or pg or ng of IL22 and/or LCN2 per mg protein.

Detection assays for the IL23 pathway biomarkers disclosed herein, e.g., IL22 and/or LCN2, can be scored (as positive or negative or quantity of analyte) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of analyte concentration.

In some aspects, the measured expression levels of the IL23 pathway biomarkers disclosed herein represent an average expression level or a mean expression level based on more than one measurement of the expression level. In some aspects, the measured expression level is an average or mean of several measurements of expression levels of the same sample. In some aspects, the measured expression level is an average or mean of several measurements of expression levels of different samples containing the same components obtained from the same subject. In some aspects, the measured expression level is quantile normalized, as is done in RNA Seq techniques using techniques well known by those of ordinary skill in the art.

The term "level" as applied to an IL23 pathway biomarker disclosed herein, e.g., as in "IL22 level" and/or "LCN2 level" refers to a measurement that is made using any analytical method for detecting presence or expression of the biomarker (protein expression or gene expression) in a biological sample and that indicates the presence, absence, absolute amount or concentration, relative amount or concentration, titer, expression level, ratio of measured levels, or the like, of, for, or corresponding to biomarker in the biological sample.

The exact nature of the "value" or "level" depends on the specific designs and components of the particular analytical method employed to detect the IL23 pathway biomarker, e.g., IL22 and/or LCN2 (e.g., immunoassays, mass spectrometry methods, in vivo molecular imaging, gene expression profiling, aptamer-based assays, etc.). See, e.g., U.S. 2010/00221752.

As used herein with reference to IL23 pathway biomarker (e.g., IL22 and/or LCN2), the terms "elevated level", "increased level", "higher level" or "high level" refer to a level in a biological sample (e.g., blood serum) that is higher than the expression level or range of the biomarker measured in a control sample ('normal level'), or a specified threshold disclosed herein (including e.g., about 15.6 pg/mL for IL22 serum protein as measured using an IL22 immunoassay, including the IL22 immunoassay described in Example 3; and/or about 215 ng/mL for LCN2 serum protein as measured using an LCN2 immunoassay, including the LCN2 immunoassay described in Example 3).

As used herein with reference to IL23 pathway biomarker (e.g., IL22 and/or LCN2), the terms "lowered level," "reduced level", "decreased level" or "low level" refer to a level in a biological sample (e.g., blood serum) that is lower than the expression level or range of the biomarker measured in a control sample ('normal level'), or a specified threshold disclosed herein (including e.g., about 15.6 pg/mL for IL22 serum protein as measured using an IL22 immunoassay, including the IL22 immunoassay described in Example 3; and/or about 215 ng/mL for LCN2 serum protein as measured using an LCN2 immunoassay, including the LCN2 immunoassay described in Example 3).

The normal level or range for an IL23 pathway biomarker disclosed herein (e.g., IL22 and/or LCN2) can be defined in accordance with standard practice. Thus, the level measured in a particular biological sample can be compared with level or range of levels determined in similar normal samples. In this context, a normal sample or a control sample would be, for example, a sample obtained from an individual with no detectable symptoms of an IL23-mediated disease or disorder. The level of IL22 and/or LCN2 is said to be elevated wherein the respective level of IL22 and/or LCN2 is present in the test sample at a higher level or range than in a normal sample, control sample, or a specific threshold level disclosed herein (including e.g., about 15.6 pg/mL for IL22 serum protein as measured using an IL22 immunoassay, including the IL22 immunoassay described in Example 3; and/or about 215 ng/mL for LCN2 serum protein as measured using an LCN2 immunoassay, including the LCN2 immunoassay described in Example 3).

In some aspects, the level of the IL23 pathway biomarker disclosed herein (e.g., IL22 and/or LCN2) is considered to be elevated or high if it is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% higher than a normal sample or control sample, or a specific threshold level disclosed herein.

In some aspects, the level of the IL23 pathway biomarker disclosed herein (e.g., IL22 and/or LCN2) is considered to be reduced or low if it is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than a normal sample or control sample, or a specific threshold level disclosed herein.

As used herein, the term "threshold level" (or alternatively herein "threshold value" or "predetermined threshold level") refers to a level of a substance, e.g., an IL23 pathway biomarker such as IL22 and/or LCN2, which may be of interest for comparative purposes. In some aspects, a threshold level may be the expression level of a protein or nucleic acid expressed as an average of the level of the expression level of a protein or nucleic acid from samples taken from a control population of healthy (disease-free) subjects. In some aspects, the threshold level may be the level in the same subject at a different time, e.g., before the present assay, such as the level determined prior to the subject developing the disease or prior to initiating therapy. In general, samples are normalized by a common factor. For example, body fluid samples are normalized by volume body fluid and cell-containing samples are normalized by protein content or cell count. In another aspect, the threshold level may also refer to the level of expression of the same biomarker in a corresponding control sample or control group of subjects which do not respond to treatment, e.g., with an IL23 antagonist (e.g., an anti-IL23 antibody targeting, e.g., the p19 subunit of IL23, or an antigen-binding fragment thereof).

In some aspects, the expression level of an IL23 pathway biomarker such as IL22 and/or LCN2 is compared to a threshold level (or alternatively herein a "predetermined threshold level"). Thus, as used herein, the term "threshold level" or "predetermined threshold level" is a cutoff or threshold against which the measured expression level of a protein or nucleic acid is compared.

Based on comparison to known control samples, a "threshold level" for an IL23 pathway biomarker such as IL22 and/or LCN2 can be determined, and test samples that fall above or below those respective IL22 and/or LCN2 threshold levels indicate that the patient from whom the sample was obtained may benefit from treatment with an IL23 antagonist (e.g., an anti-IL23 antibody targeting, e.g., the p19 subunit of IL23, or an antigen-binding fragment thereof).

In some aspects, IL23 pathway biomarker (e.g., IL22 and/or LCN2) threshold levels (e.g., protein expression levels or gene expression levels) can be predetermined and matched as to the type of sample (e.g., serum, lung tissue, skin), the type of disease (e.g., asthma, IPF, COPD, Crohn's Disease, UC, or atopic dermatitis), and in some instances, the assay used.

As described in the Examples, IL22 protein levels quantified using the IL22 immunoassay described in Example 3 from serum samples from a population of moderate to severe Crohn's disease patients indicated that patients having higher or elevated IL22 levels greater than or equal to 15.6 pg/mL (the median IL22 level for the population of patients in the study) had increased clinical responses to an anti-IL23 antibody, while patients with lower or reduced IL22 levels less than 15.6 pg/mL had reduced clinical responses similar to those in the placebo group. See Examples 2-4; FIGS. 4, 6 and 8. Accordingly, in some aspects of the methods disclosed herein, the predetermined IL22 threshold level is about 15.6 µg/mL IL22 protein expression in serum as measured using the IL22 immunoassay described in Example 3. In some other aspects, the predetermined IL22 threshold level is about the median IL22 value in serum measured from a plurality of patients having an IL23-mediated disease as measured using the IL22 immunoassay described in Example 3. In some aspects, a "low level of IL22" (IL22 LO) is defined as a value below the median value of about 15.6 µg/mL IL22 protein expression in serum as measured using the IL22 immunoassay described in Example 3. In some aspects, a "high level of IL22 (IL22 HI) is defined as a value equal to or above the median value of about 15.6 pg/mL IL22 protein expression in serum as measured using the IL22 immunoassay described in Example 3.

In some aspects, the predetermined IL22 threshold level is about 15.6 pg/mL+/−10 pg/mL IL22 protein expression in serum as measured using the IL22 immunoassay described in Example 3. Accordingly, the IL22 threshold level can be about 5, 6, 7, 8, 9, 10, 11, 12, 13, 14, 15, 16, 17, 18, 19, 20, 21, 22, 23, 24, 25 or 26 pg/mL. In some aspects a "low level of IL22" (IL22 LO) is defined as a value below one of these threshold levels, whereas a "high level of IL22" (IL22 HI) is defined as a value equal to or above the same threshold level (i.e., if the threshold level was 20 pg/mL, a low level of IL22 would be below 20 pg/mL, and a high level of IL22 would be 20 pg/mL or above).

In some aspects, the predetermined IL22 threshold corresponds to the $2^{nd}$, $3^{rd}$, $4^{th}$, $5^{th}$, $6^{th}$, $7^{th}$ or $8^{th}$ decile IL22 baseline level as reported in TABLE 4. In some aspects, the predetermined IL22 threshold level is about 7.9 pg/mL, about 11.3 pg/mL, about 12.7 pg/mL, about 15.6 pg/mL, about 19.6 pg/mL, about 23.1 pg/mL, about 31.4 pg/mL or about 46.8 pg/mL IL22 protein expression in serum as measured using the IL22 immunoassay described in Example 3. In some aspects a "low level of IL22" (IL22 LO) is defined as a value below one of these threshold levels, whereas a "high level of IL22" (IL22 HI) is defined as a value equal to or above the same threshold level.

In some aspects, the predetermined IL22 threshold level as measured using the IL22 immunoassay described in Example 3 corresponds to a concentration of IL22 in serum between 7.9 pg/mL and 31.4 pg/mL, e.g., about 8, 9, 10, 11, 12, 13, 14, 15, 16, 17, 18, 19, 20, 21, 22, 23, 24, 25, 26, 27, 28, 29, 30, or 31 pg/mL.

As described in the Examples, LCN2 protein levels quantified using the LCN2 immunoassay described in Example 3 from serum samples from a population of moderate to severe Crohn's disease patients indicated that patients having higher or elevated LCN2 levels greater than or equal to 215 ng/mL (the median LCN2 level for the population of patients in the study) had increased clinical responses to an anti-IL23 antibody, while patients with lower or reduced LCN2 levels less than 215 ng/mL had reduced clinical responses. See Examples 2-4; FIGS. 5 and 6. Accordingly, in some aspects of the methods disclosed herein, the predetermined LCN2 threshold level is about 215 ng/mL LCN2 protein expression in serum as measured using the LCN2 immunoassay described in Example 3. In some other aspects, the predetermined LCN2 threshold level is about the median LCN2 value in serum measured from a plurality of patients having an IL23-mediated disease as measured using the LCN2 immunoassay described in Example 3. In some aspects, a "low level of LCN2" (LCN2 LO) is defined as a value below the median value of about 215 ng/mL LCN2 protein expression in serum as measured using the LCN2 immunoassay described in Example 3. In some aspects, a "high level of LCN2" (LCN2 HI) is defined as a value equal to or above the median value of about 215 ng LCN2/mL LCN2 protein expression in serum as measured using the LCN2 immunoassay described in Example 3.

In some aspects, the predetermined LCN2 threshold level is about 215 ng/mL+/−70 ng/mL LCN2 protein expression in serum as measured using the LCN2 immunoassay described in Example 3. Accordingly, the LCN2 threshold level can be about 145, 150, 155, 160, 165, 170, 175, 180, 185, 190, 195, 200, 205, 210, 215, 220, 225, 230, 235, 240, 245, 250, 255, 260, 265, 270, 275, 280 or 285 ng/mL. In some aspects a "low level of LCN2" (LCN2 LO) is defined as a value below one of these threshold levels, whereas a "high level of LCN2" (LCN2 HI) is defined as a value equal to or above the same threshold level (i.e., if the threshold level was 250 ng/mL, a low level of LCN2 would be below 250 ng/mL, and a high level of LCN2 would be 250 ng/mL or above).

In some aspects, the predetermined LCN2 threshold corresponds to the $1^{st}$, $2^{nd}$, $3^{rd}$, $4^{th}$, $5^{th}$, $6^{th}$ or $7^{th}$ decile LCN2 baseline level as reported in TABLE 5. In some aspects, the predetermined LCN2 threshold level is about 142.8 ng/mL, about 163.6 ng/mL, about 184.3 ng/mL, about 201.3 ng/mL, about 214.6 ng/mL, about 233.4 ng/mL, about 261.1 ng/mL, about 294.8 ng/mL, or about 326.6 ng/mL LCN2 protein expression in serum as measured using the immunoassay described in Example 3. In some aspects a "low level of LCN2" (LCN2 LO) is defined as a value below one of these threshold levels, whereas a "high level of LCN2" (LCN2 HI) is defined as a value equal to or above the same threshold level.

In some aspects, the predetermined LCN2 threshold level as measured using the LCN2 immunoassay described in Example 3 corresponds to a concentration of LCN2 in serum between 143 ng/mL and 261 ng/mL, e.g., about 145, 150, 155, 160, 165, 170, 175, 180, 185, 190, 195, 200, 205, 210, 215, 220, 225, 230, 235, 240, 245, 250, 255 or 260 ng/mL.

In some aspects, the threshold level is the average or mean expression level measured from samples obtained from healthy volunteers as reported in the manufacturer's manual of a commercial immunoassay used to detect the presence or absence of IL23 pathway biomarkers (e.g., IL22 and/or LCN2) in a sample. For example, solid Phase Sandwich ELISA kits to quantify IL22 or LCN2 available from R&D Systems (Human IL22 QUANTIKINE® ELISA Kit (Catalog Number D2200); or Human Lipocalin-2/NGAL QUANTIKINE® ELISA Kit (Catalog Number DLCN20/SLCN20/PDLCN20). The R&D Systems manufacturer's manual for the Human IL22 QUANTIKINE® ELISA Kit and the Human Lipocalin-2/NGAL QUANTIKINE® ELISA Kit are herein incorporated by reference in their entireties. Accordingly, as indicated in the Human IL22 QUANTIKINE® Assay manufacturer's manual, IL22 levels in serum (n=53), EDTA plasma (n=51), heparin plasma (n=53) and urine (n=42) from apparently healthy volunteers were evaluated using the IL22 QUANTIKINE® immunoassay and the IL22 mean values were 35.7 pg/mL for serum, 29.3 pg/mL for EDTA plasma, 31.7 pg/mL for heparin plasma, and 35.2 pg/mL for urine, respectively. Accordingly, in some aspects of the methods disclosed herein, the predetermined IL22 threshold level is about 35.7 pg/mL for serum, about 29.3 pg/mL for EDTA plasma, about 31.7 pg/mL for heparin plasma, and/or about 35.2 pg/mL for urine as measured by the Human IL22 QUANTIKINE® ELISA Kit (Catalog Number D2200; R&D Systems) following the manufacturer's instructions, for their respective samples. Similarly, as indicated in the Human LCN2 QUANTIKINE® Assay manufacturer's manual, detectable LCN2 levels in serum (n=35), heparin plasma (n=35), saliva (n=9) and urine (n=19) from apparently healthy volunteers were evaluated using the LCN2 QUANTIKINE® immunoassay and the LCN2 mean values were 119 ng/mL for serum, 94 ng/mL for heparin plasma, 320 ng/mL for saliva, and 9.94 ng/mL for urine, respectively. Accordingly, in some aspects of the methods disclosed herein, the predetermined LCN2 threshold level is about 119 ng/mL for serum, about 94 ng/mL for heparin plasma, about 320 ng/mL for saliva, and about 9.94 ng/mL for urine as measured by the Human Lipocalin-2/NGAL QUANTIKINE® ELISA Kit (Catalog Number DLCN20/SLCN20/PDLCN20; R&D Systems) following the manufacturer's instructions, for their respective samples.

In some aspects, the expression level of an IL23 pathway biomarker (e.g., IL22 and/or LCN2) measured in the sample is above or below the threshold level or threshold value. In these aspects where the expression level an IL23 pathway biomarker (e.g., IL22 and/or LCN2) measured in the sample is above or below the threshold level or threshold, the expression level can indicate that the patient from whom the sample was taken may benefit or not from treatment with an IL23 antagonist (e.g., an anti-IL23 antibody targeting, e.g., the p19 subunit of IL23, or an antigen-binding fragment thereof). The extent to which the measured expression level is above or below the threshold level or threshold value may be to any extent. In exemplary aspects, the measured expression level is at least or about 10% greater or lower than the threshold level (e.g., at least or about 15% greater or lower than the threshold level, at least or about 20% greater or lower than the threshold level, at least or about 25% greater or lower than the threshold level, at least or about 30% greater or lower than the threshold level, at least or about 35% greater or lower than the threshold level, at least or about 40% greater or lower than the threshold level, at least or about 45% greater or lower than the threshold level, at least or about 50% greater or lower than the threshold level, at least or about 55% greater or lower than the threshold level, at least or about 60% greater or lower than the threshold level, at least or about 65% greater or lower than the threshold level, at least or about 70% greater or lower than the threshold level, at least or about 75% greater or lower than the threshold level, at least or about 80% greater or lower than the threshold level, at least or about 85% greater or lower than the threshold level, at least or about 90% greater or lower than the threshold level, at least or about 95% greater or lower than the threshold level). In exemplary aspects, the measured expression level is at least 2-fold greater or lower than the threshold level, at least 3-fold greater or lower than the threshold level, at least 4-fold greater or lower than the threshold level, at least 5-fold greater or lower than the threshold level, at least 6-fold greater or lower than the threshold level, at least 7-fold greater or lower than the threshold level, at least 8-fold greater or lower than the threshold level, at least 9-fold greater or lower than the threshold level, or at least 10-fold greater or lower than the threshold level.

As discussed above, the level of IL23 pathway biomarkers disclosed herein (e.g., IL22 and/or LCN2) can be determined using methods known in the art. A person skilled in the art would appreciate that in addition to the QUANTIKINE® assays disclosed above, there are numerous methods available in the art that would allow the skilled artisan to determine threshold levels as described throughout this section, including the methods and immunoassays described in the Examples, in particular Example 3.

In some aspects, the predetermined threshold level of an IL23 pathway biomarker (e.g., IL22 and/or LCN2) is defined with respect to a certain percentile value in a population of subjects (e.g., a plurality of normal healthy patients, patients with a non-IL23-mediated disease and/or patients with an IL23-mediated disease). In some aspects, the predetermined threshold level for IL22 corresponds to the $10^{th}$, $15^{th}$, $20^{th}$, $25^{th}$, $30^{th}$, $35^{th}$, $40^{th}$, $45^{th}$, $50^{th}$, $50^{th}$, $55^{th}$, $60^{th}$, $65^{th}$, $70^{th}$, $75^{th}$, $80^{th}$, $85^{th}$, or $90^{th}$ percentile. In some aspects, the predetermined threshold level for LCN2 corresponds to the $10^{th}$, $15^{th}$, $20^{th}$, $25^{th}$, $30^{th}$, $35^{th}$, $40^{th}$, $45^{th}$, $50^{th}$, $50^{th}$, $55^{th}$, $60^{th}$, $65^{th}$, $70^{th}$, $75^{th}$, $80^{th}$, $85^{th}$, or $90^{th}$ percentile.

The threshold levels of IL23 pathway biomarkers, e.g., IL22 and/or LCN2 threshold levels (e.g., a protein expression level or a gene expression level) can vary based on the nature of the assay, e.g., the capture and detection antibodies used, the source, purity, and composition of the standard, and the like.

In one aspect, instead of using an arbitrary threshold level to determine whether a patient can benefit from treatment with an IL23 antagonist (e.g., an anti-IL23 antibody targeting, e.g., the p19 subunit of IL23, such as MEDI2070, or an antigen-binding fragment thereof), the patient's IL22 and/or LCN2 levels can be compared to one or more control IL22 and/or LCN2 levels. According to this aspect, the test sample (e.g., a sample from a patient suffering from an IL23-mediated disease or disorder) is compared to one or more control samples (e.g., samples taken from normal healthy individuals, earlier samples taken from the same patient, samples taken from patients with a non-IL23-mediated subset of the patient's disease, e.g., asthma, COPD, IPF, Crohn's Disease, UC, or atopic dermatitis, a predetermined standard amount of isolated IL22 or LCN2, or a combination thereof).

The results can be expressed as a ratio with the control samples to determine a percent increase or a percent decrease in the patient's IL22 and/or LCN2 levels (e.g., a protein expression level or a gene expression level) compared to the control IL22 and/or LCN2 levels. The control sample can be a matched pair with the patient sample, e.g., one or more of whole blood if the patient sample is whole blood, serum if the patient sample is serum, plasma if the patient sample is plasma, saliva if the patient sample is saliva, urine if the patient sample is urine, sputum if the patient sample is sputum, bronchoalveolar lavage fluid if the patient sample is bronchoalveolar lavage fluid, lung tissue if the patient sample is lung tissue, or skin if the patient sample is skin. Once determined, an IL22 and/or LCN2 expression level can be recorded in a patient's medical record.

In a particular aspect, a high level of IL22 (at least about 15.6 pg/mL in serum as measured using the IL22 immunoassay disclosed in Example 3), and/or a high level of LCN2 (at least about 215 ng/mL as measured using the LCN2 immunoassay disclosed in Example 3) are predictive of positive clinical response to an IL23 antagonist (e.g., an anti-IL23 antibody targeting, e.g., the p19 subunit of IL23, such as MEDI2070, or an antigen-binding fragment thereof) in a patient having an IL23-mediated disease (including, e.g., CD). In one aspect, the high level of IL22 is a value between about 7.9 pg/mL and about 31.4 pg/mL as measured using the IL22 immunoassay disclosed in Example 3. In one aspect, the high level of LCN2 is a value between about 143 pg/mL and about 261 pg/mL as measured using the LCN2 immunoassay disclosed in Example 3.

In a particular aspect, a level of IL22 above: about 7.9 pg/mL, about 11.3 pg/mL, about 12.7 pg/mL, about 15.6 pg/mL, about 19.6 pg/mL, about 23.1 pg/mL, about 31.4 pg/mL or about 49.8 pg/mL IL22 protein expression in serum as measured using the IL22 immunoassay described in Example 3; and/or a level of LCN2 above: about 142.8 ng/mL, about 163.6 ng/mL, about 184.3 ng/mL, about 201.3 ng/mL, about 214.6 ng/mL, about 233.4 ng/mL, about 261.1 ng/mL, about 294.8 ng/mL, or about 326.6 ng/mL LCN2 expression as measured according to the LCN2 immunoassay disclosed in Example 3 are predictive of positive clinical response to an IL23 antagonist (e.g., an anti-IL23 antibody targeting, e.g., the p19 subunit of IL23, such as MEDI2070, or an antigen-binding fragment thereof) in a patient having an IL23-mediated disease (including, e.g., CD).

In one aspect, administration of the IL23 antagonist (e.g., an anti-IL23 antibody targeting, e.g., the p19 subunit of IL23, such as MEDI2070, or an antigen-binding fragment thereof) results in a Crohn's Disease Activity Index (CDAI) response score reduction of at least 100 points, or reduction of the total CDAI score to below 150 points after first administering the IL23 antagonist (e.g., an anti-IL23 antibody targeting, e.g., the p19 subunit of IL23, such as MEDI2070, or an antigen-binding fragment thereof).

In other aspects, the administration of the IL23 antagonist (e.g., an anti-IL23 antibody targeting, e.g., the p19 subunit of IL23, such as MEDI2070, or an antigen-binding fragment thereof) results in a Crohn's Disease Activity Index (CDAI) response score reduction of at least 10, 15, 20, 25, 30, 35, 40, 45, 50, 55, 60, 65, 70, 75, 80, 85, 90, 95, 100, 105, 110, 115, 120, 125, 130, 135, 140, 145, or 150 points after administering of one or more doses the anti-IL23 antibody or antigen-binding fragment thereof.

IV. IL23 Antagonists

The IL23 pathway biomarkers disclosed herein (e.g., IL22 and/or LCN2) can be used, for example, to determine whether to make determination regarding whether to select for treatment, treat, monitor the treatment, or a begin, modify, or cease the treatment of a patient suffering from an IL23-mediated disease or disorder with an IL23 antagonist (e.g., an anti-IL23 antibody targeting, e.g., the p19 subunit of IL23, such as MEDI2070, or an antigen-binding fragment thereof).

As used herein, the term "IL23 antagonist" refers to any agent that can affect the expression, activity, or half-life of IL23 either in vitro or in vivo, or symptoms, pathology, or sequelae caused by or exacerbated by IL23 in a subject with an IL23-mediated disease or disorder, e.g., CD. An IL23 antagonist can be any therapeutic agent as defined herein, which either directly or indirectly can inhibit, lessen, or neutralize IL23 activity, inhibit or reduce IL23 expression, reduce IL23 half-life, or can prevent exacerbation of symptoms due to IL23. In certain aspects, an IL23 antagonist is an anti-IL23 monoclonal antibody.

Specific IL23 antagonists contemplated herein specifically bind and inhibit IL23, but do not inhibit IL12. An IL23 antagonist or binding agent of the present disclosure (e.g., and antibody such as MEDI2070) competitively inhibits binding of a reference molecule (e.g., a different IL23 antagonist or binding agent) to a given target site if it preferentially binds to that target site to the extent that it blocks, to some degree, binding of the reference molecule to the target site. Competitive inhibition can be determined by any method known in the art, for example, competition ELISA assays. An IL23 antagonist or binding agent of the present disclosure (e.g., an antibody such as MEDI2070) can be said to competitively inhibit binding of the reference molecule to a given epitope by at least about 90%, at least about 85%, at least about 80%, at least about 75%, at least about 70%, at least about 65%, at least about 60%, at least about 55%, or at least 50%.

In some aspects, the IL23 antagonist is an anti-IL23 antibody targeting, e.g., the p19 subunit of IL23, the p40 subunit of IL23, or both. An exemplary IL23 antagonist contemplated is the anti-IL23 antibody MEDI2070, which targets the p19 subunit of IL23. MEDI2070 is a fully human, Chinese Hamster Ovary (CHO) cell-derived, immunoglobulin G2 (IgG2) monoclonal antibody (MAb) that specifically binds to human IL23 with high affinity and prevents IL23 from interacting with the IL23 receptor. The molecule is a heterotetramer, consisting of 2 heavy chains of the IgG2 subclass and 2 light chains of the lambda subclass, which are covalently linked through disulfide bonds. See International Publ. WO 2011/056600, herein incorporated by reference.

MEDI2070 comprises a Heavy Chain of SEQ ID NO: 15 and a Light Chain of SEQ ID NO: 16. MEDI2070 comprises a heavy chain variable region (SEQ ID NO: 5) comprising VH-CDR1, VH-CDR2 and VH-CDR3 with sequences corresponding to SEQ ID NOs: 31, 32 and 33, respectively. MEDI2070 comprises a light chain variable region (SEQ ID NO: 6) comprising VL-CDR1, VL-CDR2 and VL-CDR3 with sequences corresponding to SEQ ID NOS: 34, 35, and 36, respectively.

As used herein, the term "MEDI2070" refers not only to an intact MEDI2070 immunoglobulin, but also to MEDI2070 antigen-binding fragments, variant, or derivatives thereof, antibodies or fragments thereof that bind to the same IL23 epitope as MEDI2070, or an antibodies or fragments thereof that competitively inhibit binding of MEDI2070 to IL23. Antibodies (or fragments thereof) that are identical or similar to MEDI2070 in amino acid sequence, particularly in the variable regions, or in the CDRs thereof (however, variations in the constant regions are also contemplated) are contemplated. For example, in one aspect, MEDI2070 refers to a polypeptide having an amino acid sequence that is about 70%, about 75%, about 80%, about 85%, about 90%, about 92%, about 95%, about 98%, about 99% or 100% identical to that of an MEDI2070 polypeptide disclosed herein (the heavy chain of MEDI2070, the light of MEDI2070). In some aspects, MEDI2070 is an isolated IL23 specific antigen binding protein comprising at least one, two, three, four, or the six complementarity determining regions of MEDI2070.

Another exemplary IL23 antagonist contemplated is an anti-IL23 antibody which targets the p19 subunit of IL23 comprising a VH of SEQ ID NO: 43 and/or a VL of SEQ ID NO: 44. In some aspects, the IL23 antagonist comprises a heavy chain variable region comprising VH-CDR1, VH-CDR2 and VH-CDR3 from SEQ ID NO: 43 (i.e., SEQ ID NOs: 45-47), and/or a light chain variable region comprising VL-CDR1, VL-CDR2 and VL-CDR3 from SEQ ID NO: 44 (i.e., SEQ ID NOs: 48-50). In some aspects, the IL23 antagonist binds to the same IL23 epitope as an antibody comprising a VH of SEQ ID NO: 43 and a VL of SEQ ID NO: 44. In some aspects, the IL23 antagonist competitively inhibits binding of an antibody comprising a VH of SEQ ID NO: 43 and a VL of SEQ ID NO: 44 to IL23. Antibodies (or fragments thereof) that comprise a VH and/or a VL domain identical or similar in amino acid sequence to a VH of SEQ ID NO: 43 and/or a VL of SEQ ID NO: 44, particularly in the variable regions, or in the CDRs thereof (however, variations in the constant regions are also contemplated) are contemplated. For example, in one aspect, the IL23 antagonist is a polypeptide having an amino acid sequence that is about 70%, about 75%, about 80%, about 85%, about 90%, about 92%, about 95%, about 98%, about 99% or 100% identical to a VH of SEQ ID NO:43 and/or a VL of SEQ ID NO:44. In some aspects, the IL23 antagonist an isolated IL23 specific antigen binding protein comprising at least one, two, three, four, or the six complementarity determining regions of a VH of SEQ ID NO:43 and/or a VL of SEQ ID NO:44.

The term "IL23 antagonist" encompasses also the antibodies targeting IL23 described for example in U.S. Pat. Nos. 7,491,391, 7,807,414, 7,872,102, 7,807,160, 8,362, 212, 7,935,344; 7,790,862; US2012282269, US20090123479, US20120128689, US20122664917, WO199905280, WO20070244846, WO2007027714, WO 2007076524, WO2007147019, WO2008103473, WO2008103432, WO2009043933, WO2009082624, WO 12009760, all of which are herein incorporated by reference in their entireties. In some aspects, "IL23 antagonist" encompasses antibodies and antigen fragments thereof (including, e.g., constructs such as scFvs) comprising one, two, three, four, five or six of the CDR sequences of the antibodies disclosed in the cited references. In some aspects, "IL23 antagonist" encompasses antibodies and antigen fragments thereof (including, e.g., constructs such as scFvs) competing for binding to IL23 with the antibodies disclosed in the cited references.

In some specific aspects, the term "IL23 antagonist" refers to ustekinumab (CNTO-1275, STELARA®) (SEQ ID NOS: 17, 18), briakinumab (ABT-874) (SEQ ID NOS: 25, 26), Guselkumab (CNTO-1959), tildrakinumab (MK-3222; SCH-900222) (SEQ ID NOS: 27,28), BI-655066 (see Krueger et al. J. Allergy Clin Immunol. 136:116-124 (2015)), LY-3074828 (see Gaffen et al. Nature Reviews Immunology 14: 585-600, (2014)), or an antigen-binding fragments thereof comprising one, two, three, four, five and/or six of their respective CDR sequences.

The IL-23 antagonists of the present disclosure can also be used in combination with one or more antagonists of other cytokines (e.g. antibodies), including but not limited to, IL17A, IL17F, TNF-α, IL-1β, IL-6 and TGF-β. See, e.g., Veldhoen, Immunity 24:179-189 (2006); Dong, Nat. Rev. Immunol. 6(4):329-333 (2006).

In various aspects, the IL-23 antagonists disclosed herein comprise antigen binding fragments of antibodies, such as fragments of any of the IL-23 antagonist antibodies referred to herein. Such fragments include, but are not limited to Fab, Fab', Fab'-SH, Fv, scFv, F(ab')$_2$, nanobodies, and diabodies.

The term "IL23 antagonist" also encompasses antagonists such as aptamers (see, e.g., U.S. Pat. Appl. Pub. No. 2007066550), peptides (e.g., as disclosed in Quiniou et al., Am J Physiol Regul Integr Comp Physiol. 2014 Nov. 15; 307(10):R1216-30), orally stable peptides against the IL-23 receptor, or small molecule inhibitors (e.g., Synta Pharmaceuticals' STA-5326).

V. Methods of Diagnosis, Treatment, and Monitoring of IL23-Mediated Diseases Based on IL23 Pathway Biomarker Levels IL23 pathway biomarkers that are differentially expressed in subjects having an IL23-mediated disease (e.g., CD) can be applied to predicting clinical outcomes when the subjects are treated with a certain therapy, for example, an IL23 antagonist (e.g., an anti-IL23 antibody targeting, e.g., the p19 subunit of IL23, such as MEDI2070, or an antigen-binding fragment thereof).

In some aspects, the IL23 antagonist is an anti-IL23 antibody or antigen-binding fragment thereof which can specifically bind to the p19 subunit of IL23 (SEQ ID NO: 13), to the p40 subunit of IL23 (SEQ ID NO: 14), or both, for example the anti-IL23 antibody MEDI2070, which targets the p19 subunit of IL23.

In some aspects, the anti-IL23 antibody or antigen-binding fragment thereof comprises the heavy chain (HC) (SEQ ID NO: 15) and/or the light chain (SEQ ID NO: 16) of MEDI2070, or an antigen-binding fragment, variant, or derivative thereof. In some aspects, the anti-IL23 antibody or antigen-binding fragment thereof comprises the heavy chain variable region (VH) (SEQ ID NO: 5) and/or the light chain variable region (VL) (SEQ ID NO: 6) of MEDI2070. In some aspects, the anti-IL23 antibody or antigen-binding fragment thereof comprises at least one of the complementarity determining regions of MEDI2070 (SEQ ID NOS: 31-36). In some aspects, the anti-IL23 antibody or antigen-binding fragment thereof comprises a VH region comprising the sequence of SEQ ID NO: 43 and/or a VL region comprising the sequence of SEQ ID NO: 44, or an antigen-binding fragment, variant, or derivative thereof. In some aspects, the anti-IL23 antibody or antigen-binding fragment thereof comprises at least one of the complementarity determining regions of SEQ ID NOS:45-47 (CDRs of the VH of SEQ ID NO:43) and/or SEQ ID NOS: 48-50 (CDRs of the VL of SEQ ID NO:44).

In other aspects, the IL23 antagonist is an anti-IL23 antibody selected from ustekinumab or briakinumab (targeting the p40 subunit of IL23), guselkumab, tildrakizumab, BI-655066 or LY-3074828 (targeting the p19 subunit of IL23), an antigen-binding fragment thereof, or a combination thereof. In other aspects, the IL23 antagonist is a molecule (e.g., an antibody) competing for binding to IL23 with an antibody selected from ustekinumab or briakinumab (targeting the p40 subunit of IL23), guselkumab, tildrakizumab, BI-655066 or LY-3074828 (targeting the p19 subunit of IL23), an antigen-binding fragment thereof, or a combination thereof This finding can be applied, for example, to devise new methods of determining treatment (e.g., by selecting patients as candidates for a certain therapy), methods of treating an IL-23-mediated disease, methods of monitoring efficacy of therapeutic agents (e.g., anti-IL23 antibodies) to treat IL23-mediated diseases and disorders, or methods to adjust formulations, dosage regimens, or routes of administration.

The methods disclosed herein include prescribing, initiating, and/or altering prophylaxis and/or treatment, e.g., for an IL23-mediated disease such as CD, based at least in part on a subject's expression level of one or more IL23 pathway biomarkers. In a particular aspect, such IL23 pathway biomarkers are IL22 and/or LCN2.

The present disclosure provides a method of determining whether to treat a patient having an IL23-mediated disease or disorder with a therapeutic regimen comprising the administration of an IL23 antagonist (e.g., an anti-IL23 antibody targeting, e.g., the p19 subunit of IL23, such as MEDI2070, or an antigen-binding fragment thereof) wherein the method comprises: (a) measuring or instructing a clinical laboratory to measure the level of at least one IL23 pathway biomarker in a sample taken from the patient, and (b) treating or instructing a healthcare provider to treat the patient, or suspending the treatment, not initiating the treatment, denying the treatment, or instructing a healthcare provider to suspend, not initiate, or deny the treatment with a therapeutic regimen comprising the administration of an IL23 antagonist (e.g., an anti-IL23 antibody targeting, e.g., the p19 subunit of IL23, such as MEDI2070, or an antigen-binding fragment thereof) if the patient is determined to have a higher or lower level of the at least one IL23 pathway biomarker in the sample compared to a predetermined threshold level, or compared to a level in one or more control samples.

In one aspect, the disclosure provides a method of determining whether to treat a patient having an IL23-mediated disease or disorder with a therapeutic regimen comprising the administration of an IL23 antagonist (e.g., an anti-IL23 antibody targeting, e.g., the p19 subunit of IL23, such as MEDI2070, or an antigen-binding fragment thereof) wherein the method comprises: (a) measuring or instructing a clinical laboratory to measure the levels of IL22 and/or LCN2 in a sample taken from the patient, and (b) treating or instructing a healthcare provider to treat the patient with a therapeutic regimen comprising the administration of an antibody or antigen-binding fragment thereof that specifically binds to IL23 if the patient is determined to have (i) a higher or increased level of IL22, and/or (ii) a higher or increased level of LCN2 in the sample compared to a predetermined IL22 and/or LCN2 threshold level, or compared to IL22 and/or LCN2 level in one or more control samples.

In one aspect, the disclosure provides a method of determining whether to treat a patient having an IL23-mediated disease or disorder with a therapeutic regimen comprising the administration of an IL23 antagonist (e.g., an anti-IL23 antibody targeting, e.g., the p19 subunit of IL23, such as MEDI2070, or an antigen-binding fragment thereof) wherein the method comprises (a) measuring or instructing a clinical laboratory to measure the levels of IL22 and/or LCN2 in a sample taken from the patient, and (b) suspending the treatment, not initiating treatment, denying the treatment, or instructing a healthcare provider to suspend, not initiate, or deny the treatment of the patient with a therapeutic regimen comprising the administration of an antibody or antigen-binding fragment thereof that specifically binds to IL23 to the patient if the patient is determined to have (i) a lower or decreased level of IL22, and/or (ii) a lower or decreased level of LCN2 in the sample compared to a predetermined IL22 and/or LCN2 threshold level, or compared to a IL22 and/or LCN2 level in one or more control samples.

Also provided is a method of selecting a patient diagnosed with an IL23-mediated disease or disorder as a candidate for treatment with an IL23 antagonist (e.g., an anti-IL23 antibody targeting, e.g., the p19 subunit of IL23, such as MEDI2070, or an antigen-binding fragment thereof), comprising (a) measuring or instructing a clinical laboratory to measure the levels of IL22 and/or LCN2 in a sample taken from the patient, and (b) treating or instructing a healthcare provider to treat the patient with an IL23 antagonist (e.g., an anti-IL23 antibody targeting, e.g., the p19 subunit of IL23, such as MEDI2070, or an antigen-binding fragment thereof) if the patient is determined to have (i) a higher or increased level of IL22, and/or (ii) a higher or increased level of LCN2 in the sample compared to a predetermined IL22 and/or LCN2 threshold level, or compared to IL22 and/or LCN2 level in one or more control samples.

Also provided is method of selecting a patient diagnosed with an IL23-mediated disease or disorder as a candidate for treatment with an IL23 antagonist (e.g., an anti-IL23 antibody targeting, e.g., the p19 subunit of IL23, such as MEDI2070, or an antigen-binding fragment thereof), comprising (a) measuring or instructing a clinical laboratory to measure the levels of IL22 and/or LCN2 in a sample taken from the patient, and (b) suspending the treatment, not initiating treatment, denying the treatment, or instructing a healthcare provider to suspend, not initiate, or deny the treatment of the patient with an IL23 antagonist (e.g., an anti-IL23 antibody targeting, e.g., the p19 subunit of IL23, such as MEDI2070, or an antigen-binding fragment thereof) to the patient if the patient is determined to have (i) a lower or decreased level of IL22, and/or (ii) a lower or decreased level of LCN2 in the sample compared to a predetermined IL22 and/or LCN2 threshold level, or compared to a IL22 and/or LCN2 level in one or more control samples.

In some aspects, the methods disclosed can entail ordering and/or performing one or more additional assays. For example, if the IL22 and/or LCN2 level (e.g., a protein expression level or a gene expression level) is determined to be within a normal range (i.e., not elevated), the IL22 and/or LCN2 assay may be repeated to rule out a false negative result, and/or one or more additional IL22 and/or LCN2 assays may be performed to monitor the subject's status. Conversely, if the IL22 and/or LCN2 level (e.g., a protein expression level or a gene expression level) is determined to be elevated, it may be desirable repeat the IL22 and/or LCN2 assay to rule out a false positive result.

In some aspects, the predetermined IL22 threshold level is at least about 15.6 pg/mL as measured in serum using an IL22 immunoassay (including, e.g., the IL22 immunoassay described in Example 3); and/or the predetermined LCN2 threshold level is at least about 215 ng/mL as measured in serum using an LCN2 immunoassay (including, e.g., the LCN2 immunoassay described in Example 3).

In some aspects, the presence of IL23 pathway biomarker levels (e.g., IL22 and/or LCN2 levels) above or below a predetermined threshold level in a patient with an IL23-mediated disease can be used in combination with one or more of biomarkers specific for such disease. For example, for patients with inflammatory bowel disease (IBD) (including, e.g., CD or UC), the measurement of IL23 pathway biomarker levels (e.g., IL22 and/or LCN2 levels) can be combined with measurements of biomarkers such as C-reactive protein (CRP) and/or calprotectin levels. Accordingly, in one aspects, levels of IL22 and/or LCN2 can be combined with CRP and/or calprotectin levels in any of the methods disclosed herein (i) to determine whether a patient suffering an IL23-mediated disease (e.g., IBD, CD or UC) is eligible or non-eligible for a specific treatment or will respond to a specific treatment with an IL23 antagonist (e.g., an anti-IL23 antibody targeting, e.g., the p19 subunit of IL23, such as MEDI2070, or an antigen-binding fragment thereof), (ii) to determine whether a specific treatment (e.g., with an IL23 antagonist such as MEDI2070) should commence, be suspended, or be modified, (iii) to diagnose whether the disease (e.g., IBD, CD or UC) is treatable or not treatable with a specific therapeutic agent, or (iv) to prognosticate or predict the outcome of treatment of the disease (e.g., IBD, CD or UC) with a specific therapeutic agent, etc. if CRP and/or calprotectin levels are high. In some aspects, mean levels of C-reactive protein are high or elevated (and thus indicative of having active disease) if they are ≥5 mg/L as measured using an assay suitable for measuring CRP levels in a patient, including, e.g., the Dade Behring hs-CRP immunoturbidometric assay following the manufacturer's instructions. In some aspects, mean levels of fecal calprotectin are high or elevated (and thus indicative of having active disease) if they are ≥250 µg/g as measured using an assay suitable for measuring fecal calprotectin levels in a patient, including, e.g., Phadia ELIA™ Calprotectin assay following the manufacturer's instructions. In other aspects, mean levels of C-reactive protein are high or elevated if they are at least about 2, 3, 4, 5, 6, 7, 8, 9 or 10 mg/L as measured using an assay suitable for measuring CRP levels in a patient, including, e.g., the Dade Behring hs-CRP immunoturbidometric assay following the manufacturer's instructions. In some aspects, mean levels of fecal calprotectin are high or elevated if they are at least 150, 160, 170, 180, 190, 200, 210, 220, 230, 240, 250, 260, 270, 280, 290, 300, 310, 320, 330, 340 or 350 µg/g as measured using an assay suitable for measuring calprotectin levels in a patient, including, e.g., the Phadia ELIA™ Calprotectin assay following the manufacturer's instructions. In some aspects, the levels of fecal calprotectin are high or elevated if they are ≥250 µg/g, ≥200 µg/g, ≥150 µg/g, ≥100 µg/g, or at least about 100 g/g to at least about 250 µg/g as measured using an assay suitable for measuring calprotectin levels in a patient, including, e.g., the Phadia E<small>LI</small>A™ Calprotectin assay following the manufacturer's instructions. A person skilled in the art would appreciate that different methods to quantify C-reactive protein or calprotectin can be applied in the methods disclosed herein. See, e.g., U.S. Pat. No. 8,541,180; U.S. Pat. Appl. Publ. Nos. US20140227725 or US20140227725; and PCT Publ. Nos. WO2012175616, WO2010062663, WO2012175602, WO2013132338, or WO2013132347, which are herein incorporated by reference in their entireties.

A person skilled in the art would understand that IL22 and/or LCN2 levels (e.g., a protein expression level or a gene expression level) can be used according to the methods disclosed herein, including but not limited to treatment, diagnostic, and monitoring methods, as positive selectors, i.e., a specific action would be taken (e.g., treating a patient having an IL23-mediated disease with an IL23 antagonist) if the IL22 and/or LCN2 levels (e.g., a protein expression level or a gene expression level) in a sample taken from the patient are above predetermined IL22 and/or LCN2 threshold level, or are elevated relative to the IL22 and/or LCN2 levels in one or more control samples.

A person skilled in the art would also understand that IL22 and/or LCN2 levels (e.g., a protein expression level or a gene expression level) can be used according to the methods disclosed herein, including but not limited to treatment, diagnostic, and monitoring methods, as negative selectors, i.e., a specific action would not be taken (e.g., treating a patient having an IL23-mediated disease with an IL23 antagonist) if the IL22 and/or LCN2 levels (e.g., a protein expression level or a gene expression level) in a sample taken from the patient are below predetermined IL22 and/or LCN2 threshold level, or are low relative to the IL22 and/or LCN2 levels in one or more control samples.

In one aspect, the disclosure includes methods, assays, and kits to facilitate a determination by a healthcare provider, a healthcare benefits provider, or a clinical laboratory to as to whether a patient will benefit from treatment with an IL23 antagonist (e.g., an anti-IL23 antibody targeting, e.g., the p19 subunit of IL23, such as MEDI2070, or an antigen-binding fragment thereof).

The methods assays and kits provided herein also facilitate a determination by a healthcare provider, a healthcare benefits provider, or a clinical laboratory to as to whether a patient will benefit from treatment with any other IL23 antagonist (e.g., an anti-IL23 antibody targeting, e.g., the p19 subunit of IL23, such as MEDI2070, or an antigen-binding fragment thereof) disclosed herein or known to those of ordinary skill in the art.

In one aspect, the methods disclosed herein include making a diagnosis, which may be a differential diagnosis, based at least in part on the levels of IL22 and/or LCN2 of a patient. In some aspects, the methods disclosed herein include informing the subject of a result of the IL22 and/or LCN2 assay and/or of a diagnosis based at least in part on the IL22 and/or LCN2 level. The patient can be informed verbally, in writing, and/or electronically.

This diagnosis can also be recorded in a patient medical record. For example, in various aspects, the diagnosis of an IL23-mediated disease (e.g., CD) treatable with a specific IL23 antagonist (e.g., an anti-IL23 antibody targeting, e.g., the p19 subunit of IL23, such as MEDI2070, or an antigen-binding fragment thereof) is recorded in a medical record. The term "medical record" or "patient medical record" refers to an account of a patient's examination and/or treatment that typically includes one or more of the following: the patient's medical history and complaints, the physician's physical findings, the results of diagnostic tests and procedures, and patient medications and therapeutic procedures. A medical record is typically made by one or more physicians and/or physicians' assistants and it is a written, transcribed or otherwise recorded record and/or history of various illnesses or injuries requiring medical care, and/or inoculations, and/or allergies, and/or treatments, and/or prognosis, and/or frequently health information about parents, siblings, and/or occupation. The record may be reviewed by a physician in diagnosing the condition.

The medical record can be in paper form and/or can be maintained in a computer-readable medium. The medical record can be maintained by a laboratory, physician's office, a hospital, a healthcare maintenance organization, an insurance company, and/or a personal medical record website. In some aspects, a diagnosis, based at least in part on the IL22 and/or LCN2 level, is recorded on or in a medical alert article such as a card, a worn article, and/or a radiofrequency identification (RFID) tag. As used herein, the term "worn article" refers to any article that can be worn on a subject's body, including, but not limited to, a tag, bracelet, necklace, arm band, or head band.

As used herein, the term "diagnosis" means detecting a disease or determining the stage or degree of a disease. Usually, a diagnosis of a disease is based on the evaluation of one or more factors and/or symptoms that are indicative of the disease. That is, a diagnosis can be made based on the presence, absence or amount of a factor which is indicative of presence or absence of the disease or disorder. Each factor or symptom that is considered to be indicative for the diagnosis of a particular disease does not need be exclusively related to the particular disease, e.g. there may be differential diagnoses that can be inferred from a diagnostic factor or symptom. Likewise, there may be instances where a factor or symptom that is indicative of a particular disease is present in an individual that does not have the particular disease. The term "diagnosis" also encompasses determining the therapeutic effect of a drug therapy, or predicting the pattern of response to a drug therapy. The diagnostic methods may be used independently, or in combination with other diagnosing and/or staging methods known in the medical arts for a particular disease.

As used herein, the term "differential diagnosis" refers to the determination of which of two or more diseases with similar symptoms is likely responsible for a subject's symptom(s), based on an analysis of the clinical data. The term is also used to refer to the determination of whether a patient is susceptible to treatment with an IL23 antagonist (e.g., an anti-IL23 antibody targeting, e.g., the p19 subunit of IL23, such as MEDI2070, or an antigen-binding fragment thereof) depending on whether the measured IL22 and/or LCN2 levels in a patient sample are above a predetermined threshold level, or elevated relative to the level in one or more control samples.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average remission rate, a lower propensity for metastasis, a longer than expected life expectancy, differentiation of a benign process from a cancerous process, and the like.

The disclosure includes methods of treating an IL23-mediated mediated disease in a subject based on the changes in expression of IL23 pathway biomarkers, for example, IL22 and/or LCN2. The disclosure provides a method of treating a patient having an IL23-mediated disease or disorder, comprising: administering an IL23 antagonist (e.g., an anti-IL23 antibody targeting, e.g., the p19 subunit of IL23, such as MEDI2070, or an antigen-binding fragment thereof) to the patient if the patient is determined to have (i) a higher or increased level of IL22 and/or (ii) a higher or increased level of LCN2 in one or more samples taken from the patient compared to a predetermined IL22 and/or LCN2 threshold level, or compared to IL22 and/or LCN2 level in one or more control samples. In some aspects, a sample is obtained from a patient and is submitted for measurement of the level of IL22 and/or LCN2 in the sample.

The disclosure also provides a method of treating a patient having an IL23-mediated disease or disorder comprising: (a) submitting a sample taken from the patient for measurement of the levels of IL22 and/or LCN2 in the sample, and (b) administering an antibody or antigen-binding fragment thereof that specifically binds to IL23 (e.g., to the p19 subunit of IL23, such as MEDI2070) to the patient if the patients has (i) a higher or increased level of IL22 and/or (ii) a higher or increased level of LCN2 in the samples taken compared to a predetermined IL22 and/or LCN2 threshold level, or compared to IL22 and/or LCN2 level in one or more control samples.

Also provided is method of treating a patient having an IL23-mediated disease or disorder comprising: (a) submitting a sample taken from the patient for measurement of the levels of IL22 and/or LCN2 in the sample, and (b) suspending or not initiating the administration of an antibody or antigen-binding fragment thereof that specifically binds to IL23 (e.g., to the p19 subunit of IL23, such as MEDI2070) to the patient if the patients has (i) a lower or decreased level of IL22 and/or (ii) a lower or decreased level of LCN2 in the sample compared to a predetermined IL22 and/or LCN2 threshold level, or compared to IL22 and/or LCN2 level in one or more control samples.

The disclosure also provides a method of treating a patient having an IL23-mediated disease or disorder comprising: (a) measuring the levels of IL22 and/or LCN2 in a sample obtained from the patient; (b) determining the level of IL22 and/or LCN2 in the sample, and, (c) advising a healthcare provider to administer an antibody or antigen-binding fragment thereof that specifically binds to IL23 (e.g., to the p19 subunit of IL23, such as MEDI2070) to the patient if the patient is determined to have (i) a higher or increased level of IL22 and/or (ii) a higher or increased level of LCN2 in the sample compared to a predetermined IL22 and/or LCN2 threshold level, or compared to IL22 and/or LCN2 levels in one or more control samples; or to suspend or deny the administration of an antibody or antigen-binding fragment thereof that specifically binds to IL23 to the patient if the patient is determined to have (i) a lower or decreased level of IL22 and/or (ii) a lower or decreased level of LCN2 in the sample compared to a predetermined IL22 and/or LCN2 threshold level, or compared to IL22 and/or LCN2 level in one or more control samples.

Also provided is a method of treating a patient having an IL23-mediated disease or disorder comprising: (a) submitting a sample taken from a patient for measurement of the levels IL22 and/or LCN2 in a sample obtained from the patient, and (b) administering an antibody or antigen-binding fragment thereof that specifically binds to IL23 (e.g., to the p19 subunit of IL23, such as MEDI2070) to the patient if the patient is determined to have (i) a higher or increased level of IL22 and/or (ii) a higher or increased level of LCN2 in the sample compared to a predetermined IL22 and/or LCN2 threshold level, or compared to IL22 and/or LCN2 level in one or more control samples; or suspending, not initiating, or denying the administration of an antibody or antigen-binding fragment thereof that specifically binds to IL23 (e.g., to the p19 subunit of IL23, such as MEDI2070) to the patient if the patient is determined to have (i) a lower or reduced level of IL22 and/or (ii) a lower or reduced level of LCN2 in the sample compared to a predetermined IL22 and/or LCN2 threshold level, or compared to a IL22 and/or LCN2 level in one or more control samples.

In some aspects, the method comprises administering to the subject an effective amount of an IL23 antagonist (e.g., an anti-IL23 antibody targeting, e.g., the p19 subunit of IL23, such as MEDI2070, or an antigen-binding fragment thereof). In some aspects, the IL23-mediated disease is a pulmonary disease, an inflammatory bowel disease, a chronic inflammatory skin disease, an inflammatory disease, an autoimmune disease, a neurodegenerative disease, an infection, or a cancer. In some aspects, the IL23-mediated disease or disorder is selected from the group consisting of: asthma, IPF, COPD. Crohn's disease, ulcerative colitis (UC), celiac disease, atopic dermatitis, allergic contact dermatitis, eczema, psoriasis, alopecia areata, palmoplantar pustulosis, psoriatic arthritis, anklyosing spondylitis, arthritis, rheumatoid arthritis (RA), a rheumatic disorder, ANCA vasculitis, Bechet's disease, autoimmune thyroiditis, type 1 diabetes, multiple sclerosis (MS), Sjogren's syndrome (SS), systemic lupus erythematosus (SLE), Alzheimer's disease, mycobacterial disease, leishmaniasis, a fungal infection, a viral infection, gastric cancer, colorectal cancer, esophageal cancer, leukemia, hepatitis B virus (HBV)-related hepatocellular carcinoma, breast cancer, lung cancer, and nasopharyngeal cancer. In some aspects, the patient's IL22 and/or LCN2 levels are measured in an immunoassay as described herein employing one or more anti-IL22 and/or anti-LCN2 antibodies or antigen binding fragments thereof which recognize human IL22 or human LCN2 or antigen-binding fragments, variants or derivatives thereof. In some aspects, the sample is obtained from the patient and is submitted for measurement of the level of IL22 and/or LCN2 in the sample, for example, to a clinical laboratory.

In some aspects of the above treatment methods, the patient's IL22 and/or LCN2 levels (e.g., DNA or RNA level) are measured in an assay employing one or more oligonucleotide probes capable of specifically measuring the expression levels of the IL22 and/or LCN2 gene.

In some aspects, the IL22 and/or LCN2 detection assay (e.g., an immunoassay) is performed on a sample obtained from the patient, by the healthcare professional treating the patient (e.g., using an immunoassay as described herein including, e.g., the immunoassays described in Example 3, formulated as a "point of care" diagnostic kit). In some aspects, a sample is obtained from the patient and is submitted, e.g., to a clinical laboratory, for measurement of the IL22 and/or LCN2 level in the sample according to the healthcare professional's instructions (e.g., using an immunoassay as described herein including, e.g., the immunoassays described in Example 3). In some aspects, the clinical laboratory performing the assay will advise the healthcare provide as to whether the patient can benefit from treatment with an IL23 antagonist (e.g., an anti-IL23 antibody targeting, e.g., the p19 subunit of IL23, such as MEDI2070, or an antigen-binding fragment thereof) based on whether the patient's IL22 and/or LCN2 level is above a predetermined IL22 and/or LCN2 threshold value or is elevated relative to one or more control samples.

The disclosure also provides a method of measuring the efficacy or pharmacodynamics of an antibody or antigen-binding fragment thereof that specifically binds to IL23 (e.g., to the p19 subunit of IL23, such as MEDI2070) in a patient diagnosed with an IL23 mediated disease or disorder, comprising: (a) conducting a first measurement of the levels of IL22 and/or LCN2 in a first sample taken from the patient; (b) administering an antibody or antigen-binding fragment thereof that specifically binds to IL23 (e.g., to the p19 subunit of IL23, such as MEDI2070); and (c) conducting a second measurement of the levels of IL22 and/or LCN2 in a second sample taken from the patient, wherein a reduction in the level of IL22 and/or LCN2 in the second measurement compared to the patient's level IL22, and/or LCN2 level in the first measurement as measured from the patient's serum using an immunoassay described in Example 3 indicates that the patient is responding to treatment with the IL23 antibody or antigen-binding fragment thereof that specifically binds to IL23 (e.g., to the p19 subunit of IL23, such as MEDI2070).

In some aspects, the second measurement is conducted 1, 2, 4, 8, 12, or 28 weeks, or at intervening times, after administering the IL23 antibody or antigen-binding fragment thereof that specifically binds to IL23 (e.g., to the p19 subunit of IL23, such as MEDI2070).

In some aspects, this disclosure includes a method of treating a patient having an IL23-mediated disease over a period of time, comprising: measuring a first IL22 and/or LCN2 level (e.g., protein expression level or gene expression level) in a first sample taken from the patient, or submitting a first sample taken from the patient for measurement of a first IL22 and/or LCN2 level in the sample, wherein the patient's IL22 and/or LCN2 level is, for example, measured in an immunoassay, including, e.g., an immunoassay described in Example 3, employing one or more anti-IL22 and/or anti-LCN2 antibodies or antigen binding fragments thereof which recognize human IL22 and/or LCN2, and administering an IL23 antagonist (e.g., an anti-IL23 antibody targeting, e.g., the p19 subunit of IL23, such as MEDI2070, or an antigen-binding fragment thereof) to the patient if the patient's IL22 and/or LCN2 level in the first sample is above a predetermined IL22 and/or LCN2 threshold level, or is elevated relative to the IL22 and/or LCN2 level in one or more control samples. The test can be performed by a healthcare provider or a clinical laboratory as noted above.

According to these aspects, the method can further comprise: measuring a second IL22 and/or LCN2 level (e.g., protein expression level or gene expression level) in a second sample taken from the patient, or submitting a second sample taken from the patient for measurement of a second IL22 and/or LCN2 level in the sample, wherein the patient's IL22 and/or LCN2 level is again measured, for example, in an immunoassay, including, e.g., an immunoassay described in Example 3, employing one or more anti-IL22 and/or anti-LCN2 antibodies or antigen binding fragments thereof which recognize human IL22 and/or human LCN2; comparing the first and second IL22 and/or LCN2 levels in the patient, and altering the dose, e.g., increasing or maintaining the amount or frequency of the IL23 antagonist administered to the patient (e.g., an anti-IL23 antibody targeting, e.g., the p19 subunit of IL23, such as MEDI2070, or an antigen-binding fragment thereof). In some aspects, IL23 antagonist therapy can be discontinued if, e.g., the patient's IL22 and/or LCN2 level in the second sample is higher than the IL22 and/or LCN2 level in the first sample.

In some aspects, the amount or frequency of the IL23 antagonist administered to the patient (e.g., an anti-IL23 antibody targeting, e.g., the p19 subunit of IL23, such as MEDI2070, or an antigen-binding fragment thereof) can be maintained or reduced if the patient's IL22 and/or LCN2 level in the second sample is lower than or about the same as the IL22 and/or LCN2 level in the first sample.

In certain aspects, in all the treatment methods disclosed herein, a "loading" dose of an IL23 antagonist (e.g., an anti-IL23 antibody targeting, e.g., the p19 subunit of IL23, such as MEDI2070, or an antigen-binding fragment thereof) is administered to achieve a desired therapeutic level in the patient. If the loading dose does not affect the patient's IL22 and/or LCN2 levels (e.g., protein expression levels or gene expression levels) significantly or the patient's IL22 and/or LCN2 levels rise, a decision could be made to discontinue treatment—e.g., to use a non-IL23 antagonist therapy.

If the loading dose results in a reduced IL22 and/or LCN2 level in the patient a decision could be made to reduce the dose size or frequency to a "maintenance" dose. It is important to note that the methods provided here are guidelines for a healthcare provider to administer treatment, and the ultimate treatment decision will be based on the healthcare provider's sound judgment.

In some aspects, results of an immunoassay as provided herein can be submitted to a healthcare benefits provider for determination of whether the patient's insurance will cover treatment with an IL23 antagonist (e.g., an anti-IL23 antibody targeting, e.g., the p19 subunit of IL23, such as MEDI2070, or an antigen-binding fragment thereof).

In some aspects, this disclosure includes a method of treating a patient having an IL23-mediated disease comprising: measuring, e.g., in a clinical laboratory, the IL22 and/or LCN2 level (e.g., protein expression level or gene expression level) in a first sample obtained from a patient having an IL23-mediated disease, e.g., a sample provided by a healthcare provider, wherein the patient's IL22 and/or LCN2 level in the first sample is, for example, measured in an immunoassay, including, e.g., an immunoassay described in Example 3, employing one or more anti-IL22 and/or anti-LCN2 antibodies or antigen binding fragments thereof which recognize human IL22 and/or human LCN2, determining whether the patient's IL22 and/or LCN2 level in the first sample is above a predetermined IL22 and/or LCN2 level, or is elevated relative to the IL22 and/or LCN2 level in one or more control samples; and advising a healthcare provider to administer an IL23 antagonist (e.g., an anti-IL23 antibody targeting, e.g., the p19 subunit of IL23, such as MEDI2070, or an antigen-binding fragment thereof) to the patient if the patient's IL22 and/or LCN2 level are above a predetermined IL22 and/or LCN2 threshold level, or are elevated relative to the IL22 and/or LCN2 level in one or more control samples.

In some aspects, these methods can further comprise: measuring the IL22 and/or LCN2 levels (e.g., protein expression level or gene expression level) in a second sample obtained from the patient, e.g., a sample provided by a healthcare provider, wherein the patient's IL22 and/or LCN2 level is again measured, for example, in an immunoassay, including, e.g., an immunoassay described in Example 3, employing one or more anti-IL22 and/or anti-LCN2 antibodies or antigen binding fragments thereof which recognize human IL22 and/or human LCN2; determining whether the patient's IL22 and/or LCN2 level in the second sample is higher than, about the same as, or lower than the IL22 and/or LCN2 level measured in the first sample; and advising a healthcare provider to adjust the IL23 antagonist therapy (e.g., a therapy comprising the administration of an anti-IL23 antibody targeting, e.g., the p19 subunit of IL23, such as MEDI2070, or an antigen-binding fragment thereof) if indicated, e.g., to increase or maintain the amount or frequency of the IL23 antagonist administered to the patient, or discontinuing IL23 antagonist therapy, if the patient's IL22 and/or LCN2 level in the second sample is higher than the IL22 and/or LCN2 level in the first sample, or to maintain or reduce the amount or frequency of the IL23 antagonist administered to the patient if the patient's IL22 and/or LCN2 level in the second sample is lower than or about the same as the IL22 and/or LCN2 level in the first sample.

In some aspects, a sample is obtained from the patient and is submitted, e.g., to a clinical laboratory, for measurement of the IL22 and/or LCN2 level (e.g., protein expression level or gene expression level) in the sample, e.g., using an immunoassay. In some aspects, the clinical laboratory performing the assay will advise the healthcare provide as to whether the patient can benefit from treatment with an IL23 antagonist (e.g., an anti-IL23 antibody targeting, e.g., the p19 subunit of IL23, such as MEDI2070, or an antigen-binding fragment thereof) based on whether the patient's IL22 and/or LCN2 level (e.g., protein expression level or gene expression level) is above a predetermined IL22 and/or LCN2 threshold value or is elevated relative to one or more control samples.

In some aspects, methods of treatment contemplated herein (e.g., for an IL23-mediated disease such Crohn's disease) comprise administering to the subject an antibody or antigen-binding fragment thereof targeting IL23 (e.g., to the p19 subunit of IL23, such as MEDI2070) in a sufficient amount and/or at sufficient interval to achieve and/or maintain a certain quantity of IL23-specific antibody per volume of serum, using, for example, an assay as described herein.

For example, the antibody or antigen-binding fragment thereof targeting IL23 (e.g., to the p19 subunit of IL23, such as MEDI2070) can be given to achieve at least 25 ng/ml, 30 ng/ml, 35 ng/ml. 40 ng/ml, 45 ng/ml, 50 ng/ml, 55 ng/ml, 60 ng/ml, 65 ng/ml, 70 ng/ml, 75 ng/ml, 80 ng/ml, 85 ng/ml, 90 ng/ml, 95 ng/ml, 100 ng/ml, 150 ng/ml, 200 ng/ml, 250 ng/ml, 300 ng/ml, 350 ng/ml, 400 ng/ml, 450 ng/ml, 500 ng/ml, 550 ng/ml, 600 ng/ml, 650 ng/ml, 700 ng/ml, 750 ng/ml, 800 ng/ml, 850 ng/ml, 900 ng/ml, 950 ng/ml or 1000 ng/ml in serum.

In a further embodiment, the antibody or antigen-binding fragment thereof targeting IL23 (e.g., to the p19 subunit of IL23, such as MEDI2070) can be given to achieve a concentration of IL23-specific antibody in serum from about 12.5 ng/ml to about 1000 ng/ml. Those of skill in the art will understand that the amounts given here apply to a full-length antibody or immunoglobulin molecule; if an antigen binding fragment thereof is used, the absolute quantity will differ from that given in a manner that can be calculated based on the molecular weight of the fragment.

In some aspects, methods of treatment contemplated herein (e.g., for an IL23-mediated disease such as Crohn's disease) comprise administering to the subject an IL23 antagonist (e.g., an anti-IL23 antibody targeting, e.g., the p19 subunit of IL23, such as MEDI2070, or an antigen-binding fragment thereof) in an amount and at an interval of: 15-54 mg every 0.5-1.5 months; 55-149 mg every 1.5-4.5 months; 150-299 mg every 4-8 months; or 300-1100 mg every 4-12 months. In some aspects, the amount and interval are: 15-21 mg every 0.5-1.0 month; 55-70 mg every 1.5-3.0 months; 150-260 mg every 4-6 months; or 300-700 mg every 4-8 months. In some aspects, the amount and interval are: 21 mg every month; 70 mg every 3 months; 210 mg every 6 months; or 700 mg every 6 months. In some aspects, the amount and interval are: 210 mg every 3 months or 700 mg every 3 months. In some aspects, the amount and interval are: 210 mg every 1 month or 700 mg every 1 month.

In some aspects of the methods, the IL23 antagonist (e.g., an anti-IL23 antibody targeting, e.g., the p19 subunit of IL23, such as MEDI2070, or an antigen-binding fragment thereof) is administered intravenously (IV). In some aspects of the methods, the IL23 antagonist (e.g., an anti-IL23 antibody targeting, e.g., the p19 subunit of IL23, such as MEDI2070, or an antigen-binding fragment thereof) is administered subcutaneously (SC).

In some aspects, the IL23 antagonist (e.g., an anti-IL23 antibody targeting, e.g., the p19 subunit of IL23, such as MEDI2070, or an antigen-binding fragment thereof) is administered in one or more fixed doses. In some aspects, the doses as administered every week, every two weeks, every three weeks, every 4 weeks, every 5 weeks, every 6 weeks, every 7 weeks, every 8 weeks, every 9 weeks every 10 weeks, or every 12 weeks. In some aspects, the dose comprises about 1 mg, 2 mg, 3 mg, 4 mg, 5 mg, 10 mg, 15 mg, 20 mg, 25 mg, 30 mg, 35 mg, 40 mg, 45 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, 500 mg, 510 mg, 520 mg, 530 mg, 540 mg, 550 mg, 560 mg, 570 mg, 580 mg, 590 mg, 600 mg, 610 mg, 620 mg, 630 mg, 640 mg, 650 mg, 660 mg, 670 mg, 680 mg, 690 mg, 700 mg, 710 mg, 720 mg, 730 mg, 740 mg, 750 mg, 760 mg, 770 mg, 780 mg, 790 mg, 800 mg, 810 mg, 820 mg, 830 mg, 840 mg, 850 mg, 860 mg, 870 mg, 880 mg, 890 mg, 900 mg, 910 mg, 920 mg, 930 mg, 940 mg, 950 mg, 960 mg, 970 mg, 980 mg, 990 mg or 1000 mg. In some aspects, the dose is higher than 1000 mg.

In some aspects, the dose is about 210 mg of IL23 antagonist (e.g., an anti-IL23 antibody targeting, e.g., the p19 subunit of IL23, such as MEDI2070, or an antigen-binding fragment thereof) administered SC.

In other aspects, the dose is about 700 mg of IL23 antagonist (e.g., an anti-IL23 antibody targeting, e.g., the p19 subunit of IL23, such as MEDI2070, or an antigen-binding fragment thereof) administered IV.

In some aspects, two, three, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 doses are administered.

In one specific aspect, the anti-IL23 antibody (e.g., MEDI2070) is administered at a fixed dose of 210 mg Q4W for 26 doses. In another specific aspects, the anti-IL23 antibody (e.g., MEDI2070) is administered at a fixed dose of 700 mg IV Q4W for 12-weeks. In some aspects, the IV administration is followed by administration of the anti-IL23 antibody (e.g., MEDI2070) at a fixed dose of 210 mg SC Q4W for 100-weeks.

The formulation, dosage regimen, and route of administration of a therapeutic agent, e.g., and IL23 antagonist (e.g., an anti-IL23 antibody targeting, e.g., the p19 subunit of IL23, such as MEDI2070, or an antigen-binding fragment thereof), can be adjusted to provide an effective amount for an optimum therapeutic response according to the method disclosed herein. With regard to the administration of an IL23 antagonist, the antagonist may be administered through any suitable means, compositions and routes known in the art. With regard to dosage regiments, a single bolus can be administered, several divided doses can be administered over time or the dose can be proportionally reduced or increased as indicated by the exigencies of the therapeutic situation.

The IL23 antagonist (e.g., an anti-IL23 antibody targeting, e.g., the p19 subunit of IL23, such as MEDI2070, or an antigen-binding fragment thereof) may be administered by any suitable technique, including but not limited to, parenterally, topically, or by inhalation. If injected, the pharmaceutical composition can be administered, for example, via intra-articular, intravenous, intramuscular, intralesional, intraperitoneal or cutaneous routes (including intra-, trans- or sub-dermal, and subcutaneous), by bolus injection, or continuous infusion. In some aspects, the pharmaceutical composition is administered by an intravenous route. In some aspects the pharmaceutical composition is administered by a subcutaneous route. In further aspects, the compositions are administered by oral, buccal, rectal, intratracheal, gastric, or intracranial routes. Localized administration, e.g. at a site of disease or injury is contemplated, for example, by enema or suppository for conditions involving the gastrointestinal tract. Also contemplated are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments, prefilled syringes and autoinjectors.

Advantageously, the IL23 antagonist (e.g., an anti-IL23 antibody targeting, e.g., the p19 subunit of IL23, such as MEDI2070, or an antigen-binding fragment thereof) can be administered in the form of a composition comprising one or more additional components such as a physiologically acceptable carrier, excipient or diluent. Optionally, the composition additionally comprises one or more physiologically active agents for combination therapy.

A pharmaceutical composition may comprise an IL23 antagonist (e.g., an anti-IL23 antibody targeting, e.g., the p19 subunit of IL23, such as MEDI2070, or an antigen-binding fragment thereof) together with one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrins, a chelating agent such as EDTA, glutathione, a stabilizer, and an excipient. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents.

In some aspects, the IL23 antagonist (e.g., an anti-IL23 antibody targeting, e.g., the p19 subunit of IL23, such as MEDI2070, or an antigen-binding fragment thereof) can be provided at a concentration of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 mg/ml.

Exemplary formulations useful for the present invention are those that include a glutamic acid, citric acid or acetic acid buffer at an appropriate pH, from 4.5 to 5.2, an excipient such as sucrose, glycine, proline, glycerol, and/or sorbitol at an appropriate concentration such as 1 to 20% (w/v), and a surfactant such as a non-ionic surfactant like polysorbate (polysorbate 20 or 80) or poloxamers (poloxamer 1888) at an appropriate concentration of 0.001%-0.1% (w/v). Such formulations are disclosed in U.S. Pat. No. 6,171,586 and WIPO Published Applications Nos. WO20100027766 and WO2011088120. In some aspects, the formulations comprise sodium acetate, sucrose and polysorbate 20. In some aspects, the formulations comprise 70 mg/mL anti-IL23 antibody (e.g., MEDI2070), 10 mM sodium acetate, 9% (w/v) sucrose and 0.004% (w/v) polysorbate 20, at pH 5.2. Suitable components are nontoxic to recipients at the dosages and concentrations employed. Further examples of components that may be employed in pharmaceutical formulations are presented in any Remington's Pharmaceutical Sciences including the $21^{st}$ Ed. (2005), Mack Publishing Company, Easton, Pa.

VI. Combination Treatments

Particular aspects of methods of the invention involve the use of an anti-IL23 antibody (e.g., an anti-IL23 antibody targeting, e.g., the p19 subunit of IL23, such as MEDI2070, or an antigen-binding fragment thereof) and one or more additional IL23 antagonists as described in the section of the description entitled "IL23 Antagonists" in combination with additional therapeutic agents.

In some aspects, the IL23 antagonist is an anti-IL23 antibody which can specifically bind to the p19 subunit of IL23 (SEQ ID NO: 13), to the p40 subunit of IL23 (SEQ ID NO: 14), or both.

In some aspects, the anti-IL23 antibody or antigen-binding fragment thereof comprises the heavy chain (HC) (SEQ ID NO: 15) and/or the light chain (SEQ ID NO: 16) of MEDI2070, or an antigen-binding fragment, variant, or derivative thereof. In some aspects, the anti-IL23 antibody or antigen-binding fragment thereof comprises the heavy chain variable region (VH) (SEQ ID NO: 5) and/or the light chain variable region (VL) (SEQ ID NO: 6) of MEDI2070. In some aspects, the anti-IL23 antibody or antigen-binding fragment thereof comprises at least one of the complementarity determining regions of MEDI2070 (SEQ ID NOS: 31-36). In some aspects, the anti-IL23 antibody or antigen-binding fragment thereof comprises a VH region comprising the sequence of SEQ ID NO: 43 and/or a VL region comprising the sequence of SEQ ID NO: 44, or an antigen-binding fragment, variant, or derivative thereof. In some aspects, the anti-IL23 antibody or antigen-binding fragment thereof comprises at least one of the complementarity determining regions of SEQ ID NOS:45-47 (CDRs of the VH of SEQ ID NO:43) and/or SEQ ID NOS: 48-50 (CDRs of the VL of SEQ ID NO:44).

In other aspects, the IL23 antagonist is an anti-IL23 antibody selected from ustekinumab or briakinumab (targeting the p40 subunit of IL23), guselkumab, tildrakizumab, BI-655066 or LY-3074828 (targeting the p19 subunit of IL23), an antigen-binding fragment thereof, or a combination thereof. In other aspects, the IL23 antagonist is a molecule (e.g., an antibody) that competes for binding to IL23 with ustekinumab or briakinumab (targeting the p40 subunit of IL23), guselkumab, tildrakizumab, BI-655066 or LY-3074828 (targeting the p19 subunit of IL23), an antigen-binding fragment thereof, or a combination thereof.

Examples include using combinations of an anti-IL23 antibody and one or more other therapeutic moiety having anti-inflammatory properties (for example, non-steroidal anti-inflammatory agents, steroids, and/or immunomodulators), or of an anti-IL23 antibody and one or more other treatments (e.g., surgery, ultrasound, or treatment effective to reduce inflammation). Useful agents that may be combined with an anti-IL23 antibody include those used to treat, for example, Crohn's disease or ulcerative colitis, such as aminosalicylate (for example, mesalamine or substances that are metabolized to mesalamine, including, for example, ASACOL®, SALOFALK®, PENTASA®, DIPENTUM®, COLAZIDE®, LIALDA® and ROWASA®), corticosteroids/glucocorticoids (including prednisolone methasulfobenzoate, tixocortol pivalate, fluticasone propionate, beclomethasone dipropionate, and budesonide), antibiotics such as metronidazole or ciprofloxacin (or other antibiotics useful for treating, for example, patients afflicted with fistulas), and immunosuppressives such as azathioprine (for example, IMURAN® and AZASAN®), 6-mercaptopurine (for example, PURINETHOL®), methotrexate (for example, TREXALL®, RHEUMATREX®), tacrolimus (for example, PROGRAF®) and cyclosporine (for example, GENGRAF®, NEORAL®, and SANDIMMUNE®). Such agent(s) may be administered orally or by another route, for example via suppository or enema, at dosages and intervals that are known in the art and described in the prescribing information.

Furthermore, IL23 antibodies or antibody derivatives, or the aforesaid combinations, can be used in conjunction with one or more molecules or other treatments, wherein the other molecule(s) and/or treatment(s) do not directly bind to or affect IL23, but which combination is effective for treating or preventing the condition being treated. For example, an anti-IL23 antibody can be used in combination with probiotic therapy, or other therapy used to restore or maintain normal gut flora, including gut flora transplant. In one embodiment, one or more of the molecule(s) and/or treatment(s) treats or prevents a condition that is caused by one or more of the other molecule(s) or treatment(s) in the course of therapy, e.g., nausea, fatigue, alopecia, cachexia, insomnia, etc. Such agent(s) or therapies may be administered by routes, and at dosages and intervals, that are known in the art and described in the prescribing information.

In some aspects, IL23 antibodies or antibody derivatives, or the aforesaid combinations, can be used in conjunction with one or more elemental diet treatment. See, e.g., Voitk et al. Arch Surg 107:329 (1973); Yamamoto et al. Int J Colorectal Dis 28:335-340 (2013).

Additional supportive therapies are included in possible combination treatment with IL23 antagonists (e.g., an anti-IL23 antibody targeting, e.g., the p19 subunit of IL23, such as MEDI2070, or an antigen-binding fragment thereof); such supportive therapies as (without limitation), analgesics, and anticholinergic and antidiarrheal agents. Combining such supportive therapies can be useful in the beginning of a treatment regimen in reducing a patient's symptoms and improving their quality of life. Supportive therapies include administering oral iron, folate, and vitamin $B_{12}$. Antidiarrheal agents include, but are not limited to diphenoxylate, codeine, loperamide, and anticholinergics (or pharmacological equivalents thereof), which can be administered to patients with mild disease to reduce the frequency of bowel movements and relive rectal urgency. Cholestyramine can be used in patients to prevent bile salt-induced colonic secretion in patients who have already undergone limited ileocolic resections. Anticholinergic agents include, but are not limited to, clidinium bromide, dicyclomine hydrochloride, tincture of belladonna and the like, and are useful to reduce abdominal cramps, pain and rectal urgency. Supportive or therapies may be administered by routes, and at dosages and intervals, that are known in the art and described in the prescribing information In every case where a combination of molecules and/or other treatments is used, the individual molecule(s) and/or treatment(s) can be administered in any order, over any length of time, which is effective, e.g., simultaneously, consecutively, or alternately. In one embodiment, the method of treatment comprises completing a first course of treatment with one molecule or other treatment before beginning a second course of treatment. The length of time between the end of the first course of treatment and beginning of the second course of treatment can be any length of time that allows the total course of therapy to be effective, e.g., seconds, minutes, hours, days, weeks, months, or even years.

VII. Kits and Assays for Detecting IL23 Pathway Biomarkers

This disclosure also provides kits for detecting IL23 pathway biomarkers, e.g., IL22, LCN2, or combinations thereof (e.g., protein expression level or gene expression level), for example, through an immunoassay method. Such kits can comprise containers, each with one or more of the various reagents (e.g., in concentrated form) utilized in the method, including, for example, one or more anti-IL22 and/or anti-LCN2 antibodies. One or more anti-IL22 antibodies and/or anti-LCN2 antibodies, e.g., capture antibodies, can be provided already attached to a solid support. One or more antibodies anti-IL22 antibodies and/or anti-LCN2 antibodies, e.g., detection antibodies, can be provided already conjugated to a detectable label, e.g., biotin or a ruthenium chelate.

The kit can also provide reagents for coupling a detectable label to an antibody (as well as the label itself), buffers, and/or reagents and instrumentation to support the practice of the assays provided herein. In certain aspects, a labeled secondary antibody can be provided that binds to the detection antibody. A kit provided according to this disclosure can further comprise suitable containers, plates, and any other reagents or materials necessary to practice the assays provided herein.

In some aspects, a kit comprises one or more nucleic acid probes (e.g., oligonucleotides comprising naturally occurring and/or chemically modified nucleotide units) capable of hybridizing a subsequence of the IL22 or LCN2 gene sequences under high stringency conditions. In some aspects, one or more nucleic acid probes (e.g., oligonucleotides comprising naturally occurring and/or chemically modified nucleotide units) capable of hybridizing a subsequence of the IL22 or LCN2 gene sequence under high stringency conditions are attached to a microarray chip.

A kit provided according to this disclosure can also comprise brochures or instructions describing the process. For IL22 or LCN2 detection immunoassays, and in particular sandwich immunoassays, e.g., an ELISA assay or an ECL assay, the sandwich immunoassay process comprises a first anti-IL22 or anti-LCN2 "capture" antibody or antigen-binding fragment thereof attached to a solid support, and a second anti-IL22 or anti-LCN2 "detection" antibody or antigen binding fragment thereof. The immunoassay can be performed by methods provided herein or methods well known and understood by those of ordinary skill in the art. In one aspect, the immunoassay comprises attaching a capture antibody or fragment thereof to a solid support; applying the test sample or a control sample, allowing IL22 or LCN2, if present in the sample, to bind to the capture antibody or fragment thereof; applying the detection antibody or fragment thereof, which can bind to IL22 or LCN2 already bound to the capture antibody or fragment thereof; and measuring the amount of detection antibody or fragment thereof bound to IL22 or LCN2. In certain aspects, the assay can further include washing steps, blocking steps and incubation steps.

Test kits can include instructions for carrying out one or more IL22 or LCN2 detection assays, e.g., immunoassays or nucleic acid detection assays. Instructions included in the kits can be affixed to packaging material or can be included as a package insert. While the instructions are typically written or printed materials they are not limited to such. Any medium capable of storing such instructions and communicating them to an end user is contemplated. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

VIII. Companion Diagnostic System

The methods disclosed herein can be provided as a companion diagnostic, for example available via a web server, to inform the clinician or patient about potential treatment choices. The methods disclosed herein can comprise collecting or otherwise obtaining a biological sample and performing an analytical method to detect and measure the levels of IL23 pathway biomarkers disclosed herein (e.g., protein expression levels or gene expression levels of IL22, LCN2, and/or combinations thereof) alone or in combination with other biomarkers (e.g., other components of the IL23 pathway, biomarkers downstream from the IL23 pathway, or components of inflammation pathways known in the art). Exemplary biomarkers that can be combined with IL22, LCN2, and combinations thereof are discussed above in the specification.

Levels of IL22, LCN2, and combinations thereof (e.g., protein expression levels or gene expression levels) or normalized scores derived from measured levels can be used alone (e.g., for treatment, diagnostic, prognostic, or monitoring purposes), or in combination with levels or normalized scores derived from other biomarkers (e.g., a panel a genes used to derive a gene signature). These scores can also be combined with other scores corresponding, for example, to clinical biomarkers such as (i) gender, (ii) age, (iii) body mass index, (iv) smoking status, (v) concomitant drugs, (vi) health assessment quality (HAQ), or a combination of two or more to yield a diagnostic score. In this approach, the diagnostic score may be a single number determined from the sum of all the marker calculations that is compared to a preset threshold value that is an indication of the presence or absence of disease. Or the diagnostic score may be a series of bars that each represent a biomarker value and the pattern of the responses may be compared to a pre-set pattern for determination of the presence or absence of disease.

At least some aspects of the methods described herein, due to the complexity of the calculations involved, a method comprising the use of IL22, LCN2, and combinations thereof as biomarkers can be implemented with the use of a computer. In some aspects, the computer system comprises hardware elements that are electrically coupled via bus, including a processor, input device, output device, storage device, computer-readable storage media reader, communications system, processing acceleration (e.g., DSP or special-purpose processors), and memory. The computer-readable storage media reader can be further coupled to computer-readable storage media, the combination comprehensively representing remote, local, fixed and/or removable storage devices plus storage media, memory, etc. for temporarily and/or more permanently containing computer-readable information, which can include storage device, memory and/or any other such accessible system resource.

A single architecture might be utilized to implement one or more servers that can be further configured in accordance with currently desirable protocols, protocol variations, extensions, etc. However, it will be apparent to those skilled in the art that embodiments may well be utilized in accordance with more specific application requirements. Customized hardware might also be utilized and/or particular elements might be implemented in hardware, software or both. Further, while connection to other computing devices such as network input/output devices (not shown) may be employed, it is to be understood that wired, wireless, modem, and/or other connection or connections to other computing devices might also be utilized.

In one aspect, the system further comprises one or more devices for providing input data to the one or more processors. The system further comprises a memory for storing a data set of ranked data elements. In another aspect, the device for providing input data comprises a detector for detecting the characteristic of the data element, e.g., such as a fluorescent plate reader, mass spectrometer, or gene chip reader.

The system additionally may comprise a database management system. User requests or queries can be formatted in an appropriate language understood by the database management system that processes the query to extract the relevant information from the database of training sets. The system may be connectable to a network to which a network server and one or more clients are connected. The network may be a local area network (LAN) or a wide area network (WAN), as is known in the art. Preferably, the server includes the hardware necessary for running computer program products (e.g., software) to access database data for processing user requests. The system can be in communication with an input device for providing data regarding data elements to the system (e.g., expression values). In one aspect, the input device can include a gene expression profiling system including, e.g., a mass spectrometer, gene chip or array reader, and the like.

Some aspects described herein can be implemented so as to include a computer program product. A computer program product may include a computer readable medium having computer readable program code embodied in the medium for causing an application program to execute on a computer with a database. As used herein, a "computer program product" refers to an organized set of instructions in the form of natural or programming language statements that are contained on a physical media of any nature (e.g., written, electronic, magnetic, optical or otherwise) and that may be used with a computer or other automated data processing system. Such programming language statements, when executed by a computer or data processing system, cause the computer or data processing system to act in accordance with the particular content of the statements.

Computer program products include without limitation: programs in source and object code and/or test or data libraries embedded in a computer readable medium. Furthermore, the computer program product that enables a computer system or data processing equipment device to act in pre-selected ways may be provided in a number of forms, including, but not limited to, original source code, assembly code, object code, machine language, encrypted or compressed versions of the foregoing and any and all equivalents.

In one aspect, a computer program product is provided to implemented the treatment, diagnostic, prognostic, or monitoring methods disclosed herein, for example, to determine whether to administer an IL23 antagonist (e.g., an anti-IL23 antibody targeting, e.g., the p19 subunit of IL23, such as MEDI2070, or an antigen-binding fragment thereof) to a patient in need thereof if the level of IL23 pathway biomarkers in a sample taken from the patient are above or below predetermined threshold levels, e.g., if IL22 and/or LCN2 levels are above respective predetermined threshold levels.

In some aspects, the IL23 antagonist is an anti-IL23 antibody which can specifically bind to the p19 subunit of IL23 (SEQ ID NO: 13), to the p40 subunit of IL23 (SEQ ID NO: 14), or both.

In some aspects, the anti-IL23 antibody or antigen-binding fragment thereof comprises the heavy chain (HC) (SEQ ID NO: 15) and/or the light chain (SEQ ID NO: 16) of MEDI2070, or an antigen-binding fragment, variant, or derivative thereof. In some aspects, the anti-IL23 antibody or antigen-binding fragment thereof comprises the heavy chain variable region (VH) (SEQ ID NO: 5) and/or the light chain variable region (VL) (SEQ ID NO: 6) of MEDI2070. In some aspects, the anti-IL23 antibody or antigen-binding fragment thereof comprises at least one of the complementarity determining regions of MEDI2070 (SEQ ID NOS: 31-36). In some aspects, the anti-IL23 antibody or antigen-binding fragment thereof comprises a VH region comprising the sequence of SEQ ID NO: 43 and/or a VL region comprising the sequence of SEQ ID NO: 44, or an antigen-binding fragment, variant, or derivative thereof. In some aspects, the anti-IL23 antibody or antigen-binding fragment thereof comprises at least one of the complementarity determining regions of SEQ ID NOS:45-47 (CDRs of the VH of SEQ ID NO:43) and/or SEQ ID NOS: 48-50 (CDRs of the VL of SEQ ID NO:44).

In other aspects, the IL23 antagonist is an anti-IL23 antibody selected from ustekinumab or briakinumab (targeting the p40 subunit of IL23), guselkumab, tildrakizumab, BI-655066 or LY-3074828 (targeting the p19 subunit of IL23), an antigen-binding fragment thereof, or a combination thereof. In other aspects, the IL23 antagonist is a molecule (e.g., an antibody) that competes for binding to IL23 with ustekinumab or briakinumab (targeting the p40 subunit of IL23), guselkumab, tildrakizumab, BI-655066 or LY-3074828 (targeting the p19 subunit of IL23), an antigen-binding fragment thereof, or a combination thereof.

The computer program product includes a computer readable medium embodying program code executable by a processor of a computing device or system, the program code comprising: (a) code that retrieves data attributed to a biological sample from a subject, wherein the data comprises IL23 pathway biomarker (e.g., IL22, and/or LCN2) levels values (presence/absence, amount, or data otherwise derived from these level values) alone or combination with values corresponding to other biomarkers in the biological sample (e.g., biological markers or clinical markers). These values can also be combined with values corresponding to clinical biomarkers, for example, indicative of the severity of the disease or disorder or to the patient's predisposition to have such disease or disorder; and, (b) code that executes a classification method that indicates, e.g., whether to administer an IL23 antagonist (e.g., an anti-IL23 antibody targeting, e.g., the p19 subunit of IL23, such as MEDI2070, or an antigen-binding fragment thereof) to a patient in need thereof.

While various aspects have been described as methods or apparatuses, it should be understood that aspects can be implemented through code coupled with a computer, e.g., code resident on a computer or accessible by the computer. For example, software and databases could be utilized to implement many of the methods discussed above. Thus, in addition to aspects accomplished by hardware, it is also noted that these aspects can be accomplished through the use of an article of manufacture comprised of a computer usable medium having a computer readable program code embodied therein, which causes the enablement of the functions disclosed in this description. Therefore, it is desired that aspects also be considered protected by this patent in their program code means as well.

Furthermore, some aspects can be code stored in a computer-readable memory of virtually any kind including, without limitation, RAM, ROM, magnetic media, optical media, or magneto-optical media. Even more generally, some aspects could be implemented in software, or in hardware, or any combination thereof including, but not limited to, software running on a general purpose processor, microcode, PLAs, or ASICs.

It is also envisioned that some aspects could be accomplished as computer signals embodied in a carrier wave, as well as signals (e.g., electrical and optical) propagated through a transmission medium. Thus, the various types of information discussed above could be formatted in a structure, such as a data structure, and transmitted as an electrical signal through a transmission medium or stored on a computer readable medium.

IX. Embodiments

E1. A method of treating an interleukin-23 (IL23)-mediated disease in a patient, comprising administering an IL23 antagonist to a patient if the patient is determined or identified to have (i) a higher or increased level of interleukin-22 (IL22) and/or (ii) a higher or increased level of lipocalin 2 (LCN2) in one or more samples taken from the patient compared to a predetermined IL22 and/or LCN2 threshold level, or compared to a IL22 and/or LCN2 level in one or more control samples.

E2. A method of treating a patient having an IL23-mediated disease comprising suspending or not initiating the administration of an IL23 antagonist to a patient if the is determined or identified to have (i) a lower or decreased level of interleukin-22 (IL22) and/or (ii) a lower or decreased level of lipocalin 2 (LCN2) in one or more samples taken from the patient compared to a predetermined IL22 and/or LCN2 threshold level, or compared to a IL22 and/or LCN2 level in one or more control samples.

E3. A method of treating an interleukin-23 (IL23)-mediated disease in a patient, wherein the patient failed, was non-responsive or intolerant to treatment with an anti-TNF agent comprising administering an IL23 antagonist to the patient if the patient is determined or identified to have (i) a higher or increased level of interleukin-22 (IL22) and/or (ii) a higher or increased level of lipocalin 2 (LCN2) in one or more samples taken from the patient compared to a predetermined IL22 and/or LCN2 threshold level, or compared to a IL22 and/or LCN2 level in one or more control samples.

E4. A method of determining whether to treat a patient having an IL23-mediated disease with an IL-23 antagonist, comprising determining to treat the patient if the patient is determined or identified to have (i) a higher or increased level of interleukin-22 (IL22) and/or (ii) a higher or increased level of lipocalin 2 (LCN2) in one or more samples taken from the patient compared to a predetermined IL22 and/or LCN2 threshold level, or compared to a IL22 and/or LCN2 level in one or more control samples.

E5. A method of selecting a patient diagnosed with an IL23-mediated disease as a candidate for treatment with an IL23 antagonist, comprising selecting the patient for treatment if the patient is determined or identified to have (i) a higher or increased level of interleukin-22 (IL22) and/or (ii) a higher or increased level of lipocalin 2 (LCN2) in one or more samples taken from the patient compared to a predetermined IL22 and/or LCN2 threshold level, or compared to a IL22 and/or LCN2 level in one or more control samples.

E6. The method according to any one of embodiments E1 to E5, further comprising measuring the level of IL22 and/or LCN2 in one or more of the samples obtained from the patient or instructing a clinical laboratory or healthcare provider to measure the level of IL22 and/or LCN2 in the sample and/or submitting the one or more samples obtained from the patient to a clinical laboratory or healthcare provider to measure the level of IL22 and/or LCN2 in the sample.

E7. The method according to any one of embodiments E1 to E6, further comprising determining the level of IL22 and/or LCN2 in the one or more samples obtained from the patient.

E8. The method according to any one of embodiments E1 to E7 further comprising advising a healthcare provider to administer an IL23 antagonist to the patient if the patient is determined or identified to have (i) a higher or increased level of IL22 and/or (ii) a higher or increased level of LCN2 in one or more of the samples compared to a predetermined IL22 and/or LCN2 threshold level, or compared to a IL22 and/or LCN2 level in one or more control samples, or to suspend, not initiate or deny the administration of an IL23 antagonist to the patient if the patient is determined or identified to have (i) a lower or decreased level of IL22 and/or (ii) a lower or decreased level of LCN2 in one or more of the samples compared to a predetermined IL22 and/or LCN2 threshold level, or compared to a IL22 and/or LCN2 level in one or more control samples E9. A method of measuring the efficacy or pharmacodynamics of an IL23 antagonist in a patient diagnosed with an IL23-mediated disease, comprising: (a) measuring the level of IL22 and/or LCN2 in a first sample taken from the patient; (b) administering an IL23 antagonist; and (c) measuring the level of IL22 and/or LCN2 in a second sample taken from the patient, wherein a reduction in the level of IL22 and/or LCN2 in the second sample compared to the patient's level IL22 and/or LCN2 in the first sample indicates that the patient is responding to treatment.

E10. The method according to embodiment E9, wherein the second sample is taken 1, 2, 4, 8, 12, or 28 weeks, or at intervening times, after administering the IL23 antagonist.

E11. The method according to any one of embodiments E1 to E10, wherein the IL23 antagonist is an anti-IL23 antibody or antigen-binding fragment thereof.

E12. The method of embodiment E11, wherein the anti-IL23 antibody or antigen-binding fragment thereof binds to the p19 subunit of IL23 (SEQ ID NO: 13), to the p40 subunit of IL23 (SEQ ID NO: 14), or both.

E13. The method according to any one of embodiments E11 or E12, wherein the anti-IL23 antibody or antigen-binding fragment thereof comprises ustekinumab, briakinumab, guselkumab, BI-655066, tildrakinumab, LY-3074828, or an antigen-binding fragment thereof.

E14. The method according to embodiment 11, wherein the anti-IL23 antibody or antigen-binding fragment thereof comprises (i) a variable region (VH) comprising or consisting of SEQ ID NO: 5 and/or a light chain variable region (VL) comprising or consisting of SEQ ID NO: 6, or (ii) a variable region (VH) comprising or consisting of SEQ ID NO: 43 and/or a light chain variable region (VL) comprising or consisting of SEQ ID NO: 44.

E15. The method according to embodiment 11, wherein the anti-IL23 antibody or antigen-binding fragment thereof comprises at least one, two, three, four, five or six complementarity determining regions selected from SEQ ID NOS: 31-36 or SEQ ID NOS:45-50.

E16. The method according to any one of embodiments E14 or E15, wherein the antibody is administered at a fixed dose.

E17. The method according to embodiment E16, wherein the fixed dose is between 10 and 1000 mg/dose.

E18. The method according to embodiment E16, wherein the fixed dose is about 210 mg/dose or about 700 mg/dose.

E19. The method according to any one of embodiments E1 to E18 wherein the patient has been treated before, during, after, or alternatively to the administration of an IL23 antagonist or anti-IL23 antibody or antigen-binding fragment with one or more additional therapies for the treatment of the IL23-mediated disease or disorder.

E20. The method according to any one of embodiments E1 to E19, wherein the one or more samples taken from the patient and/or the one or more control samples are one or more selected from the group consisting of: whole blood, blood serum, plasma, saliva, sputum, bronchoalveolar lavage fluid, cerebrospinal fluid, pleural fluid, pericardial fluid, ascites, synovial fluid, epithelial cells, urine, stool, skin, tissue biopsy, or a combination thereof.

E21. The method according to any one of embodiments E1 to E20, wherein the one or more control samples are (i) a sample or samples obtained from normal healthy individuals; (ii) a sample or samples obtained from patients with a non-IL23-mediated disease; or (iii) a combination thereof.

E22. The method according to any one of embodiments E1 to E21, wherein the patient's level of IL22 and/or LCN2 is measured in an immunoassay, including an immunoassay described in Example 3.

E23. The method according to any one of embodiments E1 to E22, further comprising determining the level of one or more IL23 Pathway Biomarker selected from the group consisting of IL17F, IL17A/F, IL23R, IL12B, IL6, IL21, TNF, CCR6, CCL22, IL1R1, IFNγ, S100A12, DEFB-2, DEFB-4, IL1, SERPINB3, PI3/Elafin, LL37, RORγ, RORγT, IL26, S100A7, DEFB103B, and GM-CSF.

E24. The method according to any one any one of embodiments E1 to E23, wherein the predetermined threshold level of IL22 and/or LCN2 is selected from the group consisting of: (a) about the mean level of IL22 and/or LCN2; (b) about the median level of IL22 and/or LCN2; and (c) about the $1^{st}$, $2^{nd}$, $3^{rd}$, $4^{th}$, $5^{th}$, $6^{th}$, $7^{th}$, $8^{th}$, or $9^{th}$ decile baseline level of IL22 and/or LCN2 as described in TABLES 4 or 5; and as measured in the serum using an immunoassay from a plurality of (i) normal healthy patients, (ii) patients with a non-IL23-mediated disease, and/or (iii) patients with an IL23-mediated disease.

E25. The method according to any one of embodiments E1 to E24, wherein the IL23-mediated disease or disorder is a pulmonary disease, an inflammatory bowel disease, a chronic inflammatory skin disease, an inflammatory disease, an autoimmune disease, a neurodegenerative disease, an infection, or a cancer.

E26. The method according to any one of embodiments E1 to E25, wherein the IL23-mediated disease or disorder is selected from the group consisting of: asthma, IPF, COPD. Crohn's disease, ulcerative colitis (UC), celiac disease, atopic dermatitis, allergic contact dermatitis, eczema, psoriasis, alopecia areata, palmoplantar pustulosis, psoriatic arthritis, anklyosing spondylitis, arthritis, rheumatoid arthritis (RA), a rheumatic disorder, ANCA vasculitis, Bechet's disease, autoimmune thyroiditis, type 1 diabetes, multiple sclerosis (MS), Sjogren's syndrome (SS), systemic lupus erythematosus (SLE), Alzheimer's disease, mycobacterial disease, leishmaniasis, gastric cancer, colorectal cancer, esophageal cancer, leukemia, hepatitis B virus (HBV)-related hepatocellular carcinoma, breast cancer, lung cancer, and nasopharyngeal cancer.

E27. The method according to embodiment E25, wherein the inflammatory bowel disease is Crohn's disease, UC or Celiac Disease.

E28. The method according to embodiment E27, wherein the patient is determined to have a level of CRP≥5 mg/L and/or a level of FCP≥250 μg/g, a level of FCP≥200 μg/g, a level of FCP≥150 μg/g, a level of FCP≥100 μg/g, or a level of FCP at least about 100 μg/g to at least about 250 μg/g in one or more samples taken from the patient.

E29. The method according to any one of embodiments E1 to E28, wherein (a) the predetermined IL22 threshold level is at least about 7.9 pg/mL to at least about 31.4 pg/mL as measured using an immunoassay; and/or (b) the predetermined LCN2 threshold level is at least about 143 ng/mL to at least about 261 ng/mL as measured using an immunoassay.

E30. The method according to embodiment E29, wherein (a) the predetermined IL22 threshold level is about 15.6 pg/mL as measured using an immunoassay; and/or, (b) the predetermined LCN2 threshold level is about 215 ng/mL as measured using an immunoassay.

E31. The method according to any one of embodiments E1 to E28 wherein (a) the predetermined IL22 threshold level is about 7.9 pg/mL, about 11.3 pg/mL, about 12.7 pg/mL, about 15.6 pg/mL, about 19.6 pg/mL, about 23.1 pg/mL, about 31.4 pg/mL or about 46.8 pg/mL in serum as measured using a IL22 immunoassay; and/or (b) the predetermined LCN2 threshold level is about 142.8 ng/mL, about 163.6 ng/mL, about 184.3 ng/mL, about 201.3 ng/mL, about 214.6 ng/mL, about 233.4 ng/mL, about 261.1 ng/mL, about 294.8 ng/mL, or about 326.6 ng/mL in serum as measured using a LCN2 immunoassay.

E32. The method according to any one of embodiments E27 to E31, wherein administration of the IL23 antagonist or anti-IL23 antibody or antigen-binding fragment thereof results in a Crohn's Disease Activity Index (CDAI) response score reduction of at least 100 points, or reduction of the total CDAI score to below 150 points after first administering the anti-IL23 antibody or antigen-binding fragment thereof.

E33. The method according to embodiment E32, wherein the CDAI response score reduction of at least 100 points, or reduction of the total CDAI score to below 150 points occurs within 1, 2, 4, 8, 12, 16 or 24 weeks or later after first administering the IL23 antagonist or anti-IL23 antibody or antigen-binding fragment thereof.

E34. A method of treating an interleukin-23 (IL23)-mediated disease in a patient, comprising administering an IL23 antagonist (including, e.g., an anti-IL23 antibody) to a patient if the patient is determined or identified to have an IL23 pathway with increased or higher activity in one or more samples taken from the patient compared to a predetermined IL23 pathway activity threshold level, or compared to a IL23 pathway activity level in one or more control samples.

E35. The method according to embodiment E34, further comprising determining the level of one or more IL23 Pathway Biomarkers selected from the group consisting of IL22, LCN2, CCL20, IL17F, IL17A/F, IL23R, IL12B, IL6, IL21, TNF, CCR6, CCL22, IL1R1, IFNγ, S100A12, DEFB-2, DEFB-4, IL1, SERPINB3, PI3/Elafin, LL37, RORγ, RORγT, IL26, S100A7, DEFB103B, and GM-CSF; wherein an increased or higher level of one or more of the IL23 Pathway Biomarkers in one or more samples taken from the patient compared to a predetermined IL23 Pathway Biomarker threshold level, or compared to a IL23 Pathway Biomarker level in one or more control samples indicates an IL23 pathway with increased or higher activity.

LIST OF ABBREVIATIONS

| Abbreviation or Specialized Term | Definition |
| --- | --- |
| ADA(s) | anti-drug antibody/antibodies |
| AE | adverse event |
| ANCOVA | analysis of covariance |
| AS | ankylosing spondylitis |
| CD | Crohn's disease |
| CDAI | Crohn's Disease Activity Index |
| CRP | C-reactive protein |
| DNA | deoxyribonucleic acid |
| GI | Gastrointestinal |
| IBD | inflammatory bowel disease |
| IBDQ | inflammatory bowel disease questionnaire |
| IFN | Interferon |
| IgG2 | immunoglobulin G2 |
| IL | Interleukin |
| IM | Immunogenicity |
| IV | Intravenous |
| LOCF | last observation carried forward |
| Mab | monoclonal antibody |
| MedDRA | Medical Dictionary for Regulatory Activities |
| mITT | modified intent-to-treat |
| MS | multiple sclerosis |
| NK | natural killer |
| PD | Pharmacodynamics |
| PK | pharmacokinetic(s) |
| PP | per protocol |
| PROs | Patient Reported Outcomes |
| PsO | Psoriasis |
| Q4W | every 4 weeks |

| Abbreviation or Specialized Term | Definition |
|---|---|
| RA | rheumatoid arthritis |
| RNA | ribonucleic acid |
| SAE | serious adverse event |
| SC | subcutaneous(ly) |
| Th | T helper |

| Abbreviation or Specialized Term | Definition |
|---|---|
| TNFα | tumor necrosis factor-alpha |
| UC | ulcerative colitis |
| w/v | weight per volume |

SEQUENCES

| SEQ ID NO | Description | Sequence |
|---|---|---|
| 1 | IL22 gene (mRNA) | CGACCAGGTTCTCCTTCCCCAGTCACCAGTTGCTCGAGTTAGAATTGTCT GCAATGGCCGCCCTGCAGAAATCTGTGAGCTCTTTCCTTATGGGGACCCT GGCCACCAGCTGCCTCCTTCTCTTGGCCCTCTTGGTACAGGGAGGAGCAG CTGCGCCCATCAGCTCCCACTGCAGGCTTGACAAGTCCAACTTCCAGCAG CCCTATATCACCAACCGCACCTTCATGCTGGCTAAGGAGGCTAGCTTGGC TGATAACAACACAGACGTTCGTCTCATTGGGGAGAAACTGTTCCACGGAG TCAGTATGAGTGAGCGCTGCTATCTGATGAAGCAGGTGCTGAACTTCACC CTTGAAGAAGTGCTGTTCCCTCAATCTGATAGGTTCCAGCCTTATATGCA GGAGGTGGTGCCCTTCCTGGCCAGGCTCAGCAACAGGCTAAGCACATGTC ATATTGAAGGTGATGACCTGCATATCCAGAGGAATGTGCAAAAGCTGAAG GACACAGTGAAAAAGCTTGGAGAGAGTGGAGAGATCAAAGCAATTGGAGA ACTGGATTTGCTGTTTATGTCTCTGAGAAATGCCTGCATTTGACCAGAGC AAAGCTGAAAAATGAATAACTAACCCCCTTTCCCTGCTAGAAATAACAAT TAGATGCCCCAAAGCGATTTTTTTTAACCAAAAGGAAGATGGGAAGCCAA ACTCCATCATGATGGGTGGATTCCAAATGAACCCCTGCGTTAGTTACAAA GGAAACCAATGCCACTTTTGTTTATAAGACCAGAAGGTAGACTTTCTAAG CATAGATATTTATTGATAACATTTCATTGTAACTGGTGGTTCTATACACAG AAAACAATTTATTTTTTAAATAATTGTCTTTTTCCATAAAAAAGATTACT TTCCATTCCTTTAGGGGAAAAAACCCCTAAATAGCTTCATGTTTCCATAA TCAGTACTTTATATTTATAAATGTATTTATTATTATTATAAGACTGCATT TTATTTATATCATTTTATTAATATGGATTTATTTATAGAAACATCATTCG ATATTGCTACTTGAGTGTAAGGCTAATATTGATATTTATGACAATAATTA TAGAGCTATAACATGTTTATTTGACCTCAATAAACACTTGGATATCC |
| 2 | IL22 protein | MAALQKSVSSFLMGTLATSCLLLLALLVQGGAAAPISSHCRLDKSNFQQP YITNRTFMLAKEASLADNNTDVRLIGEKLFHGVSMSERCYLMKQVLNFTL EEVLFPQSDRFQPYMQEVVPFLARLSNRLSTCHIEGDDLHIQRNVQKLKD TVKKLGESGEIKAIGELDLLFMSLRNACI |
| 3 | LCN2 gene (mRNA) | ACTCGCCACCTCCTCTTCCACCCCTGCCAGGCCCAGCAGCCACCACAGCG CCTGCTTCCTCGGCCCTGAAATCATGCCCCTAGGTCTCCTGTGGCTGGGC CTAGCCCTGTTGGGGGCTCTGCATGCCCAGGCCCAGGACTCCACCTCAGA CCTGATCCCAGCCCCACCTCTGAGCAAGGTCCCTCTGCAGCAGAACTTCC AGGACAACCAATTCCAGGGGAAGTGGTATGTGGTAGGCCTGGCAGGGAAT GCAATTCTCAGAGAAGACAAAGACCCGCAAAAGATGTATGCCACCATCTA TGAGCTGAAAGAAGACAAGAGCTACAATGTCACCTCCGTCCTGTTTAGGA AAAAGAAGTGTGACTACTGGATCAGGACTTTTGTTCCAGGTTGCCAGCCC GGCGAGTTCACGCTGGGCAACATTAAGAGTTACCCTGGATTAACGAGTTA CCTCGTCCGAGTGGTGAGCACCAACTACAACCAGCATGCTATGGTGTTCT TCAAGAAAGTTTCTCAAAACAGGGAGTACTTCAAGATCACCCTCTACGGG AGAACCAAGGAGCTGACTTCGGAACTAAAGGAGAACTTCATCCGCTTCTC CAAATCTCTGGGCCTCCCTGAAAACCACATCGTCTTCCCTGTCCCAATCG ACCAGTGTATCGACGGCTGAGTGCACAGGTGCCGCCAGCTGCCGCACCAG CCCGAACACCATTGAGGGAGCTGGGAGACCCTCCCCACAGTGCCACCCAT GCAGCTGCTCCCCAGGCCACCCCGCTGATGGAGCCCCACCTTGTCTGCTA AATAAACATGCCCTCAGGCCAAAAAAAAAAAAAAAAAA |
| 4 | LCN2 protein | MPLGLLWLGLALLGALHAQAQDSTSDLIPAPPLSKVPLQQNFQDNQFQGK WYVVGLAGNAILREDKDPQKMYATIYELKEDKSYNVTSVLFRKKKCDYWI RTFVPGCQPGEFTLGNIKSYPGLTSYLVRVVSTNYNQHAMVFFKKVSQNR EYFKITLYGRTKELTSELKENFIRFSKSLGLPENHIVFPVPIDQCIDG |
| 5 | MEDI2070 VH | QVQLVESGGGVVQPGRSLRLSCAASGFTFSSYGMHWVRQAPGKGLEWVAV IWYDGSNEYYADSVKGRFTISRDNSKNTLYLQMNSLRAEDTAVYYCARDR GYTSSWYPDAFDIWGQGTMVTVSS |
| 6 | MEDI2070 VL | QSVLTQPPSVSGAPGQRVTISCTGSSSNTGAGYDVHWYQQVPGTAPKLLI YGSGNRPSGVPDRFSGSKSGTSASLAITGLQAEDEADYYCQSYDSSLSGW VFGGGTRLTVL |
| 7 | CRP gene (mRNA) | AAGGCAAGAGATCTAGGACTTCTAGCCCCTGAACTTTCAGCCGAATACAT CTTTTCCAAAGGAGTGAATTCAGGCCCTTGTATCACTGGCAGCAGGACGT GACCATGGAGAAGCTGTTGTGTTTCTTGGTCTTGACCAGCCTCTCTCATG |

| SEQ ID NO | Description | Sequence |
|---|---|---|
| | | CTTTTGGCCAGACAGACATGTCGAGGAAGGCTTTTGTGTTTCCCAAAGAG<br>TCGGATACTTCCTATGTATCCCTCAAAGCACCGTTAACGAAGCCTCTCAA<br>AGCCTTCACTGTGTGCCTCCACTTCTACACGGAACTGTCCTCGACCCGTG<br>GGTACAGTATTTTCTCGTATGCCACCAAGAGACAAGACAATGAGATTCTC<br>ATATTTTGGTCTAAGGATATAGGATACAGTTTTACAGTGGGTGGGTCTGA<br>AATATTATTCGAGGTTCCTGAAGTCACAGTAGCTCCAGTACACATTTGTA<br>CAAGCTGGGAGTCCGCCTCAGGGATCGTGGAGTTCTGGGTAGATGGGAAG<br>CCCAGGGTGAGGAAGAGTCTGAAGAAGGGATACACTGTGGGGGCAGAAGC<br>AAGCATCATCTTGGGGCAGGAGCAGGATTCCTTCGGTGGGAACTTTGAAG<br>GAAGCCAGTCCCTGGTGGGAGACATTGGAAATGTGAACATGTGGGACTTT<br>GTGCTGTCACCAGATGAGATTAACACCATCTATCTTGGCGGGCCCTTCAG<br>TCCTAATGTCCTGAACTGGCGGGCACTGAAGTATGAAGTGCAAGGCGAAG<br>TGTTCACCAAACCCCAGCTGTGGCCCTGAGGCCCAGCTGTGGGTCCTGAA<br>GGTACCTCCCGGTTTTTTACACCGCATGGGCCCCACGTCTCTGTCTCTGG<br>TACCTCCCGCTTTTTTACACTGCATGGTTCCCACGTCTCTGTCTCTGGGC<br>CTTTGTTCCCCTATATGCATTGCAGGCCTGCTCCACCCTCCTCAGCGCCT<br>GAGAATGGAGGTAAAGTGTCTGGTCTGGGAGCTCGTTAACTATGCTGGGA<br>AACGGTCCAAAAGAATCAGAATTTGAGGTGTTTTGTTTTCATTTTTATTT<br>CAAGTTGGACAGATCTTGGAGATAATTTCTTACCTCACATAGATGAGAAA<br>ACTAACACCCAGAAAGGAGAAATGATGTTATAAAAAACTCATAAGGCAAG<br>AGCTGAGAAGGAAGCGCTGATCTTCTATTTAATTCCCCACCCATGACCCC<br>CAGAAAGCAGGAGGGCATTGCCCACATTCACAGGGCTCTTCAGTCTCAGA<br>ATCAGGACACTGGCCAGGTGTCTGGTTTGGGTCCAGAGTGCTCATCATCA<br>TGTCATAGAACTGCTGGGCCCAGGTCTCCTGAAATGGGAAGCCCAGCAAT<br>ACCACGCAGTCCCTCCACTTTCTCAAAGCACACTGGAAAGGCATTAGAA<br>TTGCCCCAGCAGAGCAGATCTGCTTTTTTTCCAGAGCAAAATGAAGCACT<br>AGGTATAAATATGTTGTTACTGCCAAGAACTTAAATGACTGGTTTTTGTT<br>TGCTTGCAGTGCTTTCTTAATTTTATGGCTCTTCTGGGAAACTCCTCCCC<br>TTTTCCACACGAACCTTGTGGGGCTGTGAATTCTTTCTTCATCCCCGCAT<br>TCCCAATATACCCAGGCCACAAGAGTGGACGTGAACCACAGGGTGTCCTG<br>TCAGAGGAGCCCATCTCCCATCTCCCCAGCTCCCTATCTGGAGGATAGTT<br>GGATAGTTACGTGTTCCTAGCAGGACCAACTACAGTCTTCCCAAGGATTG<br>AGTTATGGACTTTGGAGTGAGACATCTTCTTGCTGCTGGATTTCCAAGC<br>TGAGAGGACGTGAACCTGGGACCACCAGTAGCCATCTTGTTTGCCACATG<br>GAGAGAGACTGTGAGGACAGAAGCCAAACTGGAAGTGGAGGAGCCAAGGG<br>ATTGACAAACAACAGAGCCTTGACCACGTGGAGTCTCTGAATCAGCCTTG<br>TCTGGAACCAGATCTACACCTGGACTGCCCAGGTCTATAAGCCAATAAAG<br>CCCCTGTTTACTTGAAAAAAAAA |
| 8 | CRP protein | MEKLLCFLVLTSLSHAFGQTDMSRKAFVFPKESDTSYVSLKAPLTKPLKA<br>FTVCLHFYTELSSTRGYSIFSYATKRQDNEILIFWSKDIGYSFTVGGSEI<br>LFEVPEVTVAPVHICTSWESASGIVEFWVDGKPRVRKSLKKGYTVGAEAS<br>IILGQEQDSFGGNFEGSQSLVGDIGNVNMWDFVLSPDEINTIYLGGPFSP<br>NVLNWRALKYEVQGEVFTKPQLWP |
| 9 | Calprotectin S100A8 subunit (mRNA) | ATGTCTCTTGTCAGCTGTCTTTCAGAAGACCTGGTGGGCAAGTCCGTGG<br>GCATCATGTTGACCGAGCTGGAGAAAGCCTTGAACTCTATCATCGACGTC<br>TACCACAAGTACTCCCTGATAAAGGGGAATTTCCATGCCGTCTACAGGGA<br>TGACCTGAAGAAATTGCTAGAGACCGAGTGTCCTCAGTATATCAGGAAAA<br>AGGGTGCAGACGTCTGGTTCAAAGAGTTGGATATCAACACTGATGGTGCA<br>GTTAACTTCCAGGAGTTCCTCATTCTGGTGATAAAGATGGGCGTGGCAGC<br>CCACAAAAAAGCCATGAAGAAAGCCACAAAGAGTAGCTGAGTTACTGGG<br>CCCAGAGGCTGGGCCCCTGGACATGTACCTGCAGAATAATAAAGTCATCA<br>ATACCTCAAAAAAAAAAAAAAAAAAA |
| 10 | Calprotectin S100A8 subunit | MLTELEKALNSIIDVYHKYSLIKGNFHAVYRDDLKKLLETECPQYIRKKG<br>ADVWFKELDINTDGAVNFQEFLILVIKMGVAAHKKSHEESHKE |
| 11 | Calprotectin S100A9 subunit (mRNA) | AAACACTCTGTGTGGCTCCTCGGCTTTGACAGAGTGCAAGACGATGACTT<br>GCAAAATGTCGCAGCTGGAACGCAACATAGAGACCATCATCAACACCTTC<br>CACCAATACTCTGTGAAGCTGGGGCACCCAGACACCCTGAACCAGGGGGA<br>ATTCAAAGAGCTGGTGCGAAAAGATCTGCAAAATTTTCTCAAGAAGGAGA<br>ATAAGAATGAAAAGGTCATAGAACACATCATGGAGGACCTGGACACAAAT<br>GCAGACAAGCAGCTGAGCTTCGAGGAGTTCATCATGCTGATGGCGAGGCT<br>AACCTGGGCCTCCCACGAGAAGATGCACGAGGGTGACGAGGGCCCTGGCC<br>ACCACCATAAGCCAGGCCTCGGGGAGGGCACCCCCTAAGACCACAGTGGC<br>CAAGATCACAGTGGCCACGGCCACGGCCACAGTCATGGTGGCCACGGCCA<br>CAGCCACTAATCAGGAGGCCAGGCCACCCTGCCTCTACCCAACCAGGGCC<br>CCGGGGCCTGTTATGTCAAACTGTCTTGGCTGTGGGGCTAGGGGCTGGGG<br>CCAAATAAAGTCTCTTCCTCCAAGTCAAAAAAAAAA |
| 12 | Calprotectin S100A9 subunit | MTCKMSQLERNIETIINTFHQYSVKLGHPDTLNQGEFKELVRKDLQNFLK<br>KENKNEKVIEHIMEDLDTNADKQLSFEEFIMLMARLTWASHEKMHEGDEG<br>PGHHHKPGLGEGTP |

| SEQ ID NO | Description | Sequence |
|---|---|---|
| 13 | IL-23 alpha subunit (p19) | MLGSRAVMLLLLLPWTAQGRAVPGGSSPAWTQCQQLSQKLCTLAWSAHPLVGHMDLREEG DEETTNDVPHIQCGDGCDPQGLRDNSQFCLQRIHQGLIFYEKLLGSDIFTGEPSLLPDSP VGQLHASLLGLSQLLQPEGHHWETQQIPSLSPSQPWQRLLLRFKILRSLQAFVAVAARVF AHGAATLSP |
| 14 | IL-12 beta subunit (p40) | MCHQQLVISWFSLVFLASPLVAIWELKKDVYVVELDWYPDAPGEMVVLTCDTPEEDGITW TLDQSSEVLGSGKTLTIQVKEFGDAGQYTCHKGGEVLSHSLLLLHKKEDGIWSTDILKDQ KEPKNKTFLRCEAKNYSGRFTCWWLTTISTDLTFSVKSSRGSSDPQGVTCGAATLSAERV RGDNKEYEYSVECQEDSACPAAEESLPIEVMVDAVHKLKYENYTSSFFIRDIIKPDPPKN LQLKPLKNSRQVEVSWEYPDTWSTPHSYFSLTFCVQVQGKSKREKKDRVFTDKTSATVIC RKNASISVRAQDRYYSSSWSEWASVPCS |
| 15 | MEDI2070 HC | QVQLVESGGGVVQPGRSLRLSCAASGFTFSSYGMHWVRQAPGKGLEWVAVIWYDGSNEYYAD SVKGRFTISRDNSKNTLYLQMNSLRAEDTAVYYCARDRGYTSSWYPDAFDIWGQGTMVTVSS ASTKGPSVFPLAPCSRSTSESTAALGCLVKDYFPEPVTVSWNSGALTSGVHTFPAVLQSSGL YSLSSVVTVPSSNFGTQTYTCNVDHKPSNTKVDKTVERKCCVECPPCPAPPVAGPSVFLFPP KPKDTLMISRTPEVTCVVVDVSHEDPEVQFNWYVDGVEVHNAKTKPREEQFNSTFRVVSVLT VVHQDWLNGKEYKCKVSNKGLPAPIEKTISKTKGQPREPQVYTLPPSREEMTKNQVSLTCLV KGFYPSDIAVEWESNGQPENNYKTTPPMLDSDGSFFLYSKLTVDKSRWQQGNVFSCSVMHEA LHNHYTQKSLSLSPGK |
| 16 | MEDI2070 LC | QSVLTQPPSVSGAPGQRVTISCTGSSSNTGAGYDVHWYQQVPGTAPKLLIYGSGNRPSGVPD RFSGSKSGTSASLAITGLQAEDEADYYCQSYDSSLSGWVFGGGTRLTVLGQPKAAPSVTLFP PSSEELQANKATLVCLISDFYPGAVTVAWKADSSPVKAGVETTTPSKQSNNKYAASSYLSLT PEQWKSHRSYSCQVTHEGSTVEKTVAPTECS |
| 17 | Ustekinumab HC | EVQLVQSGAEVKKPGESLKISCKGSGYSFTTYWLGWVRQMPGKGLDWIGIMSPVDSDIRY SPSFQGQVTMSVDKSITTAYLQWNSLKASDTAMYYCARRRPGQGYFDFWGQGTLVTVSSS STKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKRVEPKSCDKTHTCPPCPAPELLGGP SVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSKLTVDKSRWQ QGNVFSCSVMHEALHNHYTQKSLSLSPGK |
| 18 | Ustekinumab LC | DIQMTQSPSSLSASVGDRVTITCRASQGISSWLAWYQQKPEKAPKSLIYAASSLQSGVPS RFSGSGSGTDFTLTISSLQPEDFATYYCQQYNIYPYTFGQGTKLEIKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 19 | Vedolizumab HC | QVQLVQSGAEVKKPGASVKVSCKGSGYTFTSYWMHWVRQAPGQRLEWIGEIDPSESNTNY NQKFKGRVTLTVDISASTAYMELSSLRSEDTAVYYCARGGYDGWDYAIDYWGQGTLVTVS SASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELAG APSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYSKLTVDKSR WQQGNVFSCSVMHEALHNHYTQKSLSLSPGK |
| 20 | Vedolizumab LC | DVVMTQSPLSLPVTPGEPASISCRSSQSLAKSYGNTYLSWYLQKPGQSPQLLIYGISNRF SGVPDRFSGSGSGTDFTLKISRVEAEDVGVYYCLQGTHQPYTFGQGTKVEIKRTVAAPSV FIFPPSDEQLKSGTASVVCLLNNFYPREAKVQWKVDNALQSGNSQESVTEQDSKDSTYSL SSTLTLSKADYEKHKVYACEVTHQGLSSPVTKSFNRGEC |
| 21 | Adalimumab HC | EVQLVESGGGLVQPGRSLRLSCAASGFTFDDYAMHWVRQAPGKGLEWVSAITWNSGHIDY ADSVEGRFTISRDNAKNSLYLQMNSLRAEDTAVYYCAKVSYLSTASSLDYWGQGTLVTVS SASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELLG GPSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYSKLTVDKSR WQQGNVFSCSVMHEALHNHYTQKSLSLSPGK |
| 22 | Adalimumab LC | DIQMTQSPSSLSASVGDRVTITCRASQGIRNYLAWYQQKPGKAPKLLIYAASTLQSGVPS RFSGSGSGTDFTLTISSLQPEDVATYYCQRYNRAPYTFGQGTKVEIKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 23 | Certolizumab HC | EVQLVESGGGLVQPGGSLRLSCAASGYVFTDYGMNWVRQAPGKGLEWMGWINTYIGEPIY ADSVKGRFTFSLDTSKSTAYLQMNSLRAEDTAVYYCARGYRSYAMDYWGQGTLVTVSSAS TKGPSVFPLAPSSKSTSGGTAALGCLVKDYFPEPVTVSWNSGALTSGVHTFPAVLQSSGL YSLSSVVTVPSSSLGTQTYICNVNHKPSNTKVDKKVEPKSCDKTHTCAA |

| SEQ ID NO | Description | Sequence |
|---|---|---|
| 24 | Certolizumab LC | DIQMTQSPSSLSASVGDRVTITCKASQNVGTNVAWYQQKPGKAPKALIYSASFLYSGVPY RFSGSGSGTDFTLTISSLQPEDFATYYCQQYNIYPLTFGQGTKVEIKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 25 | Briakinumab HC | QVQLVESGGGVVQPGRSLRLSCAASGFTFSSYGMHWVRQAPGKGLEWVAFIRYDGSNKYY ADSVKGRFTISRDNSKNTLYLQMNSLRAEDTAVYYCKTHGSHDNWGQGTMVTVSSASTKG PSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPSVFL FPPKPKDTLMISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPPSREEMTKNQ VSLTCLVKGFYPSDIAVEWESNGQPENNYKTTPPVLDSDGSFFLYSKLTVDKSRWQQGNV FSCSVMHEALHNHYTQKSLSLSPGK |
| 26 | Briakinumab LC | QSVLTQPPSVSGAPGQRVTISCSGSRSNIGSNTVKWYQQLPGTAPKLLIYYNDQRPSGVP DRFSGSKSGTSASLAITGLQAEDEADYYCQSYDRYTHPALLEGTGTKVTVLGQPKAAPSV TLFPPSSEELQANKATLVCLISDFYPGAVTVAWKADSSPVKAGVETTTPSKQSNNKYAAS SYLSLTPEQWKSHRSYSCQVTHEGSTVEKTVAPTECS |
| 27 | Tildrakizumab HC | QVQLVQSGAEVKKPGASVKVSCKASGYIFITYWMTWVRQAPGQGLEWMGQIFPASGSADY NEKFEGRVTMTTDTSTSTAYMELRSLRSDDTAVYYCARGGGGFAYWGQGTLVTVSSASTK GPSVFPLAPSSKSTSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFELYSKLTVDKSRWQQGN VFSCSVMHEALHNHYTQKSLSLSPGK |
| 28 | Tildrakizumab LC | DIQMTQSPSSLSASVGDRVTITCRTSENIYSYLAWYQQKPGKAPKLLIYNAKTLAEGVPS RFSGSGSGTDFTLTISSLQPEDFATYYCQHHYGIPFTFGQGTKVEIKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 29 | Etrolizumab HC | EVQLVESGGGLVQPGGSLRLSCAASGFFITNNYWGWVRQAPGKGLEWVGYISYSGSTSYN PSLKSRFTISRDTSKNTFYLQMNSLRAEDTAVYYCARTGSSGYFDFWGQGTLVTVSSAST KGPSVFPLAPSSKSTSGGTAALGCLVKDYFPEPVTVSWNSGALTSGVHTFPAVLQSSGLY SLSSVVTVPSSSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSREEMTK NQVSLTCLVKGFYPSDIAVEWESNGQPENNYKTTPPVLDSDGSFFLYSKLTVDKSRWQQG NVFSCSVMHEALHNHYTQKSLSLSPG |
| 30 | Etrolizumab LC | DIQMTQSPSSLSASVGDRVTITCRASESVDDLLHWYQQKPGKAPKLLIKYASQSISGVPS RFSGSGSGTDFTLTISSLQPEDFATYYCQQGNSLPNTFGQGTKVEIKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 31 | MEDI2070 VH-CDR1 | SYGMH |
| 32 | MEDI2070 VH-CDR2 | VIWYDGSNEYYADSVKG |
| 33 | MEDI207- VH-CDR3 | DRGYTSSWYPDAFDI |
| 34 | MEDI2070 VL-CDR1 | TGSSSNTGAGYDVH |
| 35 | MEDI2070 VL-CDR2 | GSGNRPS |
| 36 | MEDI2070 VL-CDR3 | QSYDSSLSGWV |
| 37 | LCN2 variant | DQCIDG |
| 38 | LCN2 variant | GNGQSG |
| 39 | CRP variant | YSIFSYATKRQDNEIL |
| 40 | CRP variant | TVFSRMPPRDKTMRFF |

| SEQ ID NO | Description | Sequence |
|---|---|---|
| 41 | S100A8 variant | VAAHKKSHEESHKE |
| 42 | S100A8 variant | WQPTKKAMKKATKSS |
| 43 | Antibody B VH | QVQLQESGPGLVKPSQTLSLTCTVSGGSISSGGYYWSWIRQHPGKGLEWIGHIHYSGNTYYN PSLKSRVTISVDTSKNQFSLKLSSVTAADTAVYYCAKNRGFYYGMDVWGQGTTVTVSS |
| 44 | Antibody B VL | DIQMTQSPSSVSASVGDRVTITCRASQVISSWLAWYQQKPGKAPSLLIYAASSLQSGVPSRF SGSVSGTDFTLTISSLQPEDFATYYCQQANSFPFTFGPGTKVDFK |
| 45 | Antibody B VH-CDR1 | SGGYYWS |
| 46 | Antibody B VH-CDR2 | HIHYSGNTYYNPSLKS |
| 47 | Antibody B VH-CDR3 | NRGFYYGMDV |
| 48 | Antibody B VL-CDR1 | RASQVISSWLA |
| 49 | Antibody B VL-CDR2 | AASSLQS |
| 50 | Antibody B VL-CDR3 | QQANSFPFT |

All patents and publications referred to herein are expressly incorporated by reference in their entireties.

Aspects of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

It is to be appreciated that the Detailed Description section, and not the Summary and Abstract sections, is intended to be used to interpret the claims. The Summary and Abstract sections may set forth one or more but not all exemplary aspects of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

EXAMPLES

The invention will be more fully understood by reference to the following examples which detail exemplary aspects of the invention.

Example 1

Phase 2a Clinical Study Protocol

A Phase 2a study was conducted to evaluate the efficacy and safety of multiple IV doses of MEDI2070 (700 mg) or placebo administered on Week 0 (Day 1) and Week 4 (Day 29) during an initial 12-week treatment period in subjects with moderate to severe CD who have failed or are intolerant to anti-TNFα therapy. The following clinical trial protocol was carried out in human patients. Results of the clinical trial are presented in Example 2.

I. Clinical Study Summary

The Phase 2a study evaluated the efficacy and safety of multiple IV doses of MEDI2070 (700 mg) or placebo administered on Week 0 (Day 1) and Week 4 (Day 29) during an initial 12-week treatment period in subjects with moderate to severe CD who failed or are intolerant to anti-TNFα therapy. A 100-week, open-label, treatment period was included to allow evaluation of the long-term safety of MEDI2070 (administered at 210 mg SC Q4W) and to provide information on PK and efficacy data.

The primary objective of this study was to evaluate the efficacy of MEDI2070 versus placebo to induce a clinical effect (defined as at least a 100-point reduction in CDAI from baseline) or remission (defined as CDAI<150)) at Week 8 in subjects with moderate to severe CD.

Secondary objectives of this study included evaluating: the efficacy of MEDI2070 versus placebo in achieving CDAI remission at Week 8; the effect of MEDI2070 versus placebo in achieving at least a CDAI 100-point reduction from baseline at Week 8; the effect of MEDI2070 versus placebo in achieving at least a CDAI 70-point reduction from baseline at Week 8; the effect of MEDI2070 versus placebo in achieving CDAI remission or at least a CDAI 100-point reduction from baseline at Week 12; the effect of MEDI2070 versus placebo on the change from baseline in CDAI at Week 8; the safety and tolerability of MEDI2070; and the PK and immunogenicity (IM) of MEDI2070.

Exploratory objectives of this study included evaluating: the effect of MEDI2070 on other measures of clinical effect including but not limited to CDAI response, change from baseline in CDAI at other timepoints, and sustained CDAI response; the effect of treatment on inflammatory markers in blood and stool; the predictive value of blood or fecal biomarkers with respect to subject response to MEDI2070; and the effect of MEDI2070 on Patient Reported Outcomes (PROs).

II. Study Design Overview

This was a two-part Phase 2a study comprising a 12-week, double-blind, placebo-controlled, treatment period followed by a 100-week, open-label, treatment period to evaluate the short-term efficacy, and the short- and long-term safety of MEDI2070 in subjects with moderate to severe, active CD who failed or are intolerant to anti-TNFα therapy as determined by the investigator. Subjects were stratified based on the number of prior anti-TNFα agents that they have failed (1 vs >1). Subjects at various centers worldwide were randomized in a 1:1 ratio to initially receive a fixed IV dose of MEDI2070 (700 mg) or placebo on Week 0 (Day 1) and Week 4 (Day 29) during the 12-week, double-blind, placebo-controlled, treatment period. At the completion of the double-blind, placebo-controlled, treatment period (Week 12), subjects had the option to enter a 100-week, open-label, treatment period where they received open-label MEDI2070 (210 mg SC) Q4W (Week 12 through Week 112) as described in FIG. 1.

MEDI2070 or placebo was administered as an IV infusion over a period of at least 60 minutes via an infusion pump on Week 0 (Day 1) and Week 4 (Day 29). Subjects who completed the 12-week, double-blind, placebo-controlled, treatment period and entered the 100-week, open-label, treatment period received MEDI2070 at a fixed dose of 210 mg SC injection Q4W for 26 doses (through Week 112). The primary analysis of the study was conducted after the last subject in the study completed the 12-week, double-blind, placebo-controlled, treatment period or was withdrawn from the study prior to completing the 12-week, double-blind, placebo-controlled, treatment period.

The doses of MEDI2070 in this study were 700 mg IV Q4W in the 12-week, double-blind, placebo-controlled, treatment period (Weeks 0 and 4) and 210 mg SC Q4W in the 100-week, open-label, treatment period (Week 12 to Week 112).

Pharmacokinetic/PD modeling of MEDI2070 predicted a greater than 99% mean suppression of plasma IL23 throughout the duration of the study for both the 700 mg IV and 210 mg SC dosing regimens. Furthermore, (potency-corrected) serum concentrations of MEDI2070 at these dosing regimens were predicted to be higher than those of the anti-IL12/23p40 antibody ustekinumab shown to be efficacious in CD (Sandborn et al. Gastroenterol. 135:1130-41 (2008)). Administration of 700 mg IV was predicted to rapidly achieve steady-state target suppression.

Previous clinical data (Sandborn et al. Gastroenterol. 135:1130-41 (2008)) indicate that changes from placebo in the response parameters after administration of IV ustekinumab maximized between 6-8 weeks after start of ustekinumab administration; therefore, the proposed placebo-controlled, double-blind period of 12 weeks is sufficient to characterize the effect of MEDI2070 in this patient population. Regulatory guidance recommends assessing the primary endpoint for induction of effect between 4-8 weeks (or after 2 cycles of dosing), thus the assessment of the primary endpoint at Week 8 is appropriate. In addition, Week 12 was assessed to observe the potential extended time course of effect for MEDI2070.

All subjects received investigational product (700 mg MEDI2070 or placebo) by IV infusion over a minimum period of 60 minutes during the 12-week, double-blind, placebo-controlled, treatment period. MEDI2070 (700 mg) or placebo was delivered in 5.0% w/v dextrose in a volume of 100 mL over a minimum of 60 minutes using an infusion pump. Before and after each IV infusion, the IV access was flushed with 5% w/v dextrose.

MEDI2070 was administered by subcutaneous (SC) injection during the 100-week, open-label, treatment period. Each SC dose was administered to the subject's anterior abdominal wall by an experienced and qualified staff member. Each SC injection was no more than 1.0 mL in volume (i.e., 3×1.0 mL injections for the 210 mg SC dose). As the MEDI2070 dosage volume exceeds 1.0 mL, the dose was equally divided in 3 syringes and administered as multiple SC injections on alternating (left or right) sites on the subject's anterior abdominal wall with no more than approximately 30 seconds of time between each injection and at a distance of at least 2 cm apart.

III. Disease Evaluation and Methods

CDAI: The CDAI is the oldest and most widely used of several multi-item instruments that have been developed and is validated for use in clinical studies to measure disease activity in CD (Best et al. Gastroenterology 70:439-44 (1976); Sands et al. N Engl J Med. 350(9):876-85 (2004)). The CDAI measures the severity of active disease using symptom scores that are monitored over the previous week and includes patient-reported symptoms, physician-assessed signs, and laboratory markers. The CDAI score is calculated by summing weighted scores for subjective items (number of liquid or very soft stools, abdominal pain and general well-being) recorded by a diary during a 1-week period, and objective items (associated symptoms, taking antidiarrheal such as loperamide/opiates, abdominal mass, hematocrit, daily morning temperature, and body weight). The CDAI scores range from 0 to 600, with higher scores indicating greater disease activity. Subjects with scores of <150, 150 to 219, and 220 to 450 represent remission, mild disease, and moderate to severe disease, respectively; whereas subjects with scores of >450 have very severe disease (Buxton et al. Value Health. 10:214-20 (2007)). The CDAI was calculated at the site in order to determine the eligibility for the study. For statistical analysis, CDAI for all visits was also calculated.

Patient Reported Outcomes: The study assessed patient reported outcomes (PROs) using the IBDQ. The IBDQ was completed by subjects using a paper questionnaire at study visits, scheduled at Weeks 0, 4, 8, and 12 and was administered before any other assessments.

Inflammatory Bowel Disease Questionnaire (IBDQ): The IBDQ is a validated, disease-specific PRO instrument that measures health-related quality of life in patients with IBD (Guyatt et al. Gastroenterology. 96:804-10 (1989)). The IBDQ covers the following dimensions: bowel symptoms (10 items), systemic symptoms (5 items), emotional function (12 items), and social function (5 items). Items are scored on a 7-point Likert scale, yielding a global score in the range 32 to 224 (with higher scores indicating better quality of life). The IBDQ has been frequently used in drug approval applications to assess treatment efficacy in IBD. The IBDQ was designed to be self-administered and completed in 5 minutes.

IV. Endpoints

The primary endpoint of the study was CDAI response at Week 8, defined by either a CDAI score of <150 or a CDAI reduction from baseline of at least 100 points. Baseline was defined as the latest nonmissing observation prior to first administration of the investigational product.

Missing data was imputed by nonresponder imputation approach; i.e., any subject with missing information on primary endpoint was assumed as nonresponder. In addition, subjects with a clinically meaningful increase in steroid use were assumed to be a nonresponder for the primary analysis perspective.

For the primary endpoint, comparisons between treatment arms were based on the mITT population and were performed using a logistic regression model with treatment and stratification factor as covariate. The stratification factor for this study was defined by the number of prior anti-TNFα agents a subject had received (1 vs >1). The significance of treatment effect was tested using the two-sided test at α=10%.

The following sensitivity analyses were performed: (1) A sensitivity analysis was performed by adjusting for baseline CDAI score and/or other baseline covariates by extending the model planned above for subjects in mITT population. (2) A mixed effect longitudinal logistic regression model was implemented on the observed responses. This logistic random-effect model includes a random intercept to account for the variability between subjects. Fixed categorical effects include stratification factor, treatment, visit, and treatment-by-visit interaction, as well as the continuous fixed covariates of baseline score. (3) A sensitivity analysis was performed by adjusting for baseline CDAI score and/or other baseline covariates by extending the model planned above for subjects in the PP Population.

Secondary Endpoints included:
1) CDAI remission at Week 8, as defined by a CDAI score of <150;
2) A reduction of at least 100 points from baseline in CDAI at Week 8;
3) A reduction of at least 70 points from baseline in CDAI at Week 8;
4) CDAI response (either remission defined by CDAI<150 or a CDAI reduction from baseline of at least 100 points from baseline) at Week 12. Secondary endpoints 1, 2, 3, and 4 were analyzed in a similar way to the primary endpoint. In addition, a sensitivity analysis was performed by carrying forward the last response on or before the Week 8 visit to Week 12 for subjects who had increased steroid (defined as 5 mg/day prednisolone, or equivalent, or 3 mg/day budesonide).
5) Change from baseline CDAI at Week 8. Secondary endpoint 5 was analyzed by using the inverse probability weighting generalized estimating equations method adjusting for prior anti-TNFα use. Also a sensitivity analysis was performed using an ANCOVA model after missing data was imputed using the LOCF approach through the end of the double-blind, placebo-controlled, treatment period adjusting for prior anti-TNFα use.
6) To evaluate the safety and tolerability of MEDI2070, the safety and tolerability endpoints included AEs including SAEs, significant changes in laboratory values and vital signs. All safety-related endpoints for the 12-week, double-blind, placebo-controlled, treatment period were reported based on safety population using the actual treatment received. Subjects randomized to placebo with at least one dose of MEDI2070 were included in the active arm; also the subjects randomized to the MEDI2070 arm without any active dose were included in the placebo arm. The Medical Dictionary for Regulatory Activities (MedDRA) was used to code all AEs. Treatment-emergent AEs were defined as any AE with onset on or after the administration of the first dose of investigational product up to and including 36 weeks post-last dose.
7) To evaluate the PK and immunogenicity (IM) of Multiple Doses of MEDI2070, descriptive statistics of serum MEDI2070 concentration data were provided by visit. Individual and mean serum concentration-time profiles of MEDI2070 were generated For PK data analysis, time zero was defined as the beginning of infusion. The presence of anti-drug antibodies (ADAs) to MEDI2070 in serum was also assessed.

Example 2

Phase 2a Clinical Study Results

I. Study Design and Patients

The phase 2a study (clinicaltrials.gov identifier: NCT01714726) described in Example 1 included a 12-week, double-blind, placebo-controlled treatment period followed by a 100-week open-label treatment period to evaluate short-term efficacy and short- and long-term safety of MEDI2070 in patients with active moderate to severe Crohn's disease who failed prior anti-TNF-α therapy. Conducted at 60 centers worldwide, the study included adults aged 18 to 65 years diagnose with ileal, ileo-colonic, or colonic Crohn's disease for at least 6 months.

Patients had to have moderate to severe active Crohn's disease (defined as a Crohn's Disease Activity Index [CDAI] score of 220-450), with evidence of active inflammation (baseline C-reactive protein [CRP]≥5 mg/L, fecal calprotectin [FCP]≥250 μg/g, or endoscopic evidence of inflammation [photographic documentation of at least 3 nonanastomotic ulcerations, each >0.5 cm in diameter, or 10 aphthous ulcerations involving at least 10 cm of contiguous intestine] within 12 weeks before screening). Patients must have received at least one anti-TNF-α therapy at approved doses for Crohn's disease, with primary nonresponse (signs and symptoms of active disease, despite at least 1 induction regimen, including at least 2 doses of anti-TNF-α therapy at least 2 weeks apart) or secondary nonresponse (recurrence of symptoms of persistently active disease during maintenance anti-TNF-α therapy following initial clinical benefit) or intolerance (including but not limited to infusion-related reaction, demyelination, congestive heart failure, or infection). Exclusion criteria included having an allogeneic bone marrow transplant or cell-based transplantation; short-bowel syndrome; obstructive stricture within 3 months of study; bowel surgery within 12 weeks of study; ileostomy or colostomy; a clinically significant concomitant disease; or prior treatment with a biologic agent targeting IL12 or IL23.

Washout of other prior therapies was required, including infliximab for 8 weeks before study, adalimumab or certolizumab for 10 weeks, natalizumab for 12 weeks; cyclosporine, mycophenolate mofetil, sirolimus, thalidomide, or tacrolimus for 4 weeks; intravenous or intramuscular corticosteroids for 2 weeks; or topical mesalamine or rectal corticosteroids for 2 weeks. Concomitant use of 5-aminosalicylates and glucocorticosteroids was permitted if doses were stable for at least 2 weeks before randomization and remained stable through week 8. Similarly, concomitant use of immunomodulators, e.g., azathioprine, was permitted if the dose remained stable from 8 weeks before randomization through week 8. Use of oral antibiotics for Crohn's disease, probiotics, and antidiarrheals was allowed.

All patients provided written informed consent. The study was conducted in accordance with the Declaration of Helsinki and Good Clinical Practice guidelines and each site's local institutional review board approved the protocol.

II. Treatment

For the double-blind period, an interactive voice or web-based response system was used for randomization to treatment arms, assigning unique randomization codes to each patient. Randomization was stratified based on the number of prior failed anti-TNF-α agents (1 vs >1). Using blinded randomization with concealed allocation based on a permutation block algorithm, patients were randomized 1:1 within each stratum to receive MEDI2070 700 mg or placebo intravenously over 60 minutes at week 0 (day 1) and week 4 (day 29). Patients, investigators, and the sponsor were blinded to treatment until the last patient reached week 12, when the primary analysis was conducted. During the open-label period (weeks 12 through 112), all patients received MEDI2070 210 mg subcutaneously every 4 weeks (26 doses over 100 weeks).

III. Study Assessments

The primary outcome measure was the proportion of patients achieving clinical effect, defined as at least a 100-point CDAI score reduction from baseline or CDAI score less than 150 at week 8. Secondary measures included the proportion of patients achieving CDAI remission (defined as CDAI score <150) at week 8, at least a 100-point CDAI score reduction (CR100) from baseline at week 8, at least a 70-point CDAI score reduction (CR70) from baseline at week 8, clinical effect at week 12, CDAI remission at week 12, and the safety and tolerability of MEDI2070, including adverse events, serious adverse events, and significant changes in laboratory values and vital signs. Serum MEDI2070 concentrations and the presence of ADAs were evaluated at baseline, week 8, week 24, and end of study.

Exploratory outcome measures included inflammatory markers in the blood and stool (CRP and FCP), responses of other biomarkers and their predictive value for clinical effects, sustained clinical effect between weeks 8 and 24, and sustained CDAI remission assessed at weeks 8 and 24. Biomarker assessments included changes in IL22 serum levels (expressed in high levels in Crohn's disease patients and a marker of disease activity [Schmechel et al., *Inflamm Bowel Dis,* 14:204-212 (2008)]) from baseline after treatment with MEDI2070 versus placebo at weeks 8 and 12; association of change from baseline in IL22 levels with clinical effect and CDAI remission after treatment with MEDI2070 versus placebo at weeks 8 and 12; and assessment of higher IL22 serum levels at baseline as a predictor of clinical effect and CDAI remission after treatment with MEDI2070 compared with placebo at weeks 8 and 12.

IV. Statistical Analysis

Assuming a CDAI clinical effect rate of 20% in the placebo group, approximately 54 patients per treatment arm were required to provide 87% power to detect a 25% difference in CDAI clinical effect rates at week 8 between MEDI2070 700 mg and placebo, using a two-sided test at significance level of α=0.1. Assuming an approximately 10% dropout rate per treatment arm adjustment, approximately 60 patients were to be randomized.

The modified intent-to-treat population included all randomized patients who received at least one dose of study treatment during the double-blind period. The safety population comprised patients who received any study treatment during the double-blind period. The per-protocol population included patients who received all treatment doses and had no major protocol deviations. The open-label population included all patients who received at least 1 dose of MEDI2070 during the open-label period.

For the primary and secondary measures with binary outcomes, comparison between treatment arms was based on the modified intent-to-treat population, using a logistic regression model [Ge et al., *Drug Inf J,* 45:481-493 (2011)], with treatment and stratification factor (number of prior anti-TNF-α agents of 1 vs >1) as covariates. The significance of the treatment effect was tested using the 2-sided test at α=10%. A sensitivity analysis was conducted by extending the planned logistic regression model to adjust for baseline CDAI score and/or other baseline covariates. Missing data for dichotomous end points were imputed using non-responder imputation. A patient imputed as a nonresponder before week 8 was considered a nonresponder for all subsequent visits. Additionally, patients with a clinically meaningful increase in steroid use were assumed to be nonresponders. Clinically meaningful increase in steroid dose was defined as an increase of at least 5 mg/day for at least 3 days of prednisone or equivalent, or an increase of at least 3 mg/day for at least 3 days of budesonide. Missing data for continuous measures were handled using the inverse probability weighting generalized estimating equations method, adjusting for prior anti-TNF-α agent use.

Pharmacokinetic data were summarized. Exploratory analyses were performed for patients in the open-label period. Efficacy data from the double-blind and open-label periods up to week 24 for these patients were combined and reported by treatment arms in the double-blind period. Change from baseline in CRP and FCP were analyzed using a mixed-effects repeated measures model, adjusting for prior anti-TNF-α use and baseline, for the open-label population. Comparisons between MEDI2070 210 mg at week 24 and MEDI2070 700 mg or placebo at week 12 were performed.

V. Patient Results

In total, 121 patients were randomized; 119 of these received double-blind treatment (FIG. 1). In the double-blind period, 52 of 59 (86.7%) and 52 of 60 (85.2%) patients completed week 12 in the MEDI2070 and placebo groups, respectively. Baseline patient characteristics generally were balanced between treatment groups (TABLE 1), except CDAI and CRP levels were numerically higher in the MEDI2070 group. Results from weeks 8, 12, and 24 are reported here; the study is ongoing for long-term follow-up.

TABLE 1

Baseline Characteristics and Demographics (modified intent-to-treat population).

| Parameter | MEDI2070 (N = 59) | Placebo (N = 60) | Total (N = 119) |
| --- | --- | --- | --- |
| Mean age, yr (SD) | 34.9 (11.2) | 38.1 (10.7) | 36.5 (11.0) |
| Female, no. (%) | 37 (62.7) | 37 (61.7) | 74 (62.2) |
| Mean weight, kg (SD) | 70.4 (20.7) | 71.9 (15.4) | 71.2 (18.2) |
| Mean disease duration, yr (SD) | 13.2 (9.4) | 11.2 (8.5) | 12.2 (9.0) |
| ≥2 yr, % | 96.6 | 90.0 | 93.3 |

TABLE 1-continued

Baseline Characteristics and Demographics (modified intent-to-treat population).

| Parameter | MEDI2070 (N = 59) | Placebo (N = 60) | Total (N = 119) |
|---|---|---|---|
| Sites of disease, no. (%) | | | |
| Ileal only | 14 (23.7) | 18 (30.0) | 32 (26.9) |
| Colonic only | 16 (27.1) | 18 (30.0) | 34 (28.6) |
| Ileo-colonic | 28 (47.5) | 24 (40.0) | 52 (43.7) |
| Other | 1 (1.7) | 0 | 1 (0.8) |
| Crohn's Disease Activity Index score | | | |
| Mean (SD) | 325.0 (59.2) | 312.4 (56.3) | 318.6 (57.8) |
| Minimum, maximum | 222, 440 | 221, 450 | 221, 450 |
| Mean C-reactive protein, mg/L (SD) | 29.8 (35.4) | 21.1 (24.2) | 25.4 (30.4) |
| Mean C-reactive protein ≥5 mg/L, no. (%) | 46 (78.0) | 39 (65.0) | 85 (71.4) |
| Mean fecal calprotectin, μg/g (SD)* | 536.7 (303.2) | 616.9 (420.7) | 578.2 (369.3) |
| Mean fecal calprotectin ≥250 μg/g, no. (%) | 41 (73.2) | 47 (78.3) | 88 (75.9) |
| Prior anti-tumor necrosis factor-α agents, no. (%) | | | |
| 1 | 18 (30.5) | 19 (31.7) | 37 (31.1) |
| 2 | 35 (59.3) | 35 (58.3) | 70 (58.8) |
| ≥3 | 6 (10.2) | 6 (10.0) | 12 (10.1) |
| Prior use of anti-tumor necrosis factor-α agents, no. (%) | | | |
| Infliximab | 51 (86.4) | 50 (83.3) | 101 (84.9) |
| Adalimumab | 45 (76.3) | 45 (75.0) | 90 (75.6) |
| Certolizumab | 10 (16.9) | 11 (18.3) | 21 (17.6) |
| Reason for discontinuing prior anti-tumor necrosis factor-α agent, no. (%) | | | |
| Primary failure | 23 (39.0) | 23 (38.3) | 46 (38.7) |
| Secondary failure | 34 (57.6) | 33 (55.0) | 67 (56.3) |
| Intolerance | 27 (45.8) | 26 (43.3) | 53 (44.5) |
| Other | 7 (11.9) | 11 (18.3) | 18 (15.1) |
| Not applicable | 0 | 2 (3.3) | 2 (1.7) |
| 5-aminosalicylate use at baseline, no. (%) | 18 (30.5) | 18 (30.0) | 36 (30.3) |
| Corticosteroid use at baseline, no. (%) | 24 (40.7) | 24 (40.0) | 48 (40.3) |
| Immunomodulators use at baseline, no. (%) | 18 (30.5) | 14 (23.3) | 32 (26.9) |
| Prior surgery for Crohn's disease, no. (%) | 29 (49.2) | 26 (43.3) | 55 (46.2) |

*Three patients had missing fecal calprotectin assessments.

VI. Efficacy
(i) Week 8

For the primary outcome measure, the rate of clinical effect at week 8 was significantly higher in the MEDI2070 group versus the placebo group (49.2% vs. 26.7%, respectively; P=0.01; point estimate: 0.225 [90% confidence interval (CI): 0.083 to 0.368]; FIG. 2A). CDAI remission rates were 27.1% with MEDI2070 and 15.0% with placebo (P=0.10; point estimate: 0.122 [90% CI: 0.000 to 0.243]). CR70 rates were 52.5% and 46.7% in the MEDI2070 and placebo groups, respectively (P=0.52), and CR100 rates were 45.8% and 25.0% in the MEDI2070 and placebo groups, respectively (P=0.02).

A significantly greater proportion of patients receiving MEDI2070 achieved the composite end points of CDAI effect and 50% reduction in FCP or CRP versus baseline (P<0.001), and CDAI remission and 50% reduction in FCP or CRP versus baseline (P=0.02; FIG. 2B). MEDI2070 treatment also resulted in significantly greater reductions in FCP versus placebo (least squares mean change −153.5 vs. −49.7; least squares mean difference −105.6 [90% CI: −184.0 to −27.2]; P=0.027) and significantly reduced CRP levels (least squares mean change: −12.6 vs. 5.1 with placebo; least squares mean difference −17.6 [90% CI: −28.3 to −6.9]; P=0.007).

(ii) Week 12

At week 12, the rate of clinical effect was greater with MEDI2070 (37.3% vs 28.3%; P=0.29), as was the rate of CDAI remission (20.3% vs. 13.3%; P=0.31); however, the differences were not statistically significant. Rates of CR100 at week 12 were 37.3% with MEDI2070 and 28.3% with placebo (P=0.288). At week 12, significant reductions in FCP and CRP with MEDI2070 were maintained (FCP: least squares mean change −179.6 vs −55.1; least squares mean difference −124.6 [90% CI: −221.2 to −27.9]; P=0.034; CRP: least squares mean change: −13.4 vs −2.6 with placebo; least squares mean difference −10.8 [90% CI: −17.6 to −4.1]; P=0.008).

(iii) Week 24

Clinical effect and CDAI remission rates were maintained in the MEDI2070 group at 24 weeks. The proportion of patients receiving placebo then open-label MEDI2070 (placebo/MEDI2070 group) who achieved clinical effect and CDAI remission was similar to those receiving MEDI2070 700 mg then open-label MEDI2070 (MEDI2070/MEDI2070) at week 24 (FIGS. 3A and 3B). Over the 24-week period, the MEDI2070/MEDI2070 group continued to achieve the composite end points of CDAI effect plus 50% reduction in FCP or CRP versus baseline, and CDAI remission plus 50% reduction in FCP or CRP versus baseline (TABLE 2). The proportion of patients in the placebo/MEDI2070 group achieving both composite end points at week 24 was similar to those in the MEDI2070/MEDI2070 group. In the MEDI2070/MEDI2070 group, changes from baseline in FCP and CRP levels were maintained between weeks 12 and 24; in the placebo/MEDI2070 group, decreases in FCP and CRP levels were observed between weeks 12 and 24.

between the MEDI2070 and placebo groups (67.8% vs. 68.3%, respectively), as were the proportion of patients with grade 3 or greater adverse events (10.2% vs. 11.7%, respec-

TABLE 2

Composite End Points (weeks 8 through 24), Sustained Effect and Remission (open-label population), and Change from Baseline in Fecal Calprotectin and C-reactive Protein (mixed-effects model; open-label population).

| Parameter, no. (%) | MEDI2070 700 mg/<br>MEDI2070 210 mg<br>(N = 52) | Placebo/<br>MEDI2070 210 mg<br>(N = 52) |
|---|---|---|
| Crohn's Disease Activity index effect and ≥50% reduction in fecal calprotectin or C-reactive protein vs baseline (nonresponder imputation) | | |
| Week 8 | 24 (46.2) | 6 (11.5) |
| Week 12 | 22 (42.3) | 5 (9.6) |
| Week 24 | 24 (46.2) | 25 (48.1) |
| Crohn's Disease Activity index remission and ≥50% reduction in fecal calprotectin or C-reactive protein vs. baseline (nonresponder imputation) | | |
| Week 8 | 14 (26.9) | 5 (9.6) |
| Week 12 | 12 (23.1) | 4 (7.7) |
| Week 24 | 19 (36.5) | 18 (34.6) |
| Sustained effect at weeks 8 and 24* (nonresponder imputation) | 22 (42.3) | 12 (23.1) |
| Sustained remission at weeks 8 and 24† (nonresponder imputation) | 12 (23.1) | 6 (11.5) |
| Mean change in fecal calprotectin, (μg/g)‡ | | |
| Double-blind period (Week 12) | −186.5 (n = 40) | −46.0 (n = 41) |
| Open-label period (Week 24) | −252.3 (n = 36) | −253.8 (n = 39) |
| Difference at week 12 vs week 24 (90% CI) | −65.7 (−161.0 to 29.5) | −207.8 (−307.0 to −108.5) |
| P value | 0.254 | <0.001 |
| Mean change in C reactive protein (mg/L)‡ | | |
| Double-blind period (Week 12) | −16.4 (n = 51) | 0.1 (n = 52) |
| Open-label period (Week 24) | −18.2 (n = 45) | −10.6 (n = 49) |
| Difference at Week 12 vs Week 24 (90% CI) | −1.8 (−7.2 to 3.6) | −10.8 (−16.4 to −5.1) |
| P value | 0.580 | 0.002 |

*Sustained effect is defined as achieving the criteria of effect at both week 8 and week 24. Percentage calculated using number of patients in the open-label population.
†Sustained remission is defined as achieving the criteria of remission at both week 8 and week 24. Percentage calculated using the number of patients in the open-label population.
‡Mean and P value were obtained from a mixed-effects model with fixed terms for treatment group, visit, treatment by visit interaction, stratification factor of prior anti-tumor necrosis factor-α use, and baseline fecal calprotectin or C-reactive protein, and patients within treatment as random effect, assuming unstructured covariance structure.

VII. MEDI2070 Exposure-Response Relationship

At the 700-mg intravenous dose of MEDI2070, no definitive relationship between exposure and efficacy was established (data not shown). Serum MEDI2070 concentrations at the week 4 trough and at weeks 8 and 12 varied over a tenfold range and were not related to CDAI response or nonresponse at week 8 (data not shown). These findings are consistent with dosing at the plateau of the dose-response curve.

VIII. Biomarkers

Patients in the MEDI2070 group had greater reductions in serum IL22 levels versus those in the placebo/MEDI2070 group (FIG. 7). Baseline serum IL22 levels greater than or equal to the median value of 15.6 pg/mL were associated with an increased likelihood of clinical effect in the MEDI2070 group. Patients in the MEDI2070 group with baseline IL22 levels less than 15.6 pg/mL had a CR100 response rate similar to that in the placebo group (FIG. 4). Clinical response was not a strong function of IL22 in the placebo group.

IX. Safety (i) Week 12

At the end of the double-blind period, the proportion of patients with treatment-emergent adverse events was similar tively) and serious adverse events (8.5% vs. 8.3%, respectively). Treatment-related adverse events were observed in 13.6% of patients receiving MEDI2070 and 21.7% of patients receiving placebo; those observed in at least 5% of patients in either group are shown in TABLE 3. Serious adverse events occurred in five patients in the MEDI2070 group and five in the placebo group; events included Crohn's disease (three events in two patients), colonoscopy-associated colon perforation (n=1), pyrexia (n=1), and cellulitis (n=1) in the MEDI2070 group, and anemia (n=1), Crohn's disease (two events in two patients), diarrhea (n=1), gastrointestinal hemorrhage (n=1), and abdominal abscess (n=1) in the placebo group.

TABLE 3

Treatment-Emergent Adverse Events in at Least 5% of Patients in Either Treatment Group (up to week 12; safety population)

| Adverse Event, n (%) | MEDI2070<br>(N = 59) | Placebo<br>(N = 60) |
|---|---|---|
| Headache | 10 (16.9) | 4 (6.7) |
| Nasopharyngitis | 8 (13.6) | 6 (10.0) |
| Abdominal pain | 6 (10.2) | 6 (10.0) |
| Crohn's disease | 5 (8.5) | 5 (8.3) |

TABLE 3-continued

Treatment-Emergent Adverse Events in at Least 5% of Patients
in Either Treatment Group (up to week 12; safety population)

| Adverse Event, n (%) | MEDI2070 (N = 59) | Placebo (N = 60) |
|---|---|---|
| Vomiting | 3 (5.1) | 2 (3.3) |
| Arthralgia | 3 (5.1) | 2 (3.3) |
| Proctalgia | 3 (5.0) | 0 |
| Dizziness | 3 (5.0) | 0 |
| Pyrexia | 2 (3.4) | 4 (6.7) |
| Nausea | 2 (3.4) | 3 (5.0) |
| Diarrhea | 0 | 5 (8.3) |
| Sinusitis | 0 | 4 (6.7) |
| Insomnia | 0 | 3 (5.0) |
| Cough | 0 | 3 (5.0) |

Infections that were serious or at least grade 3 in severity, or that required oral or parenteral antimicrobial therapy, occurred in four patients with four events in the MEDI2070 group, and in seven patients with 11 events in the placebo group. Treatment discontinuation attributable to treatment-emergent adverse events occurred in 8.5% of MEDI2070 patients (including gastrointestinal disorders [6.8%] and infection [1.7%]) and in 10.0% of placebo patients (including gastrointestinal disorders [6.7%], infection [1.7%], and eye disorder [1.7%]).

(ii) Week 24

At week 24, treatment-emergent adverse events were observed in 67.3% of patients in the MEDI2070 group and 65.4% of those in the placebo/MEDI2070 group, with treatment-related adverse events observed in 25.0% and 21.2% of patients, respectively. Treatment-emergent adverse events of at least grade 3 severity occurred in 13.5% of patients in the MEDI2070 group and 3.8% of patients in the placebo/MEDI2070 group; serious adverse events were observed in 15.4% and 7.7% of patients, respectively. Treatment discontinuation attributable to treatment-emergent adverse events occurred in 9.6% of MEDI2070 patients (including Crohn's disease flare [3.8%], anal fistula [1.9%], anemia and lymphopenia [1.9%], and anal abscess [1.9%]), and in 3.8% of placebo/MEDI2070 patients (including pelvic abscess [1.9%] and kidney stones [1.9%]). The number of infection events that were serious, at least grade 3 in severity, or required oral or parenteral antimicrobial therapy were equal in the MEDI2070 and placebo/MEDI2070 groups (13 events).

X. Immunogenicity

Antidrug antibodies were detected in two of 119 patients. One patient receiving MEDI2070 had antidrug antibodies at baseline, but not in subsequent assessments. The other patient, who received placebo during the double-blind period, had antidrug antibodies at week 24.

XI. Discussion

In patients with moderate to severe Crohn's disease who failed prior anti-TNF-α therapy, MEDI2070 resulted in a significantly greater rate of clinical effect, a composite of a 100-point reduction in CDAI and CDAI remission, at 8 weeks compared with placebo (49.2% vs. 26.7%, respectively; P=0.01), meeting the primary study end point. Clinical efficacy was consistent with the biologic effects observed with MEDI2070. Patients in the MEDI2070 group had greater decreases from baseline in FCP and CRP relative to placebo. The beneficial effects of MEDI2070 on FCP and CRP are remarkable given that this patient population was previously heavily treated with anti-TNF-α therapies; more than 65% of patients had received two or more prior anti-TNF-α agents.

At week 12, the rate of clinical effect was greater in the MEDI2070 group, as was the rate of CDAI remission; however, these differences were not significant. Significant reductions in FCP and CRP with MEDI2070 were maintained at week 12. At week 24, clinical effect, CDAI remission, and changes from baseline in levels of FCP and CRP were maintained between weeks 12 and 24 in the MEDI2070 group. Among patients in the placebo/MEDI2070 group, the proportion achieving clinical effect and CDAI remission at week 24 was similar to those who received MEDI2070 in both periods, and significant decreases in FCP and CRP levels were observed between weeks 12 and 24. At the 700-mg intravenous dose of MEDI2070, no definitive relationship between exposure and efficacy was established. This finding is consistent with dosing at the plateau of the dose-response curve. A wider range of doses will be explored in future studies.

MEDI2070 was well tolerated, with rates of treatment-emergent adverse events, grade 3 or greater adverse events, serious adverse events, and discontinuations owing to treatment-emergent adverse events similar to those of placebo at 12 weeks. Rates of serious or severe infections were less than 10% in the MEDI2070 group at week 12. At week 24, overall rates of treatment-emergent adverse events were similar between the MEDI2070 and placebo/MEDI2070 groups; rates of grade 3 or greater adverse events and serious adverse events were numerically greater in the MEDI2070 group versus the placebo/MEDI2070 group (13.5% vs. 3.8% and 15.4% vs. 7.7%, respectively), as were rates of discontinuations attributable to treatment-emergent adverse events (9.6% vs. 3.8%, respectively). Rates of serious or severe infections were the same in both treatment groups at 24 weeks (13 events). One patient had antidrug antibodies at baseline; presumably, this was a false-positive result and was not detected on follow-up assessment.

Although specific inclusion criteria, primary end points, and timing of assessments vary, the results of our study suggest that the short-term CDAI remission rate achieved with MEDI2070 (27.1% at 8 weeks) generally compares favorably with those of other biologic therapies evaluated in patients with Crohn's disease who failed prior anti-TNF-α therapy. These include ustekinumab (26% [7/27] at 8 weeks) (Sandborn et al. Gastroenterology 135:1130-41 (2008)), vedolizumab (10.5% [n=105] at 6 weeks), (Sandborn et al. N Engl J Med 369:711-21 (2013)) and adalimumab (21% [34/159 with secondary nonresponse to infliximab] at 4 weeks) (Sandborn et al. Ann Intern Med 146:829-38 (2007)). The safety profile of MEDI2070 also compares favorably with other biologics available for patients with Crohn's disease. A recent meta-analysis of studies evaluating the dual IL23/IL12 inhibitors ustekinumab and briakinumab found an increased risk of major adverse cardiovascular events in psoriasis patients treated for 12 to 20 weeks [Tzellos et al., J Eur Acad Dermatol Venereol, 27:1586-1587 (2013)]. No patients in our study experienced a major adverse cardiovascular event up to 24 weeks of follow-up. MEDI2070 is specific for IL23 and does not inhibit IL12; the clinical significance of this specificity is not known. However, follow-up for this study (104 weeks) is ongoing to determine longer-term efficacy and safety.

We evaluated serum IL22 levels at baseline and following MEDI2070 treatment. IL22, expressed at high levels in Crohn's disease, is an effector cytokine that supports mucosal barrier integrity and is an indicator of IL23 axis activity [Schmechel et al., Inflamm Bowel Dis, 14:204-212 (2008)]. Serum IL22 levels were reduced in the MEDI2070 group compared with the placebo group. Additionally, baseline serum IL22 levels greater than or equal to 15.6 pg/mL were associated with an increased likelihood of clinical effect in the MEDI2070 group, whereas MEDI2070-treated patients with baseline IL22 levels less than 15.6 pg/mL had CR100 responses similar to those in the placebo group. FIG. 4. In contrast, in a study by Dige et al., IL22 levels were not reduced in Crohn's disease patients effectively treated with adalimumab [Dige et al., J Crohns Colitis, 7:248-255 (2013)]. This study is among the first to incorporate novel biomarkers to further the understanding of the pathogenesis and improve the treatment of Crohn's disease.

In conclusion, MEDI2070 treatment demonstrated consistently robust efficacy, with an acceptable safety profile in patients with Crohn's disease who failed prior anti-TNF-α therapies.

Example 3

Immunoassays for Detection and Quantification of IL23 Pathway Biomarkers IL22 and LCN2

IL22 and/or LCN2 can be detected and quantified according to the exemplary methods disclosed in this Example (Example 3). These methods were applied, for example, to obtain the experimental data presented in Example 4 (see below). The methods were also used to test samples for the phase 2a study presented in Examples 1 and 2.

3.1 IL22 ELISA Immunoassay

IL22 levels were measured using a quantitative ELISA-based immunoassay. A mouse monoclonal antibody specific for human IL-22 was pre-coated onto a microplate (R&D Systems, Cat #D2200). One hundred microliters of assay diluent were first added to wells of microplates followed by addition of 100 µL of standards, controls and samples. The plates were incubated for 2 hours±15 minutes at room temperature to allow IL22 to bind to the capture antibody on the plates. Plates were then washed 5 times using 1× Wash buffer (1×PBS pH 7.4/0.05% Tween-20) to remove unbound materials and were further incubated with 200 µL of the detection antibody (anti-IL22 antibody-HRP conjugate, (R&D Systems, Cat #D2200) for 2 hours±15 minutes at room temperature. After that, the plates were washed again and incubated with 150 µL of TMB, a chromogenic HRP substrate (Neogen, Cat #331176) for 20 minutes±3 minutes at room temperature in the dark. The enzyme reaction was stopped by the addition of 100 µL of stop solution (1M HCL).

Within 30 minutes after stopping the reaction, plates were read on a SpectraMaxPlus 384 Microplate Spectrophotometer (Molecular Devices) to measure the optical density at 450 nm. The intensity of the color generated is directly proportional to the amount of bound IL22. The IL22 concentrations in samples and controls were interpolated from the standard curve of recombinant *E. coli*-derived IL22, which was run on each plate. The quadratic model was used for curve fitting. The assay was reproducible and precise. The quantifiable range was established to be 10 pg/mL-800 pg/mL of IL-22 in 100% serum.

3.2 LCN2 ELISA Immunoassay

A standard Meso Scale Discovery plate (MSD, Cat #L15XA) was coated with 1 µg/mL of a rat-anti-human Lipocalin-2 antibody (R&D Systems, Cat #MAB17571), at 50 µL/well at 2° C.-8° C. overnight. The plate was washed three times with 200 µL ELISA Wash Buffer (0.05% Tween-20/PBS) and blocked with 150 µL/well of I-Block buffer (IBB) (0.5% Tween-20/0.2% I-Block Buffer/PBS) for at least 60 minutes on a plate shaker with gentle shaking. Reference standards, quality controls and negative control, prepared in IBB, and serum test samples, diluted to the minimum required dilution of 1:50 in IBB, were added to the plate at 30 µL/well.

The assay plate was incubated for 2 hours at room temperature on a plate shaker with gentle shaking. Unbound analyte was removed by washing the plate. To detect bound analyte, 0.5 µg/mL of a biotin-conjugated goat-anti-human Lipocalin-2 antibody (R&D Systems, Cat #BAF1757) was added at 30 µL/well and the plate was incubated for an additional 60 minutes on a plate shaker with gentle shaking. Unbound detection antibody was removed by washing the plate. Streptavidin SULFO-TAG™ detection dye (MSD, Cat #R32AD-1) was added to the plate at 0.5 µg/well and the plate was incubated for an additional 30 minutes covered to protect from light exposure. The plate was washed and 1× Read Buffer (MSD, Cat #R92TC-2) was added at 150 µL/well and the plate was read on a MSD Sector Imager within 20 minutes.

ECL (electrochemiluminescence) values for each plate were collected using the MSD Sector Imager. The ECL values for the reference standards were plotted with Softmax Pro GxP v6.4 software (Molecular Devices, Sunnyvale, Calif.) using 5-Parameter Logistic model of curve fitting. The concentrations of unknown samples were interpolated from the standard curves on the same assay plate. The Softmax-derived data was then imported into Microsoft Excel Software to generate data reports and graphs. The assay's dynamic range was established to be from 0.70 ng/ml to 1000.00 ng/mL adjusted to 100% serum.

Example 4

Identification of IL23 Pathway Biomarkers (IL22 and/or LCN2) as Predicted Biomarkers for Treatment of IL23-Mediated Diseases with an Anti-IL23 Antibody IL23 is expressed primarily from activated dendritic cells and macrophages (see Gaffen et al (2014) Nature Revs Immunol 14: 585-600; Oppmann et al (2000) Immunity 13: 715-251) and acts directly on a variety of hematopoetic cell types including Th17, Th22, γδ T cells and innate lymphoid cells (ILCs) to induce cytokines including IL22, IL21, IL17A, IL17F, IL17A/F, TNF alpha and GM-CSF (see, e.g., Gaffen et al (2014) Nature Revs Immunol 14: 585-600; Zheng et al (2007) Nature 445: 648-51; El-Behi et al (2011) Nature Immunol 12: 568-575). These effector and regulatory cytokines can in turn act on a variety other cell types expressing the appropriate cognate receptors. IL23-induced IL22, for example, can stimulate IL22-receptor expressing epithelial cells and keratinocytes to secrete antimicrobial proteins such as LCN2 (Sonnenberg et al (2010) Adv Immunol 107: 1-29; Stallhofer et al (2015) Inflamm Bowel Dis 2015 Aug. 7; Behnsen et al (2014) Immunity 40: 262-73).

In the Phase 2a study described in Examples 1 and 2, CD patients with elevated baseline serum IL22 or LCN2 levels of greater than or equal to 15.6 pg/mL or 215 ng/mL, respectively (as measured using the immunoassays described in Example 3), had an increased likelihood of clinical effect in the MEDI2070 group, whereas MEDI2070-treated patients with baseline IL22 levels less than 15.6 pg/mL or 215 ng/mL, respectively, had CR100 responses similar to those in the placebo group. FIGS. 4 and 5. In particular, patients with baseline serum IL22 levels≥15.6 pg/mL or patients with baseline serum LCN2 levels≥215 ng/mL were observed to have statistically significant increased CDAI-100 responses when treated with MEDI2070 compared to placebo at week 8. FIGS. 4 and 5.

To further understand the relationship between baseline serum IL22 and/or LCN2 levels and response to treatment with MEDI2070, the set of baseline values of either IL22 or LCN2 across the entire study population was divided into 10 levels, or deciles, such that each of the 11 analyte cut-offs progressively segmented the study population into groups with 10% less of the total study population. The differential clinical response rate between MEDI2070 and placebo exposed subjects as a function of baseline IL22 and LCN2 serum levels at each decile cut-off is provided in FIGS. 6A-C and the individual IL22 and LCN2 serum decile values is summarized below in TABLE 4 (IL22) and TABLE 5 (LCN2). For example, as reported in TABLE 4, at the $4^{th}$ decile, 40% of the total study population had a baseline IL-22 level of <12.7 pg/mL and 60% of the total study population had a baseline IL-22 level≥12.7 pg/mL. The CDAI response rate at week 8 (as measured by the percentage (%) of subjects achieving a CDAI score<150 or a reduction in CDAI score of >100) in those subjects exposed to MEDI2070 and with baseline IL-22 levels≥12.7 pg/mL, i.e. above the $4^{th}$ decile, was 58.3%. 21 subjects exposed to MEDI2070 and with baseline IL22 levels above the $4^{th}$ decile for the study population (12.7 pg/ml) were found to be CDAI responders at week 8. The function in R called 'quantiles' was used to determine decile values. The numbers of CDAI responder and non-responders in the MEDI2070 and placebo exposed groups, and the CDAI response rates at week 8 of the study in subjects with baseline IL22 or LCN2 values greater than or equal to each decile cut are also indicated in TABLES 4 and 5, and differences between treatment and placebo response rates for each decile cut is provided in FIG. 6A. Two additional measurements of clinical response—the difference between the percentage (%) of subjects treated with MEDI2070 versus those treated with placebo achieving a 100 point improvement in CDAI score at week 8 (FIG. 6B); and the difference between the percentage (%) of subjects treated with MEDI2070 versus those treated with placebo achieving a CDAI response (CDAI score<150 or a reduction in CDAI score of >100)+also achieving a >50% reduction in either FCP or CRP compared to baseline FCP or CRP at week 8 (FIG. 6C)—as a function of baseline IL22 and LCN2 levels/deciles described in TABLES 4 or 5 were also performed.

As shown in FIGS. 6A-C and reported in TABLE 4 below, CD patients treated with MEDI2070 having increasingly higher levels of baseline IL22 achieved higher CDAI response rates at week 8 compared to placebo (as measured using any of the three different clinical response measurements shown in FIGS. 6A-C), illustrating that MEDI2070 induced better clinical responses in patients with high baseline IL22 serum levels. Notably, subjects with high levels of IL22 (including, e.g., subjects with IL22 levels at the $5^{th}$, $6^{th}$ or $7^{th}$ deciles (0.5, 0.6 or 0.7 quantiles)) had greater clinical response rate differences from placebo (irrespective of which of the three different clinical response measurements was used) compared to the IL22 low subjects (including, e.g. subjects with IL22 levels at the $1^{st}$ or $2^{nd}$ deciles (0.1 or 0.2 quantiles)). See FIGS. 6A-C. These IL22 high subjects also had increased CDAI response rates compared to all comers treated with MEDI2070 (see, e.g., FIG. 8).

Importantly, the CDAI response rates and CDAI remission rates observed in IL22 high subjects treated with MEDI2070 in the Phase 2a study are amongst the highest clinical response rates to biologics therapy for CD reported to date. For example, as shown in FIG. 8, the CDAI-100 response rate differential (defined as the difference in the percentage (%) of subjects achieving a CDAI-100 response between treatment and placebo) and/or CDAI remission rate differential (defined as the difference in the percentage (%) of subjects achieving a reduction in total CDAI score to below 150 points between treatment and placebo) achieved in patients having elevated baseline serum IL22 treated with MEDI2070 for 8 weeks were highly increased compared to the published CDAI-100 response and/or CDAI remission rates of patients treated with a number of other compounds currently approved or under development to treat CD including: Ustekinumab (response rates after 6 weeks or 8 weeks of treatment with a 6 mg/kg dose as reported in FIG. 1 of Sandborn et al., N Engl J Med. 2012 Oct. 18; 367(16):1519-28); Vedolizumab (response rates after 6 weeks or 10 weeks of treatment as reported in FIG. 3 of Sands et. al., Gastroenterology. 2014 September; 147(3):618-627); or Adalimumab (response rates after 4 weeks of treatment in patients who are secondary failures to infliximab as reported in Sandborn et. al, Ann Intern Med. 2007; 146:829-838). For example, both the CDAI-100 response rate differential ("CDAI Response Delta vs. Placebo") and the CDAI remission rate differential ("CDAI Remission Delta vs. Placebo") achieved in patients treated with MEDI2070 for 8 weeks who had a baseline CRP≥5 mg/L; baseline IL-22≥11.3 pg/mL; baseline IL-22≥15.6 pg/mL; or baseline IL-22≥11.3 pg/mL+CRP≥5 mg/L (as measured using the IL22 immunoassay described in Example 3) were greater than the reported CDAI-100 response rate differential and/or the CDAI remission rate differential for Ustekinumab, Vedolizumab and Adalimumab reported in FIG. 8. The overall clinical response and remission rates for all patients treated with MEDI2070 in the Phase 2a study, irrespective of biomarker status, was similar to the response rates of other molecules currently approved or under development. TABLE 6 summarizes the CDAI-100 response rate differential and the CDAI remission rate differential for each of the MEDI2070-treated subgroups plotted in FIG. 8. These results further underscore the surprising and unexpected predictive value of high or elevated IL22 serum levels (alone or in combination with other biomarkers disclosed herein) in identifying patients having an IL23-mediated disease or disorder responsive to treatment with an IL23 antagonist (including, e.g., an anti-IL23 antibody or fragment thereof such as MEDI2070).

Similarly, as shown in FIGS. 6A-C and reported in TABLE 5, CD patients treated with MEDI2070 having increasingly higher levels of baseline LCN2 achieved higher clinical response rates (as measured using any of the three different clinical response measurements shown in FIGS. 6A-C) at week 8 compared to placebo, supporting that MEDI2070 induced better clinical responses in patients with high baseline LCN2 serum levels. Notably, LCN2 high subjects (including, e.g., subjects with LCN2 levels at the $5^{th}$, $6^{th}$ or $7^{th}$ deciles (0.5, 0.6 or 0.7 quantiles)) had greater clinical response rate differences from placebo (irrespective of which of the three different clinical response measurements was used) compared to the LCN2 low subjects (including, e.g. subjects with LCN2 levels at the 1st or $2^{nd}$ deciles (0.1 or 0.2 quantiles)). These results further demonstrate the surprising and unexpected predictive value of high or elevated LCN2 serum levels in identifying patients having an IL23-mediated disease or disorder responsive to treatment with an IL23 antagonist (including, e.g., an anti-IL23 antibody or fragment thereof such as MEDI2070).

The relationship between increasing clinical response rates and increasing baseline biomarker levels was not always as evident in patients in the $8^{th}$, $9^{th}$ or $10^{th}$ deciles. At these IL22 or LCN2 levels too few, if any, patients treated with MEDI2070 or placebo were available for analysis. See, e.g., FIGS. 6A-C; TABLES 4 and 5. However, given a larger sample size, increased clinical response rates for patients identified as having IL22 or LCN2 levels at the $8^{th}$, $9^{th}$ or $10^{th}$ deciles are expected.

Taken together, these results support that high IL22 serum levels and/or high LCN2 serum levels (including, e.g., the median baseline IL22 and/or LCN2 serum levels identified in the study or serum IL22 levels between 7.9 pg/mL and 31.4 pg/mL and/or serum LCN2 levels between 142.8 ng/mL and 261.1 ng/mL) can be used to identify a patient having an IL23-mediated disease or disorder suitable for treatment with an IL23 antagonist (including, e.g., an anti-IL23 antibody or fragment thereof such as MEDI2070).

TABLE 6

CDAI-100 response rate differential (defined as the difference in the percentage (%) of subjects achieving a CDAI-100 response between treatment and placebo) and CDAI remission rate differential (defined as the difference in the percentage (%) of subjects achieving a total CDAI score of below 150 points between treatment and placebo) for various subgroups.

| population | N | MEDI2070 CDAI Response Rate Minus Placebo CDAI Response Rate at Week 8 | MEDI2070 CDAI Remission Rate Minus Placebo CDAI Remission Rate at Week 8 |
|---|---|---|---|
| mITT | N = 119 | 20.8% | 12.2% |
| IL22 >=11.3 pg/mL | N = 81 | 31.5% | 18.3% |
| IL22 >=15.6 pg/mL | N = 58 | 38.2% | 29.2% |
| CRP >=5 | N = 85 | 30.8% | 19.8% |
| CRP >=5 + IL22 >=11.3 pg/mL | N = 62 | 44.4% | 26.9% |

As noted previously, IL23-induced IL22 induces cells to secrete LCN2. Thus, the observation that baseline serum levels of two separate IL23 pathway members (i.e. elevated IL22 or LCN2) each were predictive of patient clinical response to MEDI2070 (e.g. CDAI-100 Response Rate at week 8) strongly suggests that other IL23 pathway biomarkers may also predict an increased likelihood of clinical effect in response to treatment with MEDI2070. Accordingly, to the extent that serum baseline levels of IL22 and/or LCN2

TABLE 4

Subject counts and CDAI Response Rate at Week 8 by Decile Baseline IL22 Levels.

| Decile | Baseline IL-22 (pg/mL) | MEDI2070 responders (# subjects) | MEDI2070 Non-responders (# subjects) | Placebo responders (# subjects) | Placebo Non-responders (# subjects) | MEDI2070 CDAI Response rate (W 8) | Placebo CDAI Response rate (W 8) |
|---|---|---|---|---|---|---|---|
| 0 | 1 | 28 | 28 | 16 | 44 | 0.5000 | 0.2667 |
| 1 | 1 | 28 | 28 | 16 | 44 | 0.5000 | 0.2667 |
| 2 | 7.9 | 25 | 22 | 10 | 36 | 0.5319 | 0.2174 |
| 3 | 11.3 | 24 | 18 | 9 | 30 | 0.5714 | 0.2308 |
| 4 | 12.7 | 21 | 15 | 9 | 25 | 0.5833 | 0.2647 |
| 5 | 15.6 | 20 | 10 | 7 | 21 | 0.6667 | 0.2500 |
| 6 | 19.6 | 18 | 8 | 5 | 16 | 0.6923 | 0.2381 |
| 7 | 23.1 | 14 | 5 | 5 | 11 | 0.7368 | 0.3125 |
| 8 | 31.4 | 9 | 5 | 3 | 7 | 0.6429 | 0.3000 |
| 9 | 46.8 | 3 | 4 | 2 | 3 | 0.4286 | 0.4000 |
| 10 | 711 | 0 | 1 | 0 | 0 | | |

TABLE 5

Subject counts and CDAI Response Rate at Week 8 by Decile Baseline LCN2 Levels.

| Decile | Baseline LCN2 (ng/mL) | MEDI2070 Responders (# subjects) | MEDI2070 Non-responders (# subjects) | Placebo Responders (# subjects) | Placebo Non-responders (# subjects) | MEDI2070 CDAI Response rate (W 8) | Placebo CDAI response rate (W 8) |
|---|---|---|---|---|---|---|---|
| 0 | 77.7 | 28 | 22 | 15 | 35 | 0.5600 | 0.3000 |
| 1 | 142.8 | 27 | 19 | 13 | 31 | 0.5870 | 0.2955 |
| 2 | 163.6 | 23 | 16 | 12 | 29 | 0.5897 | 0.2927 |
| 3 | 184.3 | 21 | 14 | 12 | 23 | 0.6000 | 0.3429 |
| 4 | 201.3 | 20 | 14 | 6 | 20 | 0.5882 | 0.2308 |
| 5 | 214.6 | 18 | 12 | 4 | 16 | 0.6000 | 0.2000 |
| 6 | 233.4 | 16 | 8 | 3 | 13 | 0.6667 | 0.1875 |
| 7 | 261.1 | 14 | 6 | 3 | 7 | 0.7000 | 0.3000 |
| 8 | 294.8 | 10 | 4 | 2 | 4 | 0.7143 | 0.3333 |
| 9 | 326.6 | 5 | 2 | 1 | 2 | 0.7143 | 0.3333 |
| 10 | 434.0 | 0 | 0 | 1 | 0 | | | or any other IL23 pathway analyte (including, e.g., CCL20, IL17F, IL17A/F, IL23R, IL12B, IL6, IL21, TNF, CCR6, CCL22, IL1R1, IFN-γ, S100A12, DEFB-2, DEFB-4, IL1, SERPINB3, PI3/Elafin, LL37, RORγ, RORγT, IL26, S100A7, DEFB103B, or GM-CSF) reflects increased IL23 axis activity, a patient determined to have increased IL23 pathway activity (as determined by measuring one or more IL23 pathway biomarkers) may be more likely to benefit from treatment with an IL23 antagonist (including, e.g., an anti-IL23 antibody or an antigen-binding fragment thereof such as MEDI2070).

While the present invention has been described in terms of specific aspects, it is understood that variations and modifications will occur to those skilled in the art. Accordingly, only such limitations as appear in the claims should be placed on the invention.

The breadth and scope of the present invention should not be limited by any of the above-described exemplary aspects, but should be defined only in accordance with the following claims and their equivalents.

The foregoing description of the specific aspects will so fully reveal the general nature of the invention that others can, by applying knowledge within the skill of the art, readily modify and/or adapt for various applications such specific aspects, without undue experimentation, without departing from the general concept of the present invention. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

This application claims the benefit of the filing date of U.S. Provisional Application No. 62/220,062 filed on Sep. 17, 2015, which is incorporated by reference in its entirety herein.

What is claimed is:

1. A method of treating Crohn's disease or Inflammatory Bowel Disease in a patient, comprising administering an IL23 antagonist to a patient in an amount and at an interval of:
   (a) 15-54 mg every 0.5-1.5 months;
   (b) 55-149 mg every 1.5-4.5 months;
   (c) 150-299 mg every 4-8 months; or
   (d) 300-1100 mg every 4-12 months
   if the patient is determined to have (i) a higher or increased level of interleukin-22 (IL22) and/or (ii) a higher or increased level of lipocalin 2 (LCN2) in one or more samples taken from the patient compared to a predetermined IL22 and/or LCN2 threshold level, or compared to a IL22 and/or LCN2 level in one or more control samples, or suspending the administration of an IL23 antagonist to a patient if the patient is determined to have (i) a lower or decreased level of interleukin-22 (IL22) and/or (ii) a lower or decreased level of lipocalin 2 (LCN2) in one or more samples taken from the patient compared to a predetermined IL22 and/or LCN2 threshold level, or compared to a IL22 and/or LCN2 level in one or more control samples.

2. The method according to claim 1, further comprising measuring the level of IL22 and/or LCN2 in one or more of the samples obtained from the patient or instructing a clinical laboratory or healthcare provider to measure the level of IL22 and/or LCN2 in the sample and/or submitting the one or more samples obtained from the patient to a clinical laboratory or healthcare provider to measure the level of IL22 and/or LCN2 in the sample.

3. The method according to claim 1 further comprising advising a healthcare provider to administer an IL23 antagonist to the patient in an amount and at an interval of:
   (a) 15-54 mg every 0.5-1.5 months;
   (b) 55-149 mg every 1.5-4.5 months;
   (c) 150-299 mg every 4-8 months; or
   (d) 300-1100 mg every 4-12 months,
   if the patient is determined to have (i) a higher or increased level of IL22 and/or (ii) a higher or increased level of LCN2 in one or more of the samples compared to a predetermined IL22 and/or LCN2 threshold level, or compared to a IL22 and/or LCN2 level in one or more control samples, or to suspend the administration of an IL23 antagonist to the patient if the patient is determined to have (i) a lower or decreased level of IL22 and/or (ii) a lower or decreased level of LCN2 in one or more of the samples compared to a predetermined IL22 and/or LCN2 threshold level, or compared to a IL22 and/or LCN2 level in one or more control samples.

4. The method according to claim 1, wherein the IL23 antagonist is an anti-IL23 antibody or antigen-binding fragment thereof.

5. The method of claim 4, wherein the anti-IL23 antibody or antigen-binding fragment thereof binds to the p19 subunit of IL23 (SEQ ID NO: 13), to the p40 subunit of IL23 (SEQ ID NO: 14), or both.

6. The method according to claim 4, wherein the anti-IL23 antibody or antigen-binding fragment thereof comprises ustekinumab, briakinumab, guselkumab, BI-655066, tildrakinumab, LY-3074828, or an antigen-binding fragment thereof.

7. The method according to claim 4, wherein the anti-IL23 antibody or antigen-binding fragment thereof comprises (i) a variable region (VH) comprising or consisting of SEQ ID NO: 5 and/or a light chain variable region (VL) comprising or consisting of SEQ ID NO: 6, or (ii) a variable region (VH) comprising or consisting of SEQ ID NO:43 and/or a light chain variable region (VL) comprising or consisting of SEQ ID NO: 44.

8. The method according to claim 4, wherein the anti-IL23 antibody or antigen-binding fragment thereof comprises six complementarity determining regions selected from SEQ ID NOS: 31-36 or SEQ ID NOS:45-50.

9. The method according to claim 4, wherein the antibody is administered at a fixed dose.

10. The method according to claim 9, wherein the fixed dose is between 15 and 1000 mg/dose, is about 210 mg/dose, or is about 700 mg/dose.

11. The method according to claim 1 wherein the patient has been treated before, during, or after the administration of an IL23 antagonist or anti-IL23 antibody or antigen-binding fragment with one or more additional therapies for the treatment of Crohn's disease or Inflammatory Bowel Disease.

12. The method according to claim 1, wherein the one or more control samples are (i) a sample or samples obtained from normal healthy individuals; (ii) a sample or samples obtained from patients without Crohn's disease or Inflammatory Bowel Disease; or (iii) a combination thereof.

13. The method according to claim 1, further comprising determining the level of one or more IL23 Pathway Biomarkers selected from the group consisting of CCL20, IL17F, IL17A/F, IL23R, IL12B, IL6, IL21, TNF, CCR6, CCL22, IL1R1, IFN-γ, S100AI2, DEFB-2, DEFB-4, ILI, SERPINB3, PI3/Elafin, LL37, RORy, RORyT, IL26, S100A7, DEFB103B, and GM-CSF.

14. The method according to claim 1, wherein the predetermined threshold level of IL22 and/or LCN2 is selected from the group consisting of:
   (a) about the mean level of IL22 and/or LCN2;
   (b) about the median level of IL22 and/or LCN2;
   (c) about the $1^{st}$, $2^{nd}$, $3^{rd}$, $4^{th}$, $5^{th}$, $6^{th}$, $7^{th}$, $8^{th}$, or $9^{th}$ decile baseline level of IL22 and/or LCN2 as described in TABLES 4 or 5, as measured in the serum using an immunoassay from a plurality of normal healthy patients, patients without Crohn's disease or Inflammatory Bowel Disease, and/or patients with without Crohn's disease or Inflammatory Bowel Disease, or wherein
   (d) the predetermined IL22 threshold level is at least about 7.9 pg/mL to at least about 31.4 pg/mL as measured using an immunoassay;

(e) the predetermined LCN2 threshold level is at least about 143 ng/mL to at least about 261 ng/mL as measured using an immunoassay;

(f) the predetermined IL22 threshold level is about 15.6 pg/mL as measured using an immunoassay; and/or (g) the predetermined LCN2 threshold level is about 215 ng/mL as measured using an immunoassay.

15. The method according to claim 1, wherein the patient has Crohn's disease, and wherein the patient is determined to have a level of CRP >5 mg/L and/or a level of FCP >250 µg/g, a level of FCP >20 µg/g, a level of FCP >150 µg/g, a level of FCP >10 µg/g, or a level of FCP at least about 10 µg/g to at least about 250 µg/g in one or more samples taken from the patient.

16. The method according to claim 15, wherein administration of the IL23 antagonist results in a Crohn's Disease Activity Index (CDAI) response score reduction of at least 10 points and/or a reduction in the total CDAI score to below 150 points after first administering the anti-IL23 antibody or antigen-binding fragment thereof.

17. The method according to claim 16, wherein the CDAI response score reduction of at least 10 points or reduction in the total CDAI score to below 150 points occurs within 1, 2, 4, 8, 12, 16 or 24 weeks or later after first administering the IL23 antagonist.

18. The method according to claim 16, wherein the IL23 antagonist is an anti-IL23 antibody or antigen-binding fragment thereof.

19. The method according to claim 17, wherein the IL23 antagonist is an anti-IL23 antibody or antigen-binding fragment thereof.

20. The method of claim 1, wherein the amount and interval are:

(a) 15-21 mg every 0.5-1.0 month;

(b) 55-70 mg every 1.5-3.0 months;

(c) 150-260 mg every 4-6 months; or (d) 300-700 mg every 4-8 months.

21. The method of claim 1, wherein the amount and interval are:

(a) 21 mg every month;

(b) 70 mg every 3 months;

(c) 210 mg every 6 months; or (d) 700 mg every 6 months.

22. A method of selecting a patient diagnosed with Crohn's disease or Inflammatory Bowel Disease as a candidate for treatment with an IL23 antagonist in an amount and at an interval of:

(a) 15-54 mg every 0.5-1.5 months;

(b) 55-149 mg every 1.5-4.5 months;

(c) 150-299 mg every 4-8 months; or (d) 300-1100 mg every 4-12 months, comprising:

(i) measuring the levels of interleukin-11 (IL-22) and/or of lipocalin 2 (LCN2) in one or more samples obtained from the patient;

(ii) selecting the patient for treatment if the patient is determined to have a higher or increased level IL22 and/or a higher or increased level of LCN2 compared to a predetermined IL22 and/or LCN2 threshold level, or compared to a IL22 and/or LCN2 level in one or more control samples and (iii) administering the IL23 antagonist at said dosages and intervals to the patient.

* * * * *

UNITED STATES PATENT AND TRADEMARK OFFICE
CERTIFICATE OF CORRECTION

PATENT NO. : 11,016,099 B2
APPLICATION NO. : 15/759330
DATED : May 25, 2021
INVENTOR(S) : Robert W. Georgantas, III et al.

Page 1 of 1

It is certified that error appears in the above-identified patent and that said Letters Patent is hereby corrected as shown below:

On the Title Page

At item (72), Line 13, "Yen-Wah Lee," should be -- Yen-Wah Lee, Deceased, --.

At item (57), Line 10, "such a" should be -- such as --.

At item (57), Line 12, "ant-IL23" should be -- anti-IL23 --.

In the Claims

At Column 141, Line 18, "months" should be -- months, --.

At Column 142, Lines 11-12, "tildrakinumab," should be -- tildrakizumab, --.

At Column 142, Line 49, "RORy, RORyT," should be -- RORγ, RORγT, --.

At Column 144, Line 26, "level IL22" should be -- level of IL22 --.

At Column 144, Line 29, "samples and" should be -- samples; and --.

Signed and Sealed this
Fifth Day of April, 2022

Drew Hirshfeld
*Performing the Functions and Duties of the
Under Secretary of Commerce for Intellectual Property and
Director of the United States Patent and Trademark Office*